United States Patent
Brinker et al.

(10) Patent No.: US 9,579,283 B2
(45) Date of Patent: Feb. 28, 2017

(54) POROUS NANOPARTICLE-SUPPORTED LIPID BILAYERS (PROTOCELLS) FOR TARGETED DELIVERY AND METHODS OF USING SAME

(75) Inventors: C. Jeffrey Brinker, Albuquerque, NM (US); Eric C. Carnes, Albuquerque, NM (US); Carlee Erin Ashley, Albuquerque, NM (US); Cheryl L. Willman, Albuquerque, NM (US)

(73) Assignees: STC.UNM, Albuquerque, NM (US); Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/113,371

(22) PCT Filed: Apr. 27, 2012

(86) PCT No.: PCT/US2012/035529
§ 371 (c)(1),
(2), (4) Date: Dec. 4, 2013

(87) PCT Pub. No.: WO2012/149376
PCT Pub. Date: Nov. 1, 2012

(65) Prior Publication Data
US 2014/0079774 A1    Mar. 20, 2014

Related U.S. Application Data

(60) Provisional application No. 61/479,847, filed on Apr. 28, 2011.

(51) Int. Cl.
| | | |
|---|---|---|
| A61K 9/127 | (2006.01) |
| A61K 31/704 | (2006.01) |
| A61K 31/711 | (2006.01) |
| A61K 45/06 | (2006.01) |
| A61K 47/48 | (2006.01) |
| C07K 14/47 | (2006.01) |
| C12N 15/88 | (2006.01) |
| A61K 33/24 | (2006.01) |
| A61K 39/05 | (2006.01) |
| C12N 15/113 | (2010.01) |
| A61K 38/00 | (2006.01) |
| A61K 48/00 | (2006.01) |

(52) U.S. Cl.
CPC .......... *A61K 9/1271* (2013.01); *A61K 31/704* (2013.01); *A61K 31/711* (2013.01); *A61K 33/24* (2013.01); *A61K 39/05* (2013.01); *A61K 45/06* (2013.01); *A61K 47/48238* (2013.01); *A61K 47/48776* (2013.01); *C07K 14/47* (2013.01); *C12N 15/1135* (2013.01); *C12N 15/88* (2013.01); *A61K 38/00* (2013.01); *A61K 48/0016* (2013.01); *C12N 2310/14* (2013.01); *C12N 2320/32* (2013.01); *C12N 2810/40* (2013.01)

(58) Field of Classification Search
None
See application file for complete search history.

(56) References Cited

U.S. PATENT DOCUMENTS

| 5,277,913 A | 1/1994 | Thompson et al. |
| 5,753,263 A | 5/1998 | Lishko et al. |
| (Continued) | | |

FOREIGN PATENT DOCUMENTS

| JP | 2009-515520 A | 4/2009 |
| WO | 00/76556 A2 | 12/2000 |
| (Continued) | | |

OTHER PUBLICATIONS

Ashley, et al. (Online Apr. 17, 2011) "The targeted delivery of multicomponent cargos to cancer cells by nanoporous particle-supported lipid bilayers", Nature Materials, 10: 289-97.*
Lo, et al. (2008) "Hepatocellular carcinoma cell-specific peptide ligand for targeted drug delivery", Molecular Cancer Therapeutics, 7(3): 579-89.*
Raskopf, et al. (2008) "siRNA targeting VEGF inhibits hepatocellular carcinoma growth and tumor angiogenesis in vivo", Journal of Heptaology, 49: 977-84.*
Zelphati, et al. (1996) "Mechanism of oligonucleotide release from cationic liposomes", Proceedings of the National Academy of Sciences, USA., 93: 11493-89.*
Videira, et al. (2006) "Lymphatic uptake of lipid nanoparticles following endotracheal administration", Journal of Microencapsulation: Micro and Nano Carriers, 23(8): 855-62.*

(Continued)

*Primary Examiner* — Robert M Kelly
(74) *Attorney, Agent, or Firm* — Schwegman Lundberg & Woessner, P.A.

(57) ABSTRACT

The present invention is directed to protocells for specific targeting of hepatocellular and other cancer cells which comprise a nanoporous silica core with a supported lipid bilayer; at least one agent which facilitates cancer cell death (such as a traditional small molecule, a macromolecular cargo (e.g. siRNA or a protein toxin such as ricin toxin A-chain or diphtheria toxin A-chain) and/or a histone-packaged plasmid DNA disposed within the nanoporous silica core (preferably supercoiled in order to more efficiently package the DNA into protocells) which is optionally modified with a nuclear localization sequence to assist in localizing protocells within the nucleus of the cancer cell and the ability to express peptides involved in therapy (apoptosis/cell death) of the cancer cell or as a reporter, a targeting peptide which targets cancer cells in tissue to be treated such that binding of the protocell to the targeted cells is specific and enhanced and a fusogenic peptide that promotes endosomal escape of protocells and encapsulated DNA. Protocells according to the present invention may be used to treat cancer, especially including hepatocellular (liver) cancer using novel binding peptides (c-MET peptides) which selectively bind to hepatocellular tissue or to function in diagnosis of cancer, including cancer treatment and drug discovery.

45 Claims, 74 Drawing Sheets

(56) References Cited

U.S. PATENT DOCUMENTS

| | | | |
|---|---|---|---|
| 5,820,879 | A | 10/1998 | Fernandez et al. |
| 7,101,967 | B2 * | 9/2006 | Fischer et al. ............. 530/329 |
| 7,514,267 | B1 | 4/2009 | Lopez et al. |
| 8,298,677 | B2 | 10/2012 | Wiesner et al. |
| 8,734,816 | B2 * | 5/2014 | Liu et al. ............. 424/400 |
| 8,992,984 | B1 | 3/2015 | Brinker et al. |
| 2002/0039594 | A1 | 4/2002 | Unger |
| 2004/0005352 | A1 | 1/2004 | Lopez et al. |
| 2004/0101822 | A1 | 5/2004 | Wiesner et al. |
| 2004/0258671 | A1 | 12/2004 | Watkins |
| 2006/0154069 | A1 | 7/2006 | Lin et al. |
| 2008/0095852 | A1 | 4/2008 | Kong et al. |
| 2008/0160313 | A1 | 7/2008 | Lopez et al. |
| 2008/0213377 | A1 | 9/2008 | Bhatia et al. |
| 2008/0279764 | A1 | 11/2008 | Manganaro et al. |
| 2009/0054246 | A1 | 2/2009 | Peabody et al. |
| 2009/0324706 | A1 | 12/2009 | Mirkin et al. |
| 2010/0055167 | A1 | 3/2010 | Zhang et al. |
| 2010/0255103 | A1 | 10/2010 | Liong et al. |
| 2011/0105995 | A1 | 5/2011 | Zhu et al. |
| 2011/0230372 | A1 | 9/2011 | Willman et al. |
| 2011/0268791 | A1 | 11/2011 | Liu |
| 2011/0300186 | A1 | 12/2011 | Hellstrom et al. |
| 2014/0079774 | A1 | 3/2014 | Brinker et al. |
| 2014/0212479 | A1 | 7/2014 | Zeinelden |
| 2014/0301951 | A1 | 10/2014 | Liu et al. |
| 2015/0010475 | A1 | 1/2015 | Brinker et al. |
| 2015/0164798 | A1 | 6/2015 | Brinker et al. |
| 2016/0106671 | A1 | 4/2016 | Brinker et al. |

FOREIGN PATENT DOCUMENTS

| | | | |
|---|---|---|---|
| WO | WO 02066506 A2 * | 8/2002 | ......... C07K 14/4748 |
| WO | 03/016040 A1 | 2/2003 | |
| WO | 03/055469 A1 | 7/2003 | |
| WO | 2005009602 A2 | 2/2005 | |
| WO | 2007/140618 A1 | 12/2007 | |
| WO | 2009078924 A2 | 6/2009 | |
| WO | 2010/048572 A1 | 4/2010 | |
| WO | 2010078569 A2 | 7/2010 | |
| WO | 2011/116226 A2 | 9/2011 | |
| WO | 2012149376 A2 | 11/2012 | |
| WO | 2013012891 A1 | 1/2013 | |
| WO | 2013056132 A2 | 4/2013 | |
| WO | 2013/103614 A1 | 7/2013 | |
| WO | 2014/165608 A1 | 10/2014 | |
| WO | 2014/165617 A1 | 10/2014 | |
| WO | 2015042279 A1 | 3/2015 | |

OTHER PUBLICATIONS

Ferrari M. Cancer Nanotechnology: Opportunities and Challenges. Nature, 2005;5:161-171.

Carroll NJ, et al. Microparticles with Bimodal Nanoporosity Derived by Microemulsion Templating. Langmuir, 2009.

Lu YF, et al. Aerosol-assisted self-assembly of mesostructured spherical nanoparticles. Nature, 1999;398:223-226.

Iler RK. The Chemistry of Silica: Solubility, Polymerization, Colloid and Surface Properties, and Biochemistry. Jon Wiley and Sons, 1979.

Doshi DA, et al. Neutron Reflectivity Study of Lipid Membranes Assembled on Ordered Nanocomposite and Nanoporous Silica Thin Films. Langmuir, 2005;21:2865-2870.

Bernhard Mi, et al. Guinea Pig Line 10 Hepatocarcinoma Model: Characterization of Monoclonal Antibody and in Vivo Effect of Unconjugated Antibody and Antibody Conjugated to Diphtheria Toxin A Chain. Cancer Research, 1983;43:4420-4428.

Lo A, et al. Hepatocellular carcinoma cell-specific peptide ligand for targeted drug delivery. Molecular Cancer Therapeutics, 2008;7:579-589.

Sciot R, et al. Transferrin receptor expression in human hepatocellular carcinoma: an immunohistochemical study of 34 cases. Histopathology, 1988;12:53-63.

Kannangai R, et al. EGFR is phospholylated at Tr845 in hepatocellular carcinoma. Mod Pathol, 2006;19:1456-1461.

Behr JP. The Proton Sponge: a Trick to Enter Cells the Viruses Did Not Exploit. CHIMIA International Journal for Chemistry, 1997;51:34-36.

Jiang W, et al. Nanoparticle-mediated cellular response is size-dependent. Nat Nano 3, 2008;145-150.

Zimmermann R, et al. Charging and structure of zwitterionicsupported bilayer lipid membranes studied by streaming current measurements, fluorescence microscopy, and attenuated total reflection Fourier transform infrared spectroscopy. Biointerphases, 2009;4:1-6.

Ashihara E, et al. Future Prospect of RNA Interference for Cancer Therapies. Current Drug Targets, 2010;11:345-360.

Pawitan JA. The possible use of RNA interference in diagnosis and treatment of various diseases. International Journal of Clinical Practice, 2009;63:1378-1385.

Elbashir SM, et al. Duplexes of 21-nucleotide RNAs mediate RNA interference in cultured mammalian cells. Nature, 2001;411:494-498.

Davis Me, et al. Evidence of RNAi in humans from systemically administered siRNA via targeted nanoparticles. Nature, 2010.

Oh YK, Park TG. siRNA delivery systems for cancer treatment, Advanced Drug Delivery Reviews, 2009:61:850-862.

Sou K, et al. Poly(ethylene glycol)—Modification of the Phospholipid Vesicles by Using the Spontaneous Incorporation of Poly(ethylene glycol)-Lipid into the Vesicles. Bioconjugate Chemistry, 2000;11:372-379.

Klein E, et al. "HFP" Fluorinated Cationic Lipids for Enhanced Lipoplex Stability and Gene Delivery. Bioconjugate Chemistry, 2010;360-371.

Minguez B, et al. Pathogenesis of hepatocellular carcinoma and molecular therapies. Current Opinion in Gastroenterology, 2009;25:186-194.

Li SD, et al. Tumor-targeted Delivery of siRNA by Self-assembled Nanoparticles. Mol Ther, 2007;16:163-169.

Landen CN, et al. Therapeutic EphA2 Gene Targeting in vivo Using Neutral Liposomal Small Interfering RNA Delivery. Cancer Research, 2005;65:6910-6918.

Honjo T, et al. Diptheria Toxin-dependent Adenosine Diphosphate Ribosylation of Aminoacyl Transferase II and Inhibition of Protein Synthesis. Journal of Biological Chemistry, 1968;243:3553-3555.

Uchida T, et al. Reconstitution of lipid vesicles associated with HVJ (Sendai virus) spikes. Purification and some properties of vesicles containing non-toxic fragment A of diphtheria toxin. Journal of Cell Biology, 1979;80:10-20.

Mizuguchi H, et al. Application of fusogenic liposomes containing fragment A of diphtheria toxin to cancer therapy. British Journal of cancer, 1997;73:472-476.

Liu JW, et al. Electrostatically Mediated Liposome Fusion and Lipid Exchange with a Nanoparticle-supported Bilayer for Control of Surface Charge, Drug Containment, and Delivery. Journal of the American Chemical Society, 2009;131:7567.

Liu JW, et al. Silica nanoparticle supported lipid bilayers for gene delivery. Chemical Communications, 2009:5100-5102.

Liu JW, et al. Porous Nanoparticle Supported Lipid Bilayers (Protocells) as Delivery Vehicles. Journal of the American Chemical Society, 2009;131:1354.

Schagger H. Tricine—SDS—PAGE. Nat Protocols, 2006;1:16-22.

Fritze A, et al. Remote loading of doxorubicin into liposomes driven by a transmembrane phosphate gradient. Biochimica et Biophysica Acta (BBA)—Biomembranes, 2006;1758:1633-1640.

Elorza B, et al. Characterization of 5-fluorouracil loaded liposomes prepared by reverse-phase evaporation or freezing-thawing extrusion methods: study of drug release. Biochimica et Biophysica Acta, 1993;1153:135-142.

Peleg-Shulman T, et al. Characterization of sterically stabilized cisplatin liposomes by nuclear magnetic resonance. Biochimica et Biophysica Acta, 2001;1510:278-291.

Bogush T, et al. Direct evaluation of intracellular accumulation of free and polymer-bound anthracyclines. Cancer Chemotherapy and Pharmacology, 1995;35:501-505.

(56) References Cited

OTHER PUBLICATIONS

Tong AW, et al. Chemosensitization of human hepatocellular carcinoma cells with cyclosporine A in post-liver transplant patient plasma. Clin Cacner Res, 1996;2:531-539.

Minko T, et al. Chronic exposure to HPMA copolymer-bound adriamycin does not induce multidrug resistance in a human ovarian carcinoma cell line. Journal of Controlled Release, 1999;59:133-148.

Huh S, et al. Organic Functionalization and Morphology Control of Mesoporous Silicas via a Co-Condensation Synthesis Method. Chem Mater, 2003;15:4247-4256.

Liu J, et al. Molecular Assembly in Ordered Mesoporosity: A New Class of Highly Functional Nanoscale Materials. J Phys Chem A, 2000;104:8328-8339.

Fan H, et al. Rapid prototyping of patterned functional nanostructures. Nature, 2000;405:56-60.

Lu Y, et al. Evaporation-Induced Self-Assembly of Hybrid Bridged Silsesquioxane Film and Particulate Mesophases with Integral Organic Functionality. J Am Chem Soc, 2000;122:5258-5261.

Zhao P, et al. Identification of a Met-Binding Peptide from a Phage Display Library. Clin Cancer Res, 2007;13:6049-6055.

Brammer LA, et al. A target-unrelated peptide in an M13 phage display library traced to an advantageous mutation in the gene II ribosome-binding site. Analytical Biochemistry, 2008;373:88-98.

Carroll NJ, et al. Microparticles with bimodal Nanoporosity Derived by Microemulsion Templating. Langmuir, 2009;25(23):13540-13544.

Liu J, Stace-Naughton A, Brinker JC. Silica nanoparticle supported lipid bilayers for gene delivery. Chem Commun, 2009:5100-5102.

Liu J, et al. Porous Nanoparticle Supported Lipid Bilayers (Protocells) as Delivery Vehicles. J Am Chem Soc, 2009;131:1354-1355.

Liu J, et al. Electrostatically Mediated Liposome Fusion and Lipid Exchange with a Nanoparticle-Supported Bilayer for Control of Surface Charge, Drug Containment, and Delivery. J Am Chem Soc, 2009;131:7567-7569.

Lu Y, et al. Aerosol-assisted self-assembly of mesostructured spherical nanoparticles. Nature, 1999;398:223-226.

Ashley CE, et al. The targeted delivery of multicomponent cargos to cancer cells by nanoporous particle-supported lipid bilayers. Nature Material, 2011;10:389-397.

Weis K. Erratum. Trends in Biochemical Sciences, 1998;23(7):235-236.

Weis K. Importins and exportins: how to get in and out of the nucleus. Trends in Biochemical Sciences, 1998;23 (5):185-189.

Cokol M, Nair R, Rost B. Finding nuclear localization signals. EMBO Reports, 2000;1(5):411-415.

Remington's Pharmaceutical Sciences. Mack Printing Company, 1985: Seventeenth Edition. Easton, Pennsylvania.

Ashley, Carlee E. et al.; The Targeted Delivery of Multicomponent Cargos to Cancer Cells by Nanoporous Particle-Supported Lipid Bilayers; Nature Materials, 2011; vol. 10, p. 389-397.

Online supplement to Ashley, Carlee E. et al.; The Targeted Delivery of Multicomponent Cargos to Cancer Cells by Nanoporous Particle-Supported Lipid Bilayers; Nature Materials, 2011; vol. 10, p. 389-397.

Ashley, Carlee E. et al.; Delivery of Small Interfering RNA by Peptide-Targeted Mesoporous Silica Nanoparticle-Supported Lipid Bilayers; ACS NANO; Feb. 6, 2012; vol. 6, pp. 2174-2188.

Buranda, Tione et al.; Biomimetic Molecular Assemblies on Glass and Mesoporous Silica Microbeads for Biotechnology; Langmuir; Jan. 17, 2003; vol. 19, pp. 1654-1663.

Chemburu, S. et al.; Biomimetic Silica Microspheres in Biosensing; Molecules; 2010; vol. 15, pp. 1932-1957.

Fishkis, Maya; Steps Towards the Formation of a Protocell: The Possible Role of Short Peptides; Origins of Life and Evolution of Biospheres; Sep. 14, 2007; vol. 37, pp. 537-553.

Giamalva, DH et al.; Effect of Bilayer Structure on the Rates of Reaction of Ozone with Polyunsaturated Fatty Acids in Phosphatidylcholine Liposomes; Chemical Research in Toxicology; 1988, vol. 1, pp. 144-145.

Green, AE et al.; Pegylated Liposomal Doxorubicin in Ovarian Cancer; International Journal of Nanomedicine; 2006; vol. 1, pp. 229-239.

Hawkins MJ, et al; Protein Nanoparticles as Drug Carriers in Clinical Medicine; Advanced Drug Delivery Reviews; 2008; vol. 60, pp. 876-885.

Hicks, Randall W. et al.; Nanoparticle Assembly of Mesoporous AlOOH (Boehmite); Chemistry of Materials; 2003; vol. 15, pp. 78-82.

Irvine, Darrell J.; One Nanoparticle, One Kill; Nature Materials; Apr. 17, 2011; vol. 10, pp. 342-343.

Kendall et al., A New Class of Supported Lipid Bilayers: Lipid Coated Porous Silica Microspheres, (Abstract); 237th ACS National Meeting; Mar. 22-26, 2009.

Li, Zongxi et al.; Mesoporous Silica Nanoparticles in Biomedical Applications; Chemical Society Reviews; 2012; vol. 41, pp. 2590-2605.

Liu, Juewen et al.; New Advances in Ovarian Cancer; Oncology; Jul. 15, 2010; vol. 24, pp. 721-728.

Parikh, AN; Membrane-Substrate Interface: Phospholipid Bilayers at Chemically and Topographically Structured Surfaces; Biointerphases; 2008; vol. 3, FA22.

Piura B. et al.; Autoantibodies to Tumor-Associated Antigens in Epithelial Ovarian Carcinoma; Journal of Oncology; 2009; Article ID 581939, 11 pages.

Piyasena, ME et al.; Biosensors Based on Release of Compounds upon Disruption of Lipid Bilayers Supported on Porous Microspheres; Biointerphases; 2008; vol. 3, pp. 38-49.

Porotto, Matteo et al.; Synthetic Protocells Interact with Viral Nanomachinery and Inactivate Pathogenic Human Virus; PLOS ONE; Mar. 1, 2011; vol. 5, pp. 1-9.

Rosenholm, Jessica M. et al.; Towards Multifunctional, Targeted Drug Delivery Systems Using Mesoporous Silica Nanoparticles—Opportunities & Challenges; Nanoscale; Aug. 23, 2010; vol. 2, pp. 1870-1853.

Slowing, Igor I. et al.; Mesoporous Silica Nanoparticles as Controlled Release Drug Delivery and Gene Transfection Carriers; Advanced Drug Delivery Reviews; Aug. 17, 2008; vol. 60, pp. 1278-1288.

Toutier, A.L., et al; An Overview of Lipid Membrane Supported by Colloidal Particles; Advanced Colloidal Interface Science; 2007; vol. 133, pp. 1-21.

Trafton, Anne; Nanoparticles Target Ovarian Cancer; MIT News Office; Jul. 30, 2009, at http://newsoffice.mit.edu/2009/ovarian-0730.

Zeineldin, R.; et al.; Epithelial Cell Migration in Response to Epidermal Growth Factor; Methods in Molecular Biology; 2006; p. 327, pp. 147-158.

Zelphati, Olivier et al.; Mechanism of Oligonucleotide Release from Cationic Liposomes; Proceedings of the National Academy of Science; Oct. Apr. 7, 1996; vol. 93, pp. 11493-11498.

Porotto M, et al. Synthetic protocells interact with viral nanomachinery and inactivate pathogenic human virus. PLOS ONE, 2011;6(3):e16874.

Gen News Highlights. Scientists Develop High-Capacity Nanoparticles for Targeted Delivery of Drug Cocktails. Genetic Engineering & Biotechnology News, 2011 http://www.genengnews.com/gen-news-highlights/scientists-develop-high-capacity-nanoparticles-for-targeted-delivery-of-drug-cocktails/81245016/.

Ashley CE. Development of Novel Bio/Nano Interfaces Formaterials Science and Biomedical Applications. May 2010, ProQuest LLC, USA.

Kim EM, et al. Iodine 125-labeled mesenchymal epithelial transition factor binding peptide-click-cRGDyk heterodimer for glioma imaging. Cancer Science, 2010;102(8):1516-1521.

Epler K, et al. Delivery of ricin toxin a-chain by peptide-targeted mesoporous silica nanoparticle-supported lipid bilayers. Advanced Health Care Materials, 2012;1(3):348-353.

(56) References Cited

OTHER PUBLICATIONS

"U.S. Appl. No. 14/970,998, Preliminary Amendment filed Dec. 16, 2015", 3 pgs.

"U.S. Appl. No. 14/970,998, Preliminary Amendment filed Dec. 28, 2015", 13 pgs.

"Australian U.S. Appl. No. 2012249474, First Examiner Report mailed Jul. 20, 2016", 4 pgs.

"Chinese Application Serial No. 201280031496.8, Decision on Rejection mailed Jun. 7, 2016", (English Translation), 9 pgs.

"European Application Serial No. 12776480.1, Extended European Search Report mailed Oct. 9, 2014", 8 pgs.

"European Application Serial No. 12776480.1, Response filed May 5, 2015 to Office Action mailed Oct. 28, 2014", 10 pgs.

"International Application Serial No. PCT/US2012/035529, International Preliminary Report on Patentability mailed Nov. 7, 2013", 8 pgs.

"International Application Serial No. PCT/US2012/035529, International Search Report mailed Oct. 23, 2012", 5 pgs.

"International Application Serial No. PCT/US2012/035529, Written Opinion mailed Oct. 23, 2012", 8 pgs.

"Japanese Application Serial No. 2014-508125, Office Action mailed Feb. 15, 2016", (w/ English Translation), 9 pgs.

Butler, Kimberly, et al., "Protocells: Modular Mesoporous Silica Nanoparticle-Supported Lipid Bilayers for Drug Delivery", *Small* 12, No. 16, (2016), 2173-2185.

Dengler, Ellen C., et al., "Mesoporous silica-supported lipid bilayers (protocells) for DAN cargo delivery to the spinal cord", Journal of Controlled Release 168, (2013), 209-224.

Liu, Juewen, et al., "Porous Nanoparticle Supported Lipid Bilayers (Protocells) as Delivery Vehicles", *HIH Public Access, Published in final form as: J. Am. Chem. Soc.*, vol. 131, No. 4, 1354-1355, (2009), 7 pgs.

Liu, Xiangsheng, et al., "Irinotecan Delivery by Lipid-Coated Mesoporous Silica Nanoparticles Shows Improved Efficacy and Safety over Liposomes for Pancreatic Cancer", *ACS Nano* 10, (2016), 2702-2715.

Meng, Huan, et al., "Use of a Lipid-Coated Mesoporous Silica Nanoparticle Platform for Synergistic Gemcitabine and Paclitaxel Delivery to Human Pancreatic in Mice", *ACS Nano*, vol. 9, No. 4, (2015), 3540-3557.

\* cited by examiner

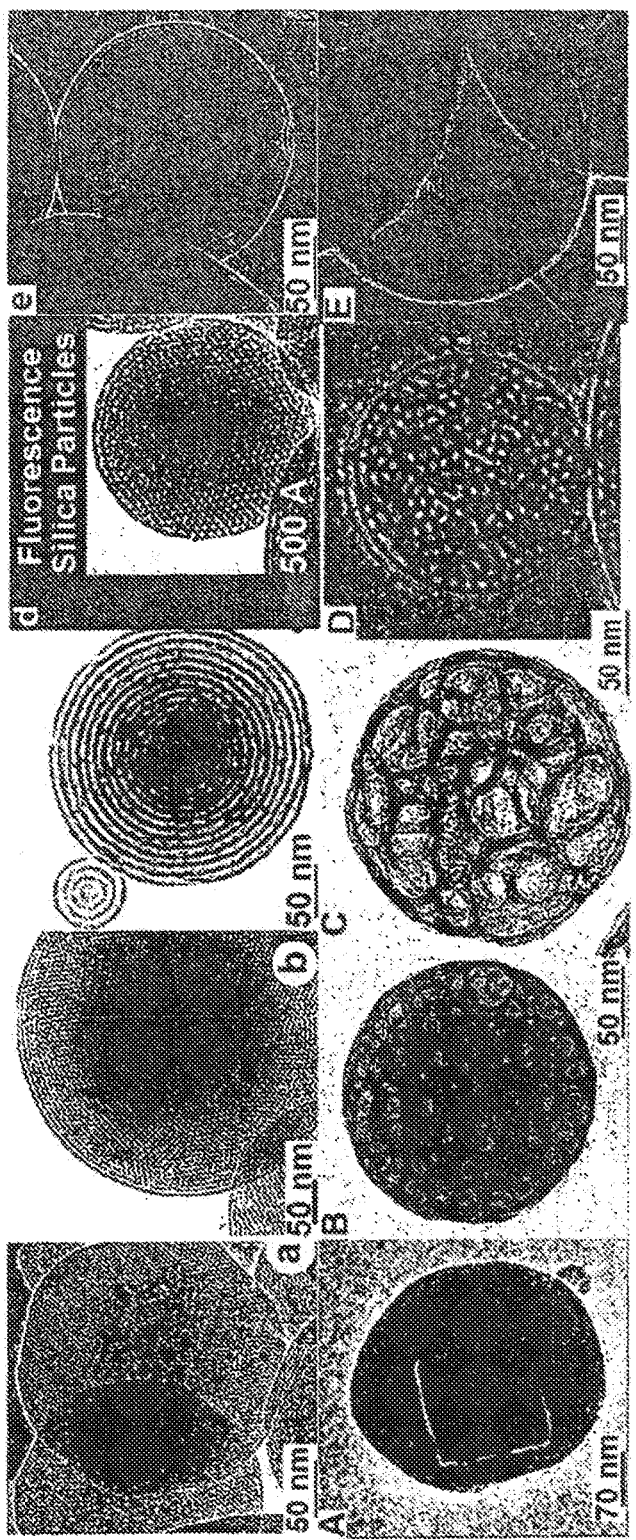

FIGURE 2B

| Nanopore Templates | BET surface area, m2/g | BJH pore diameter, nm | Pore volume, cc/g |
|---|---|---|---|
| CTAB | 1256 | 1.8 | 0.588 |
| Brij 56 | 514 | 4.1 | 0.557 |
| F108+ Urea (55%wt) | 1177 | 4.41 | 0.943 |
| F108+ Urea (40%wt) | 506 | 5.39 | 0.48 |
| P123 + PPO(MW425) | 323 | 6.5 | 0.53 |
| F108 | 505 | 6.53 | 0.7 |
| F108 + 19 nm PS | 333 | 10.93 | 0.676 |
| P123 +3.4% PPGA | 190 | 12.7 | 0.60 |
| F108 + glycerol monooleate+Urea | 262 | 14.63 | 0.649 |
| Microemulsion | 100 | Bimodal 5, 10-30nm | 1.1 |

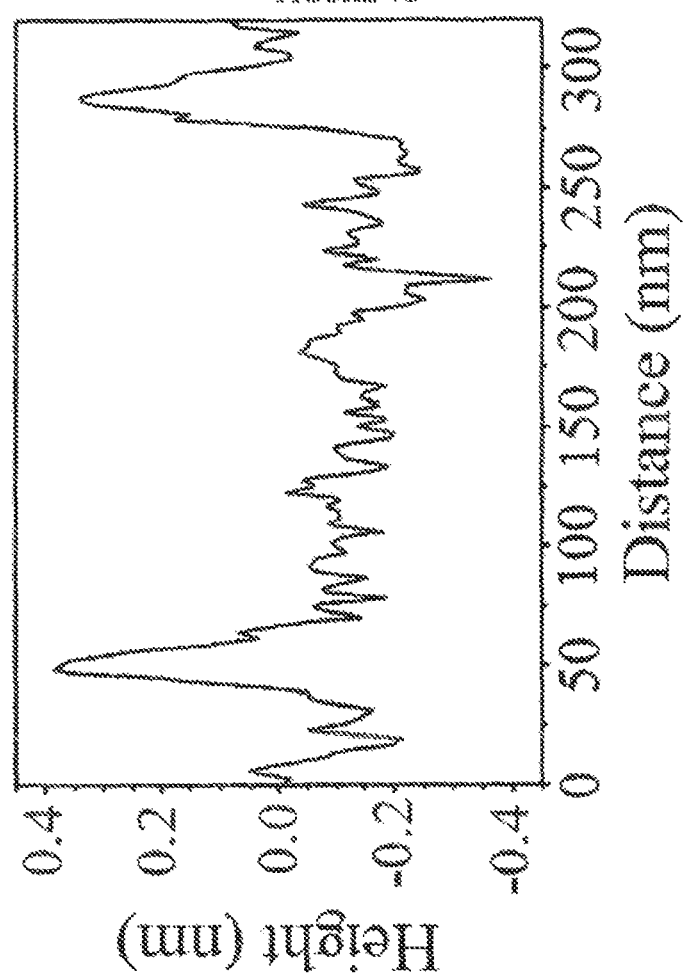

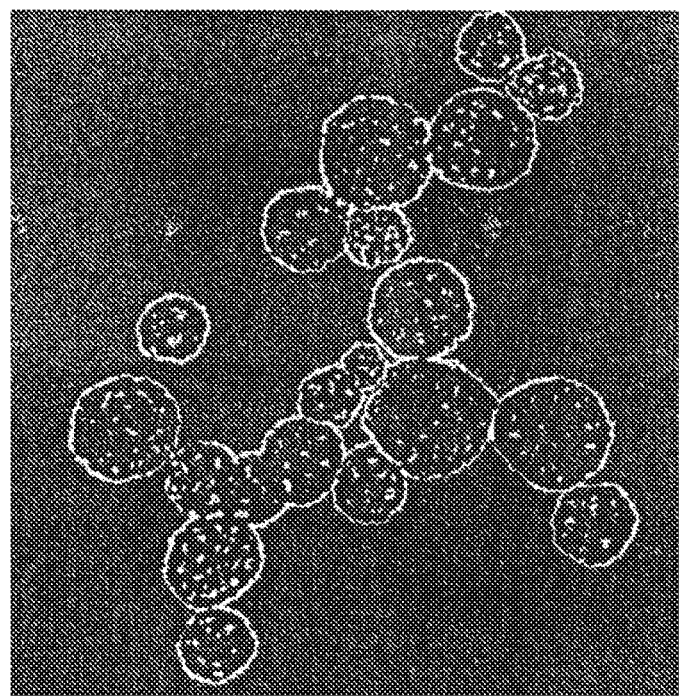

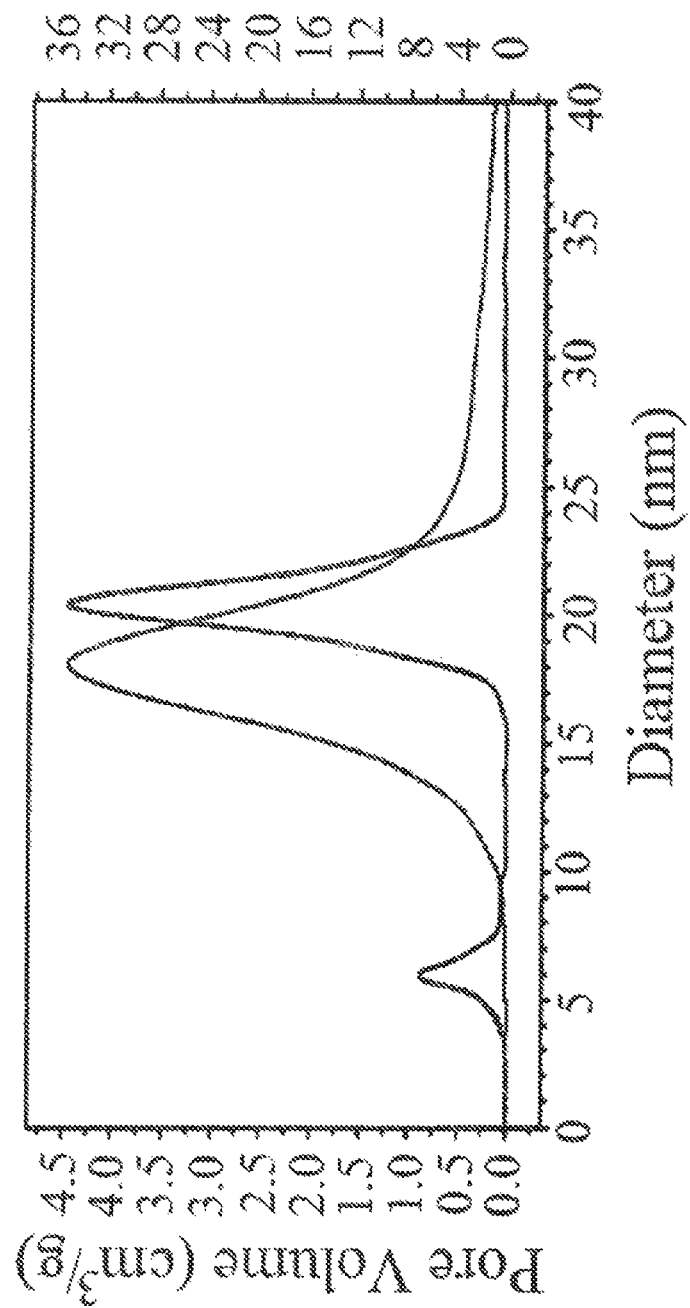

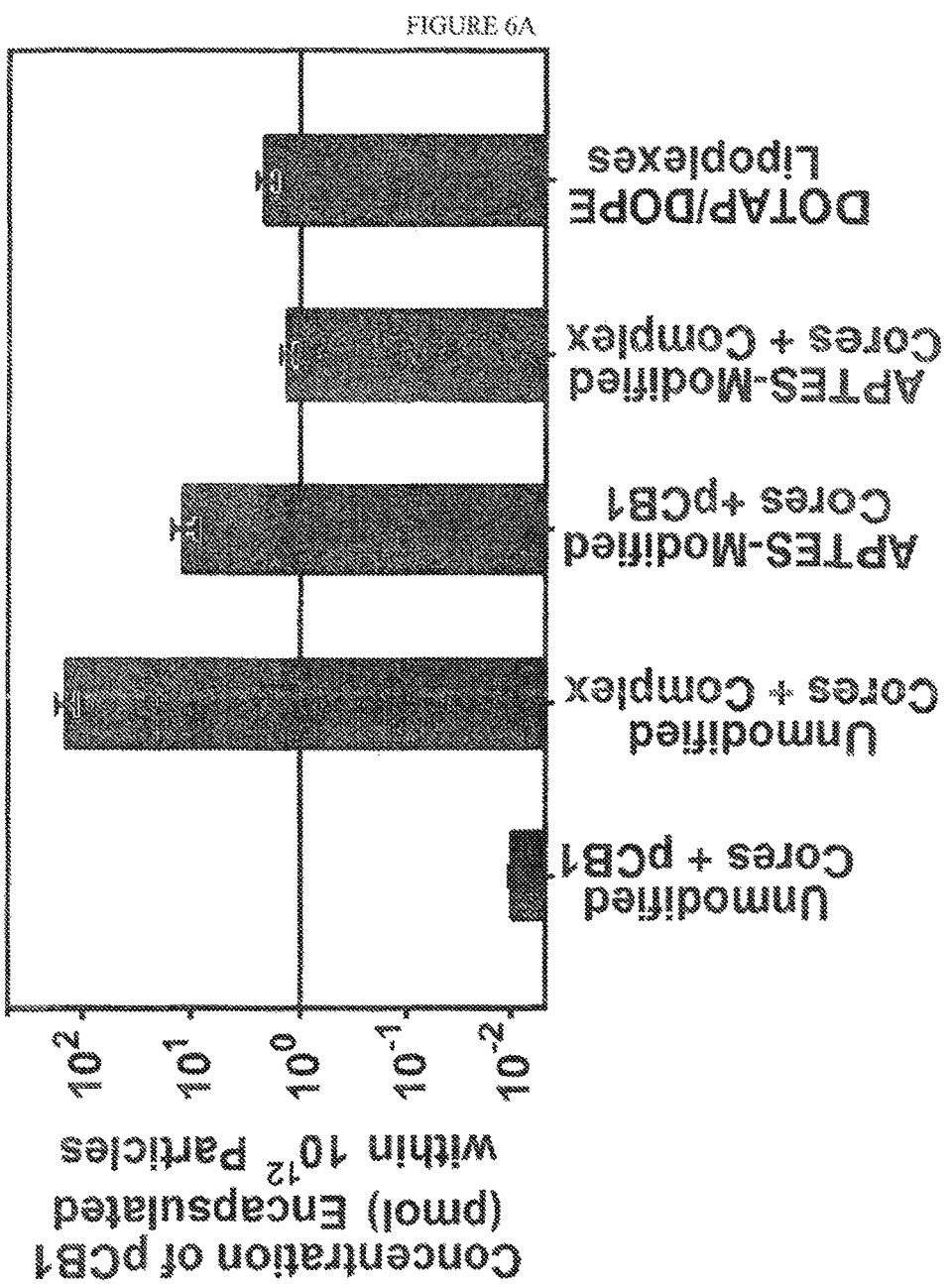

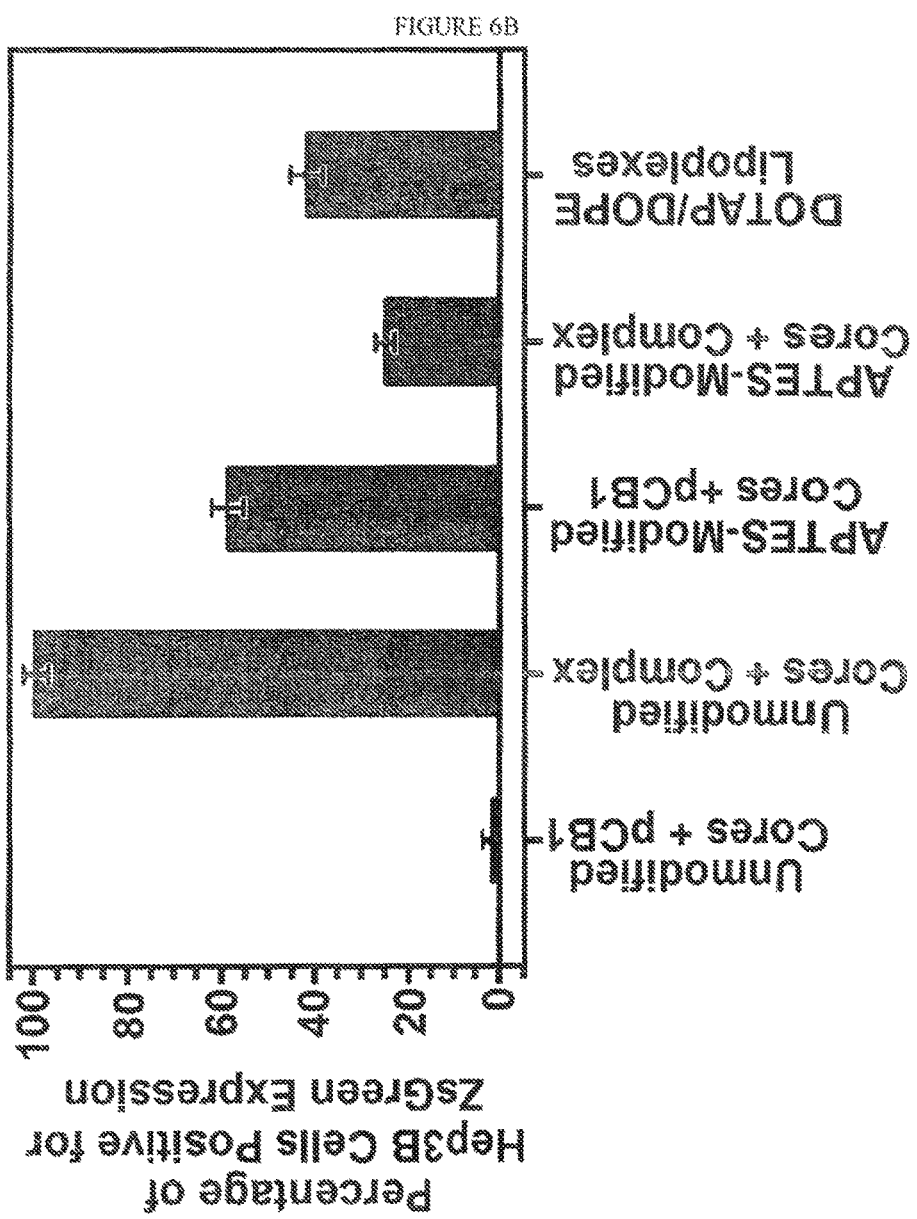

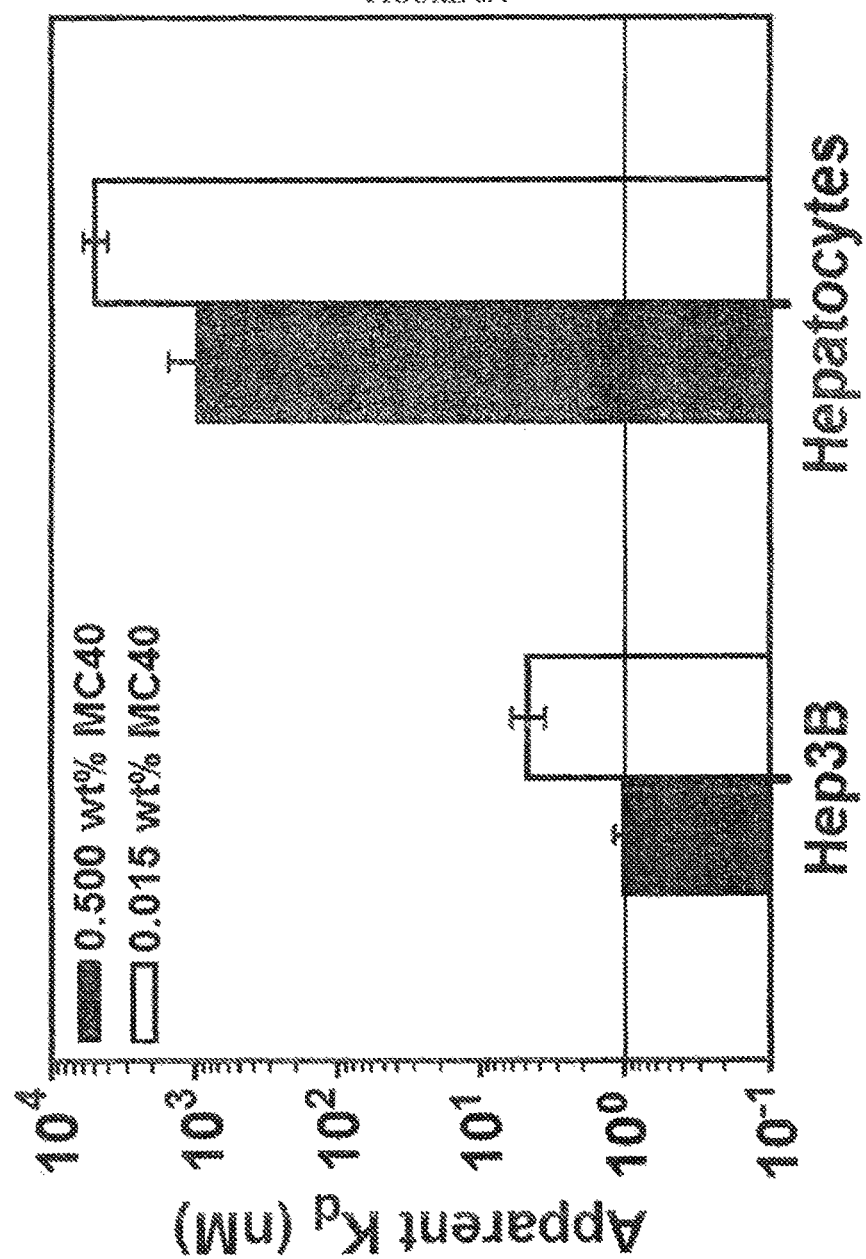

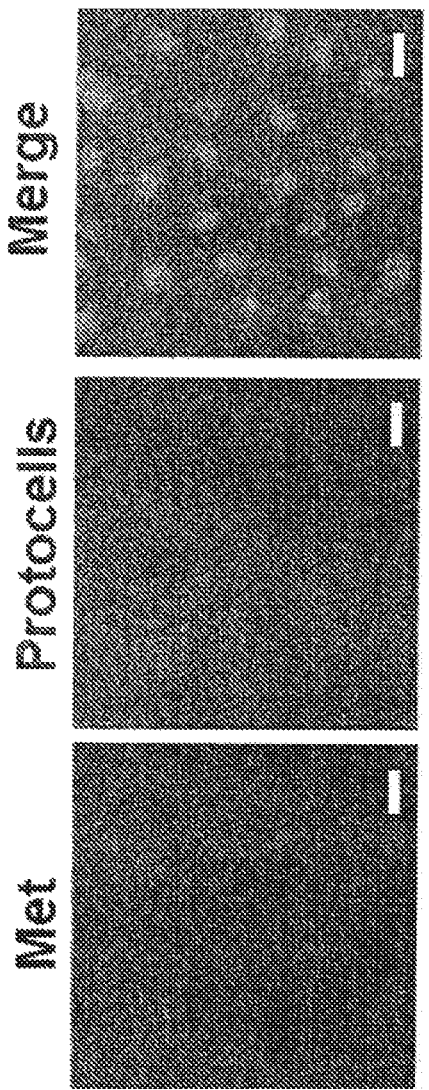

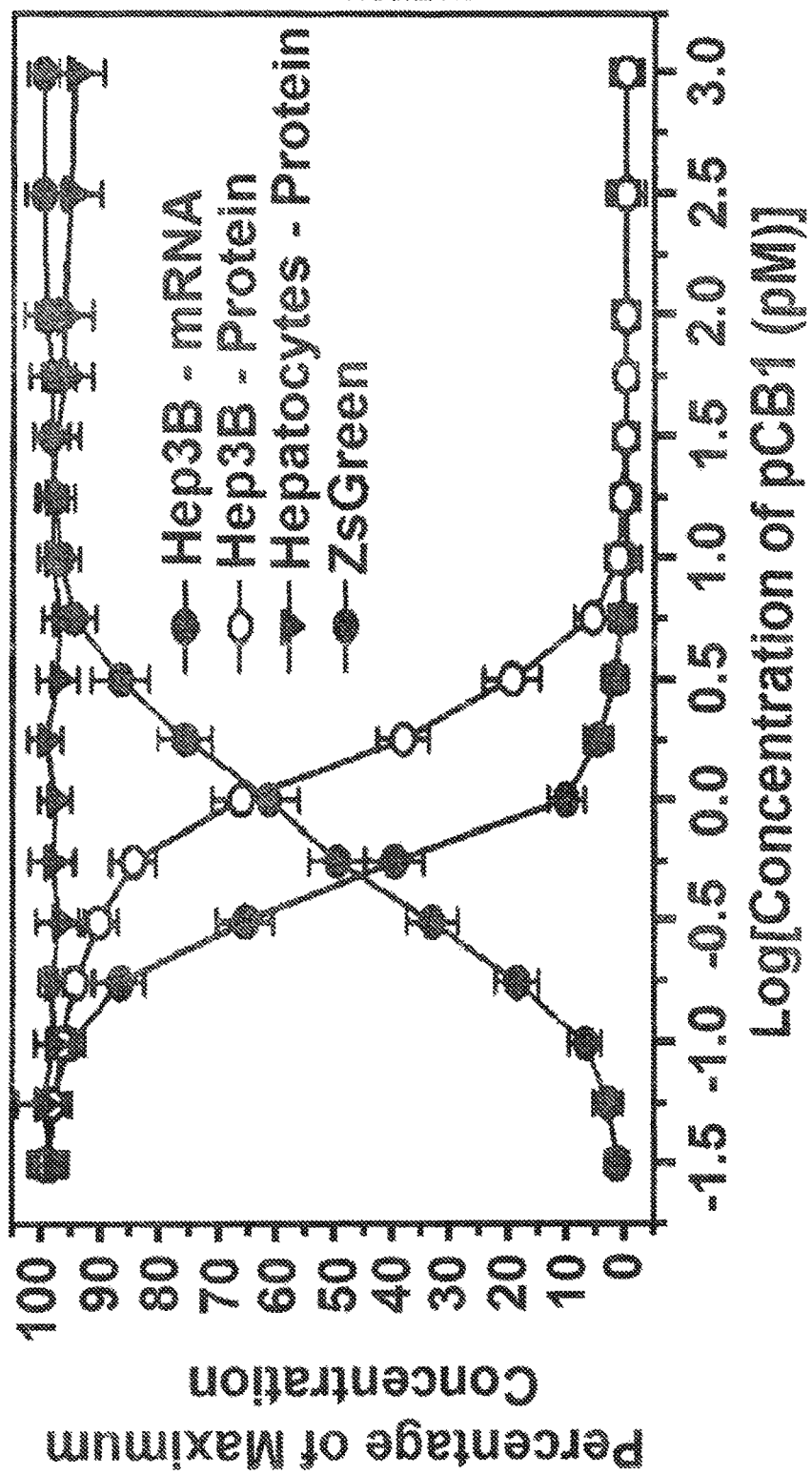

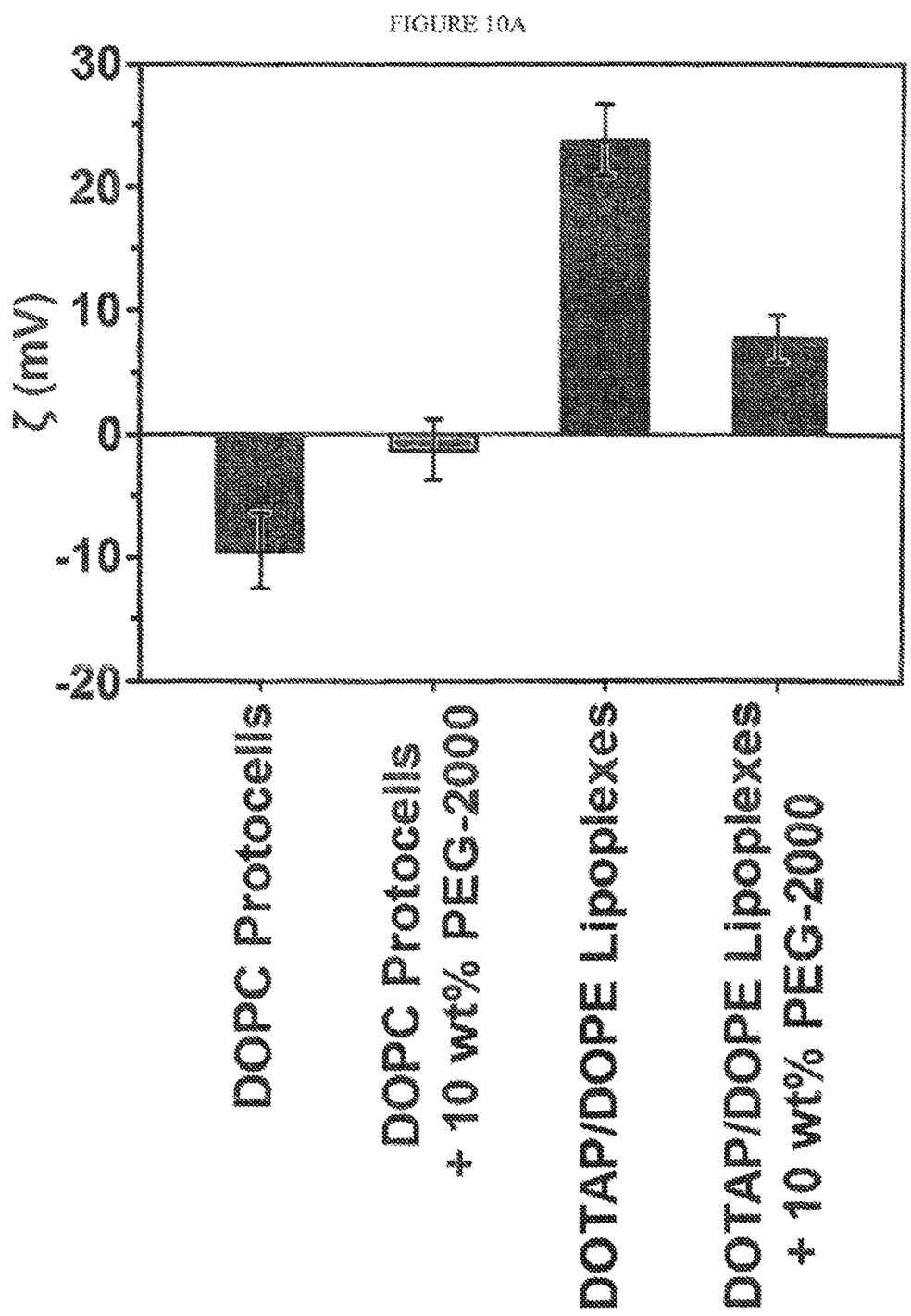

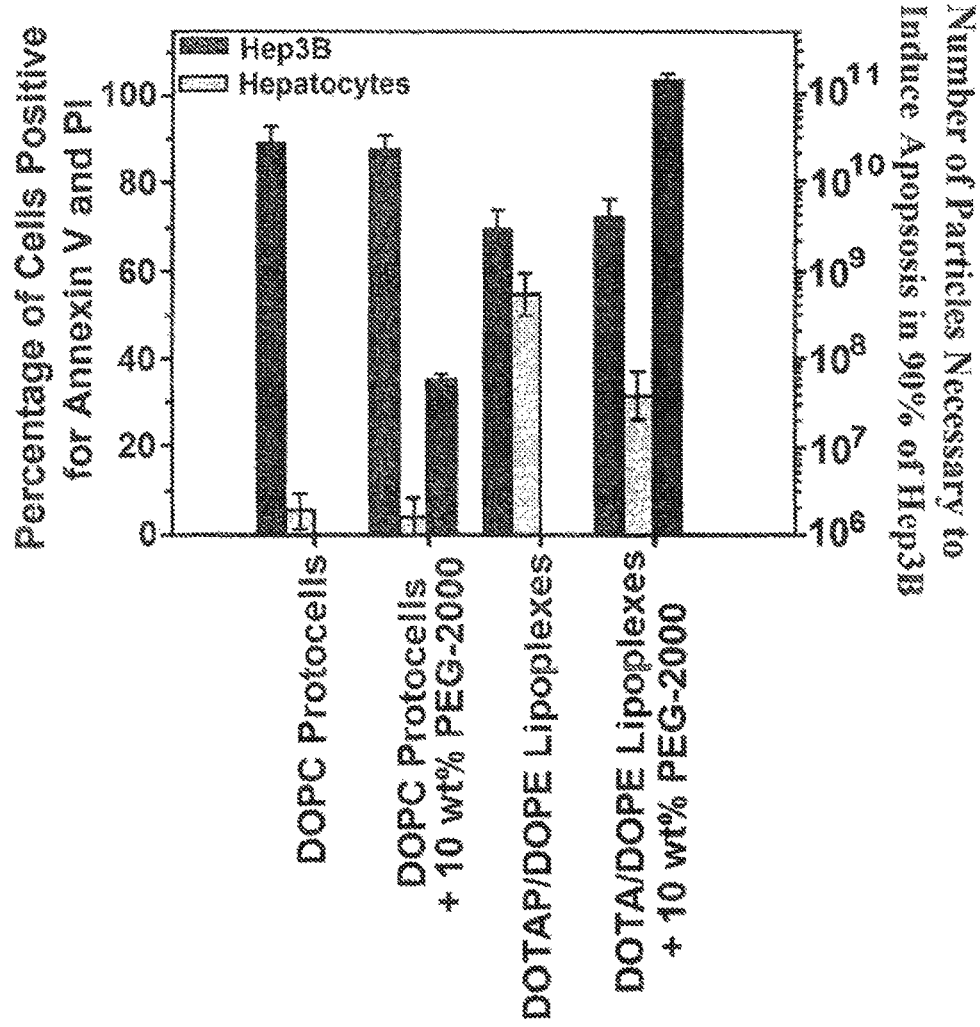

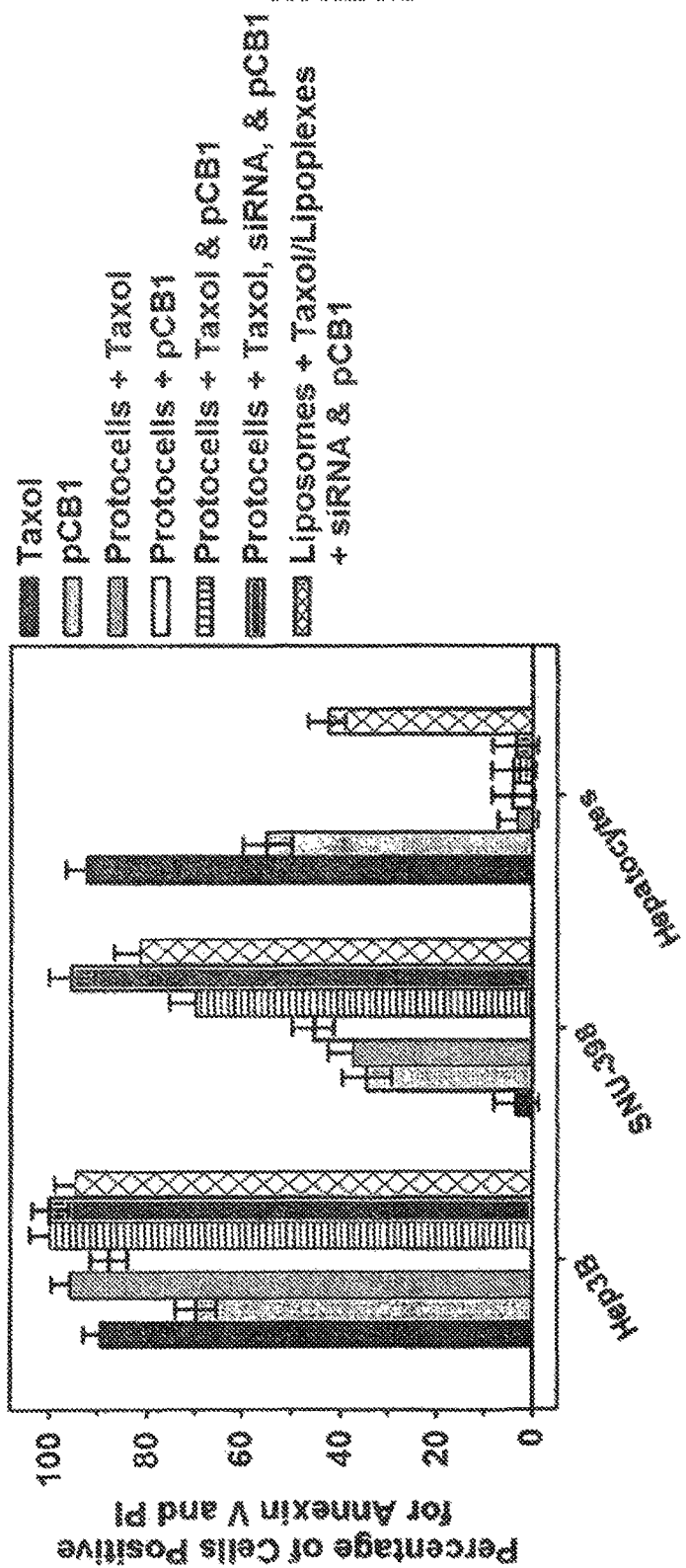

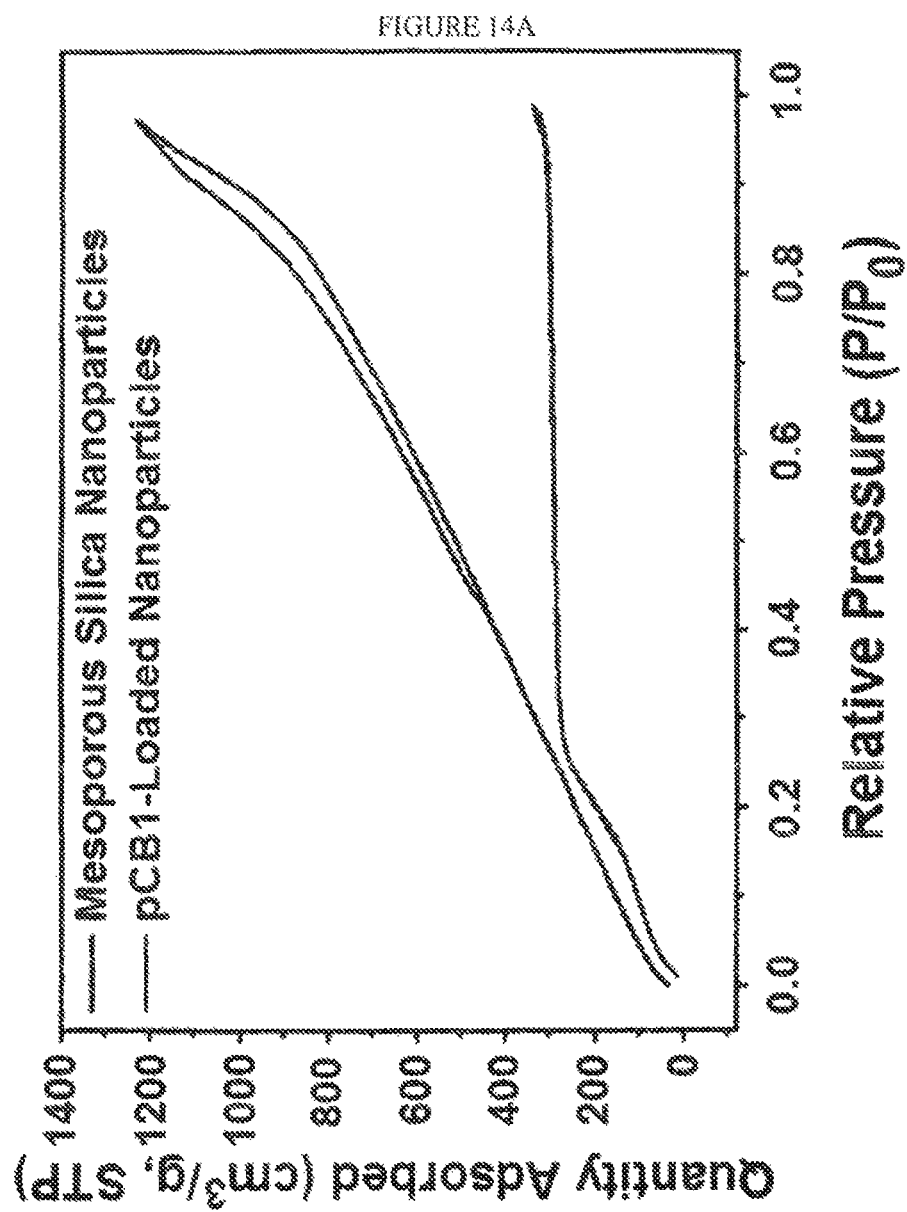

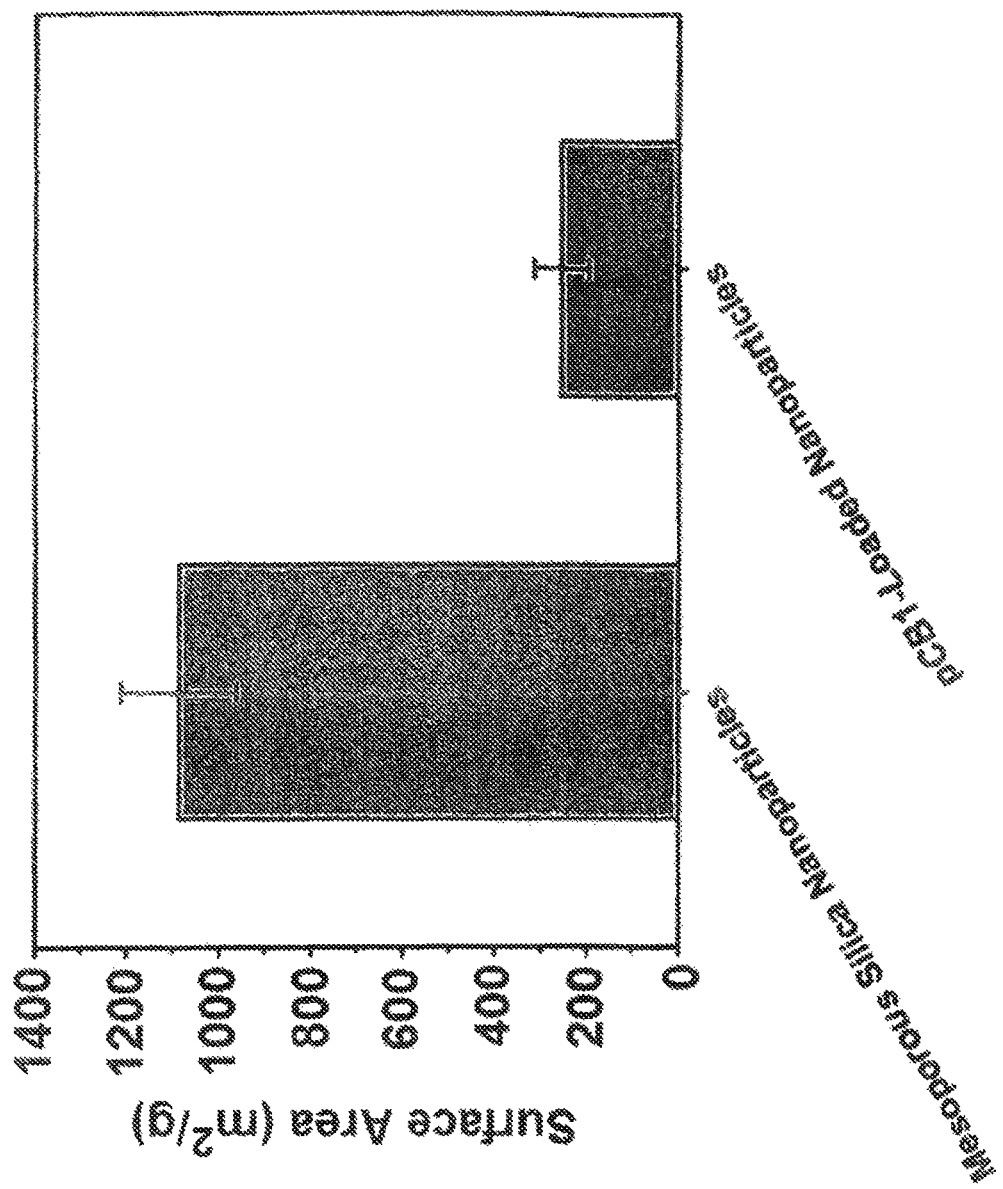

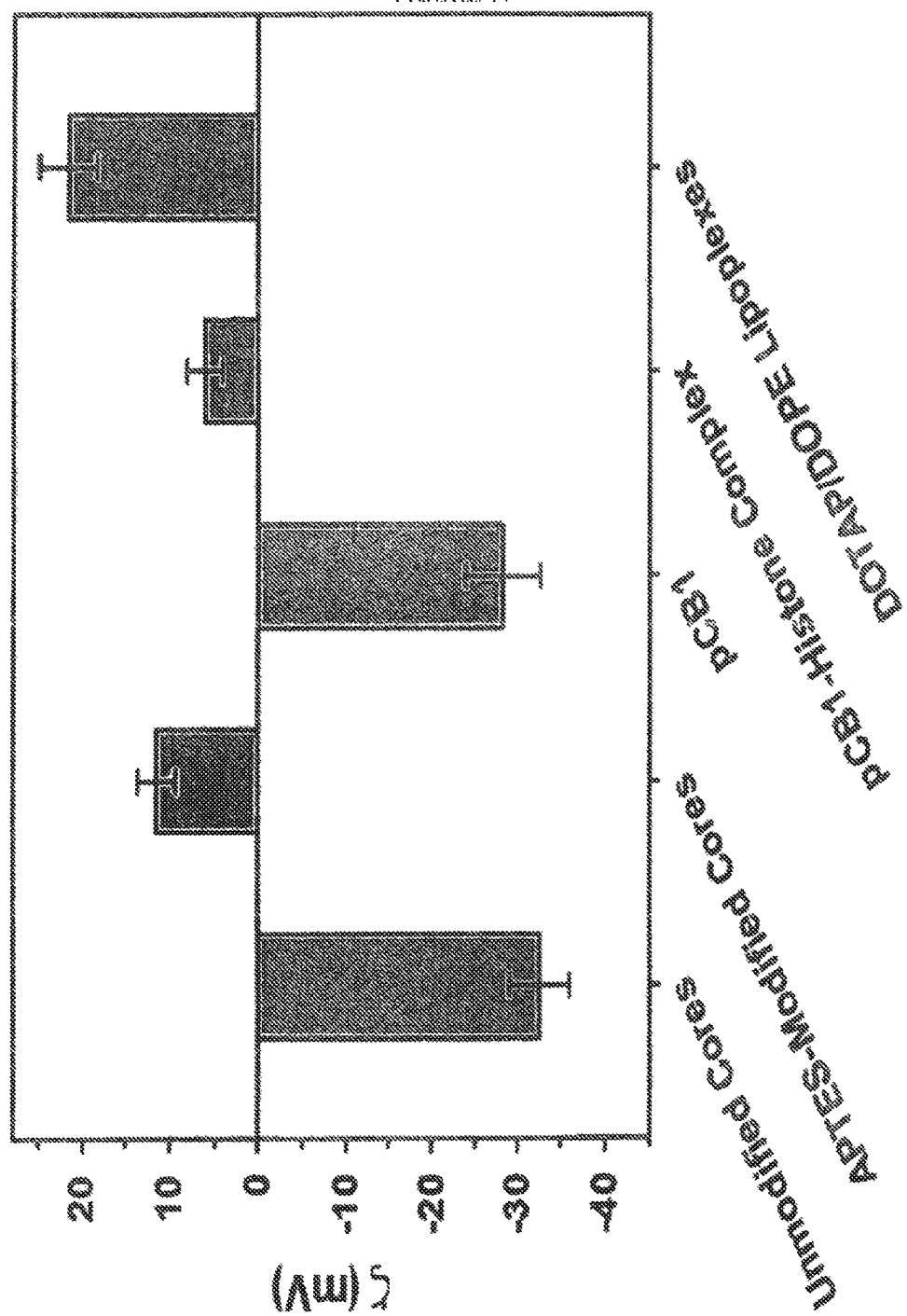

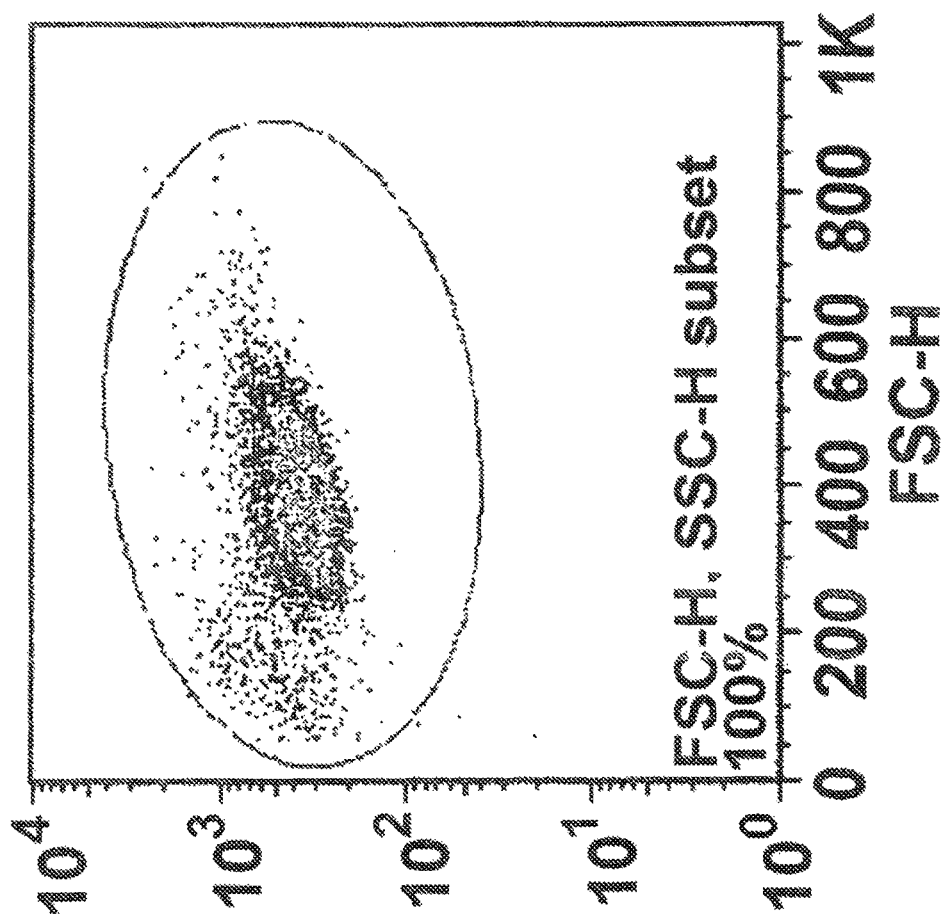

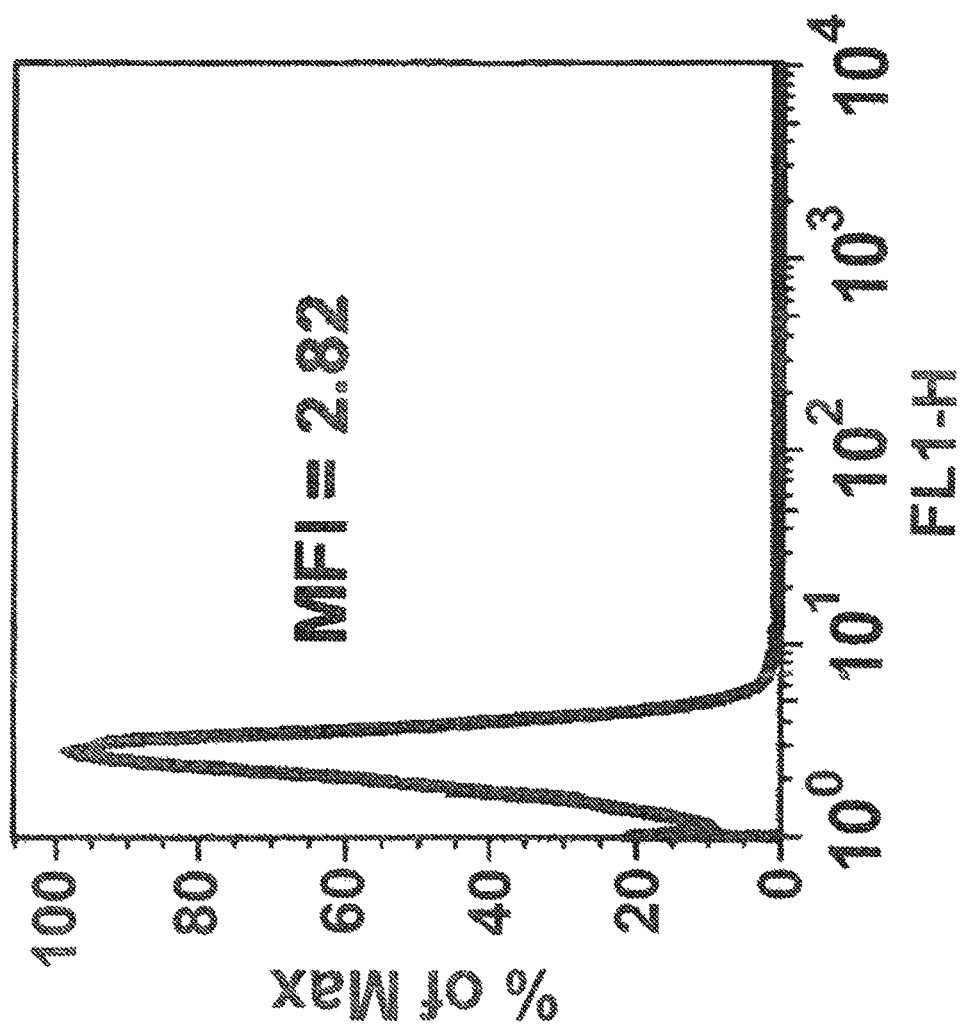

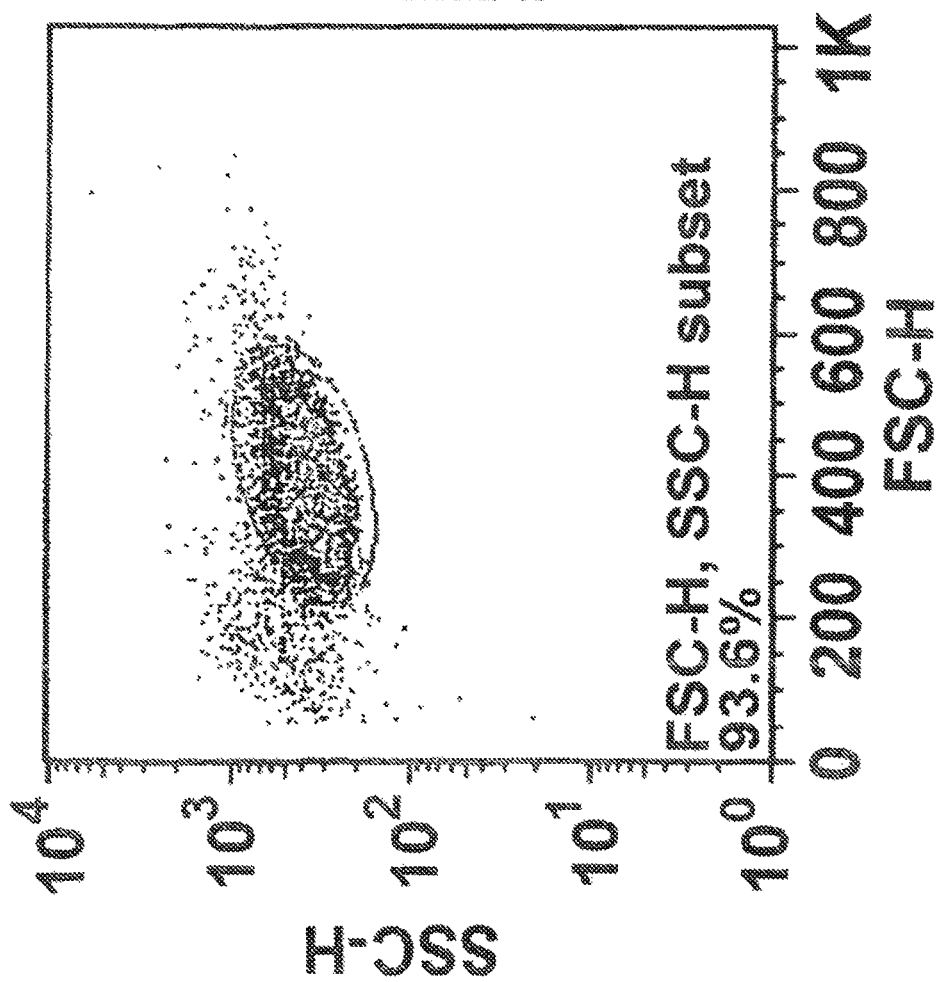

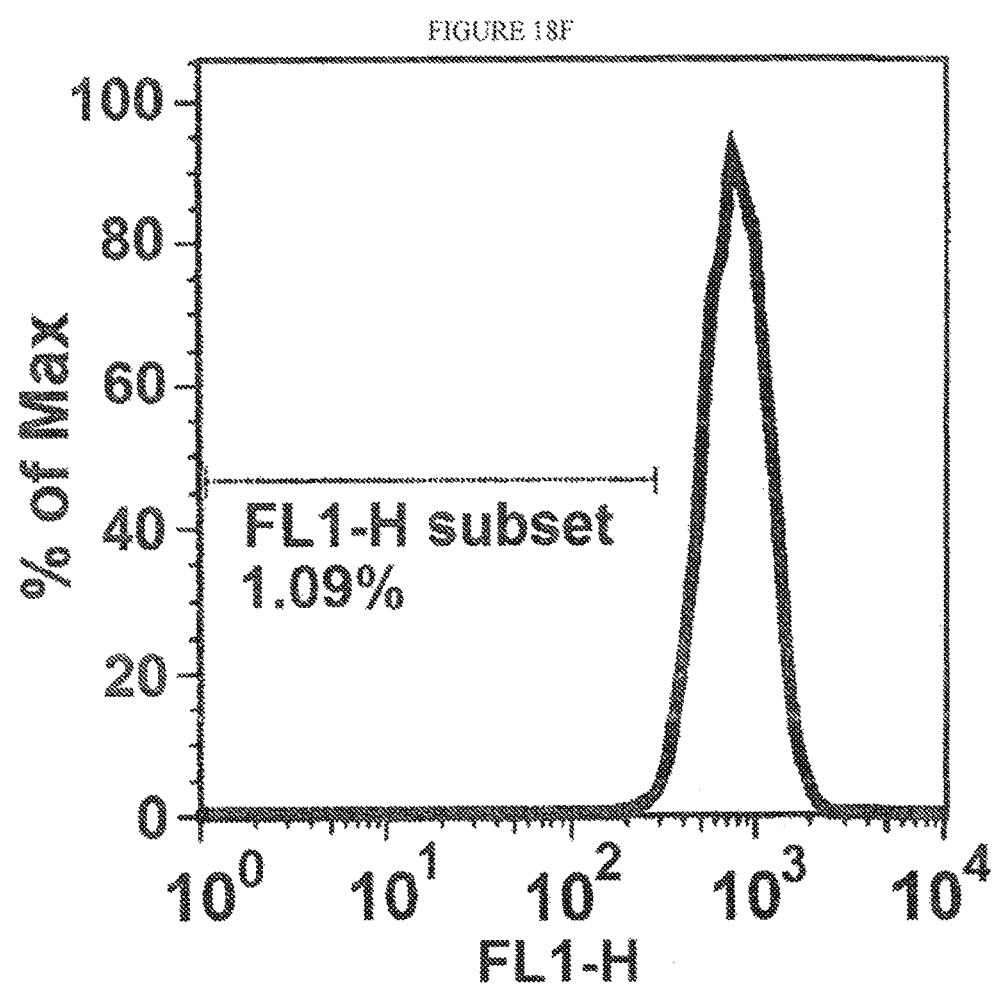

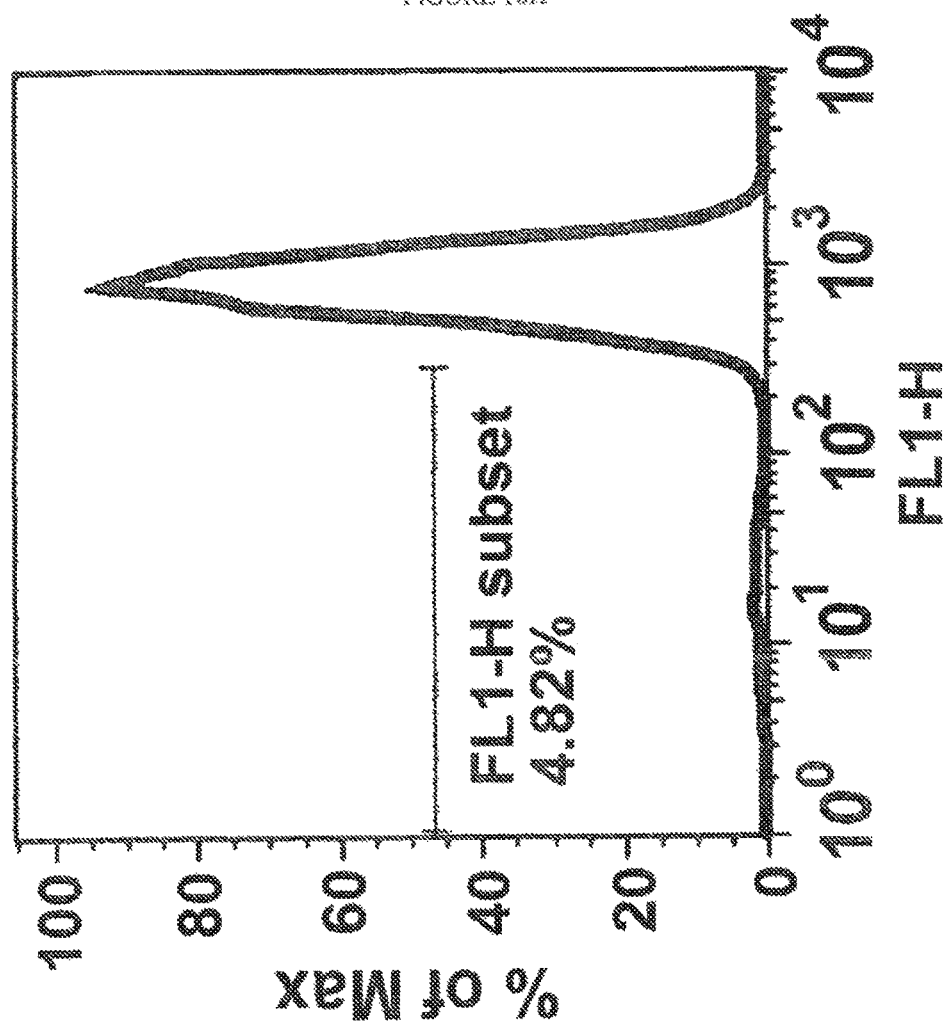

FIGURE 20A

| | | | |
|---|---|---|---|
| MC37 | --ASVHFPP | MC6 | --ASVHFPP |
| MC40 | --ASVHFPP | MC5 | --ASVHFPP |
| MC36 | --ASVHFPP | MC4 | --ASVHFPP |
| MC34 | --ASVHFPP | MC3 | --ASVHFPP |
| MC30 | --ASVHFPP | MC16 | -TATFWFQ- |
| MC29 | --ASVHFPP | MC19 | -TATFWFQ- |
| MC28 | --ASVHFPP | MC23 | -TATFWFQ- |
| MC25 | --ASVHFPP | MC27 | -TATFWFQ- |
| MC24 | --ASVHFPP | MC8 | -TATFWFQ- |
| MC21 | --ASVHFPP | MC15 | -TATFWFQ- |
| MC20 | --ASVHFPP | MC17 | -TATFWFQ- |
| MC18 | --ASVHFPP | MC22 | -TATFWFQ- |
| MC14 | --ASVHFPP | MC31 | -TATFWFQ- |
| MC13 | --ASVHFPP | MC39 | -TATFWFQ- |
| MC12 | --ASVHFPP | MC2 | -FSAHAHL- |
| MC10 | --ASVHFPP | MC1 | GNTPSRA-- |
| MC9 | --ASVHFPP | MC11 | GNTPSRA-- |
| MC7 | --ASVHFPP | MC26 | GNTPSRA-- |

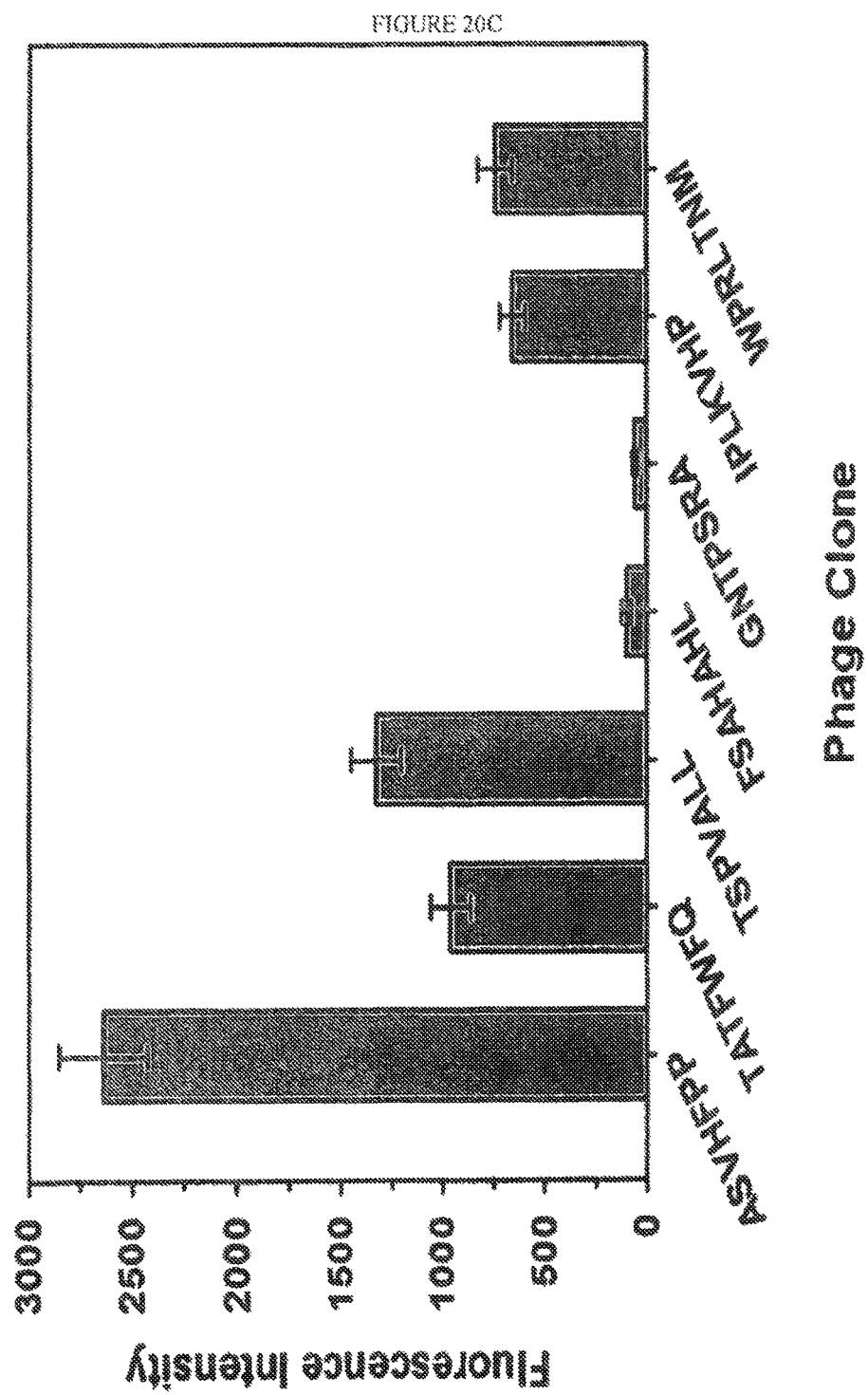

FIGURE 20D

| | | | |
|---|---|---|---|
| MC3 | -ASVHFPP | MC14 | -ASVHFPP |
| MC4 | -ASVHFPP | MC13 | -ASVHFPP |
| MC5 | -ASVHFPP | MC12 | -ASVHFPP |
| MC6 | -ASVHFPP | MC10 | -ASVHFPP |
| MC7 | -ASVHFPP | MC9 | -ASVHFPP |
| MC37 | -ASVHFPP | MC16 | TATFWFQ- |
| MC40 | -ASVHFPP | MC19 | TATFWFQ- |
| MC36 | -ASVHFPP | MC23 | TATFWFQ- |
| MC34 | -ASVHFPP | MC27 | TATFWFQ- |
| MC30 | -ASVHFPP | MC8 | TSPVALL- |
| MC29 | -ASVHFPP | MC15 | TSPVALL- |
| MC28 | -ASVHFPP | MC17 | TSPVALL- |
| MC25 | -ASVHFPP | MC22 | TSPVALL- |
| MC24 | -ASVHFPP | MC31 | TSPVALL- |
| MC21 | -ASVHFPP | MC39 | TSPVALL- |
| MC20 | -ASVHFPP | MC33 | -IPLKVHP |
| MC18 | -ASVHFPP | MC35 | WPRLTNM- |

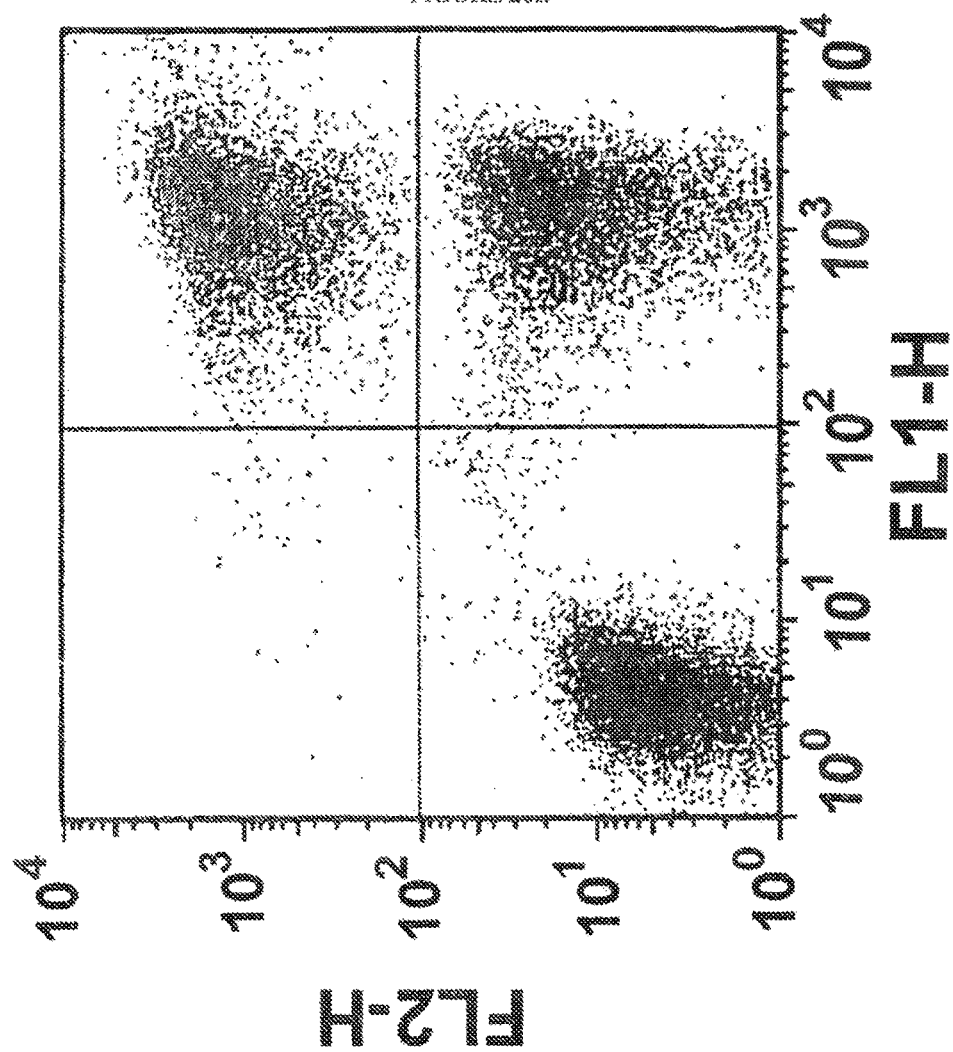

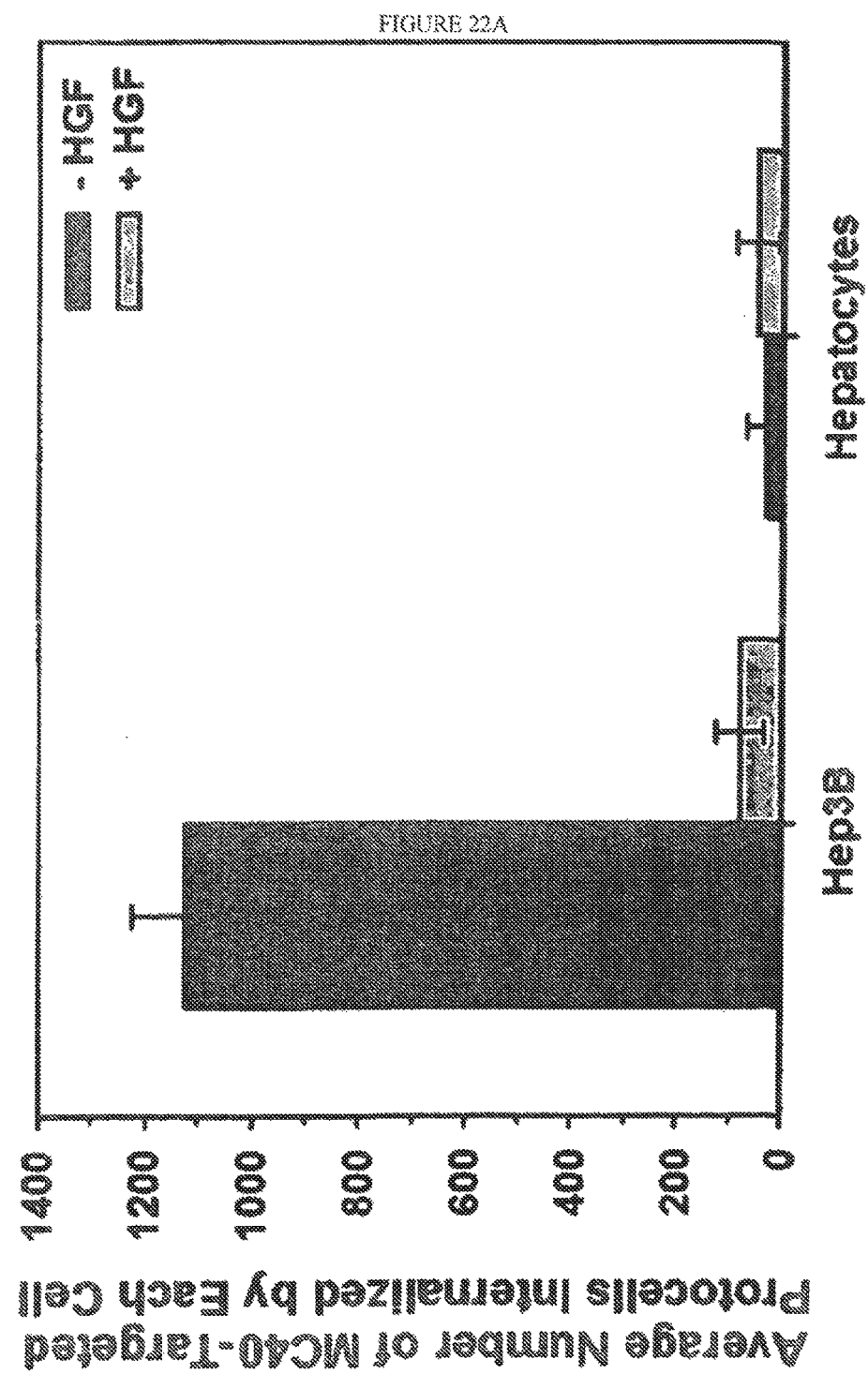

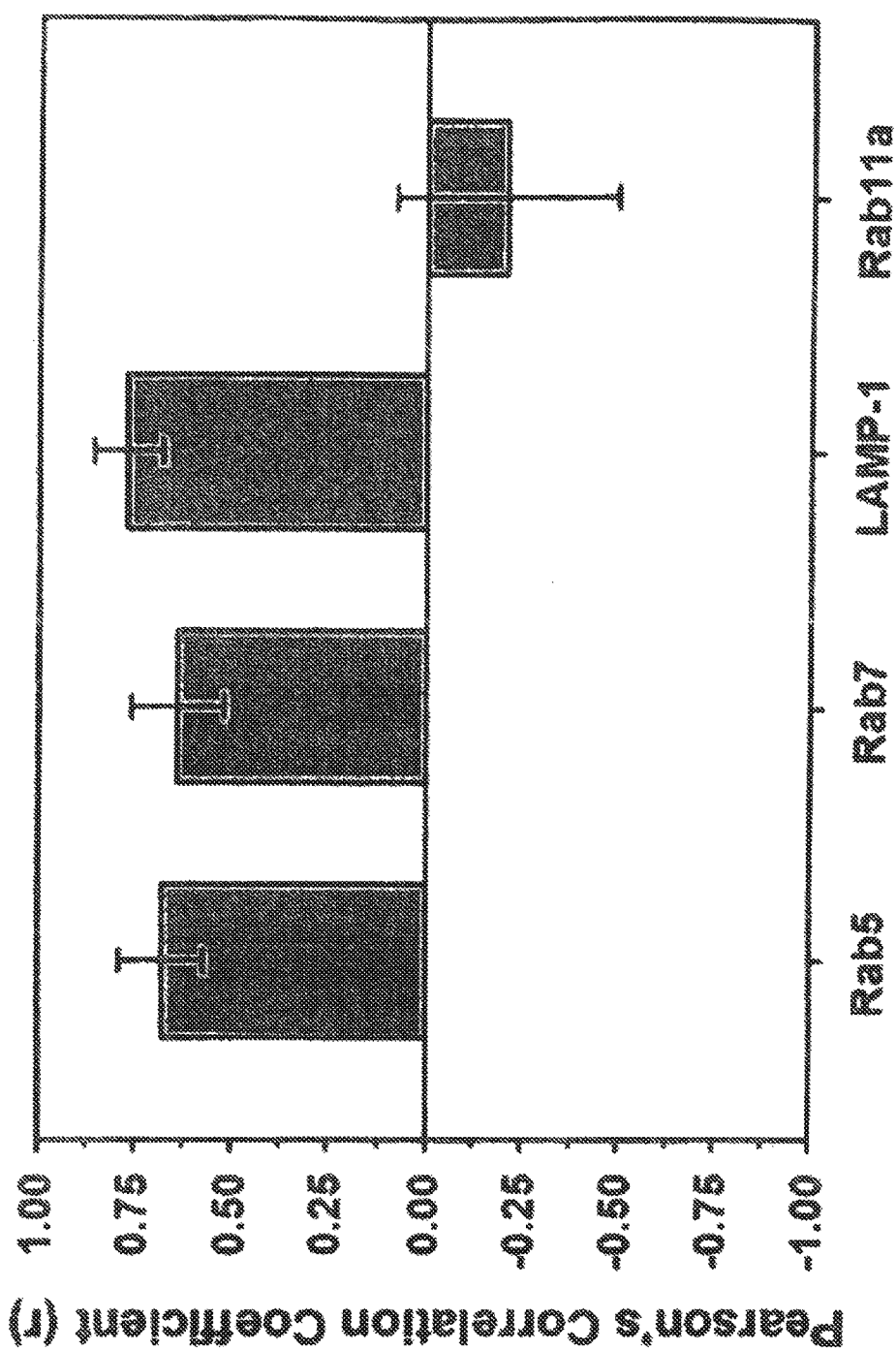

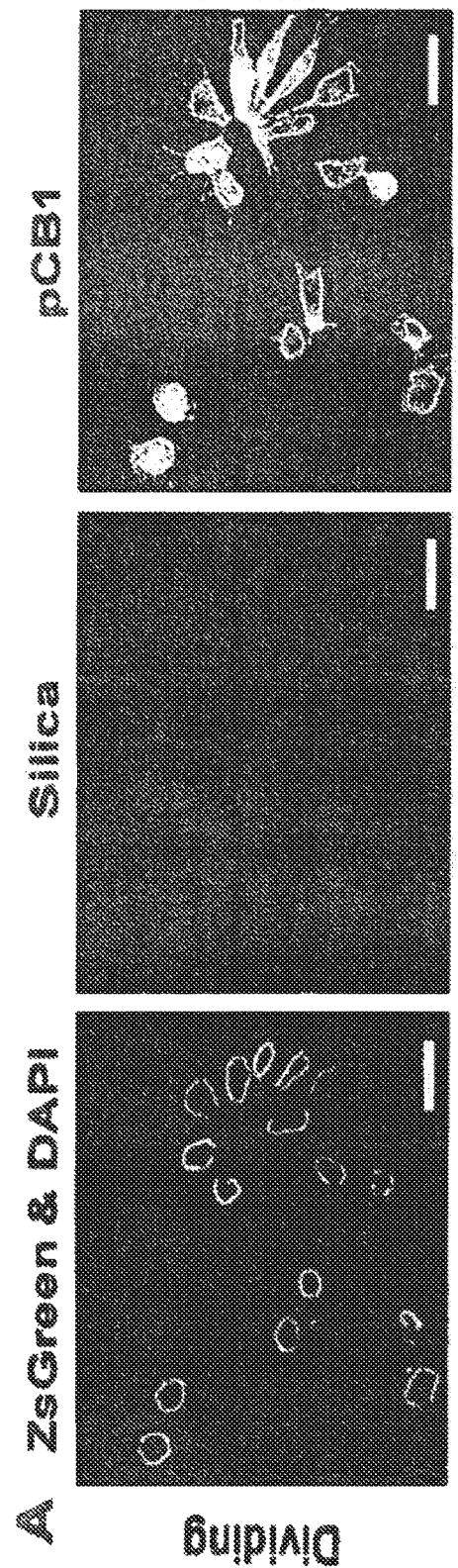

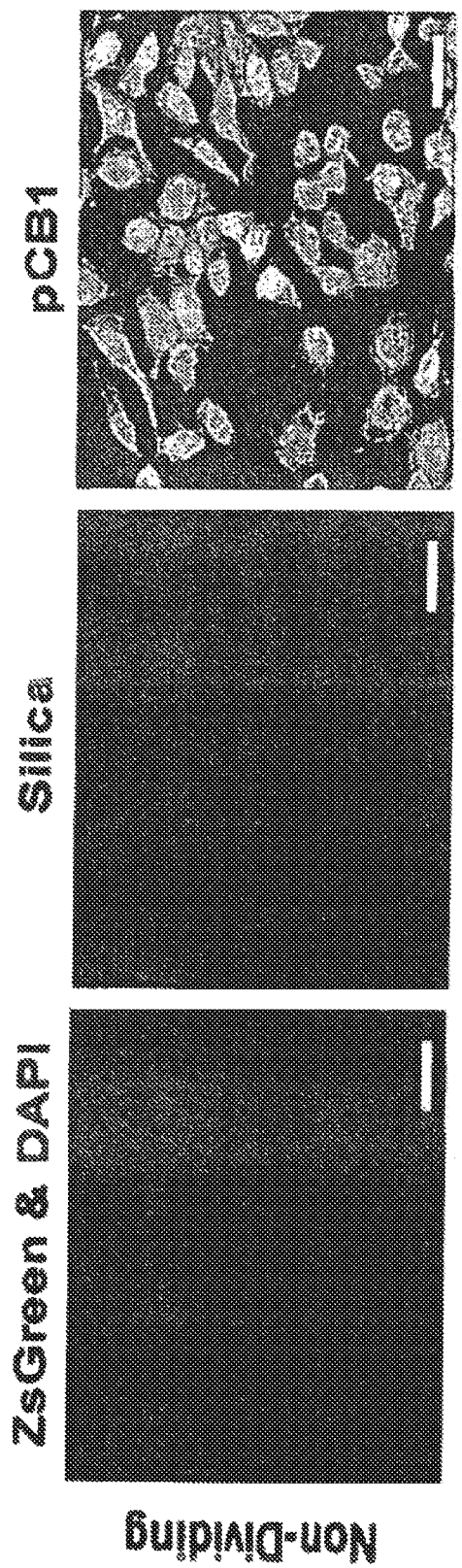

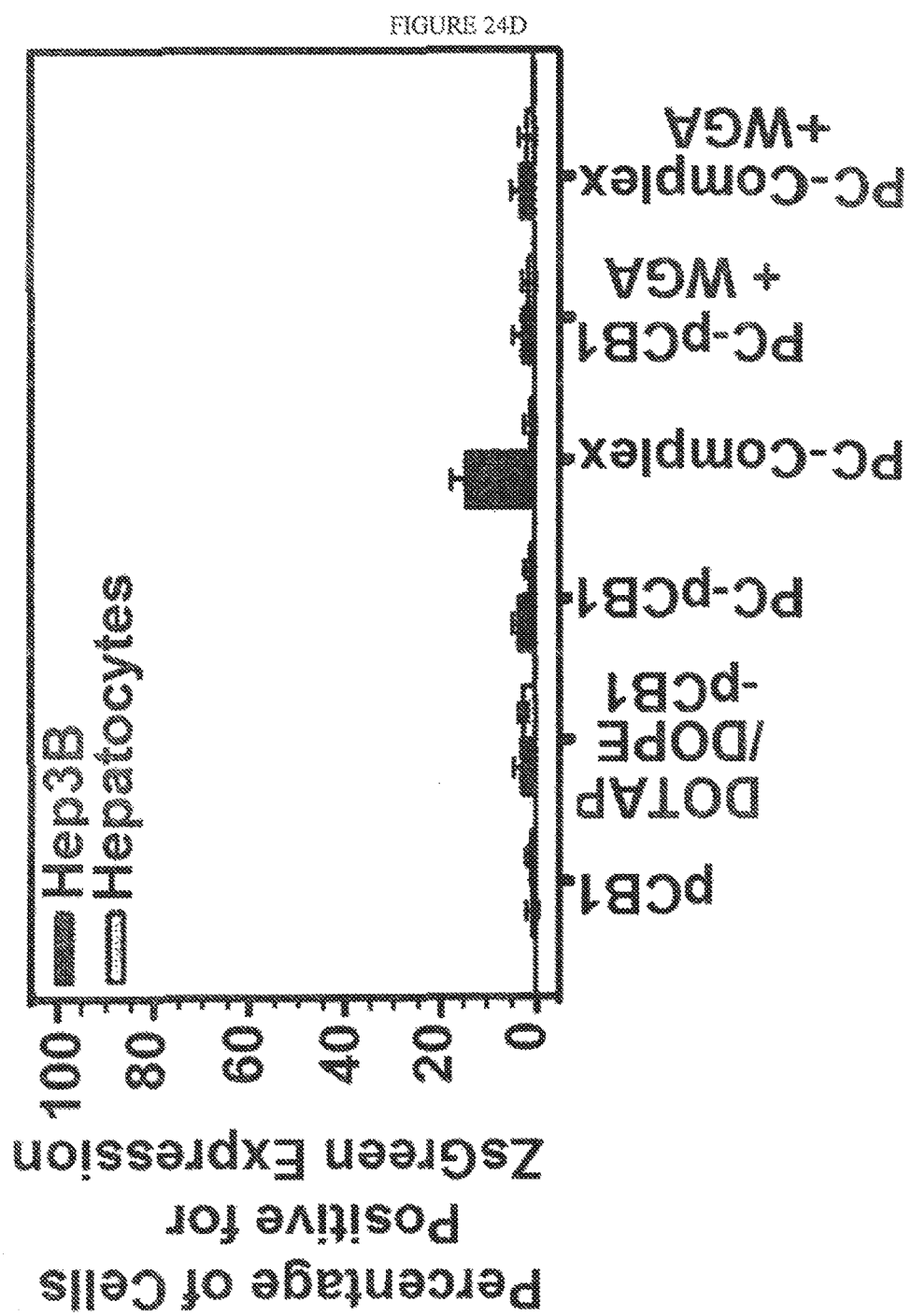

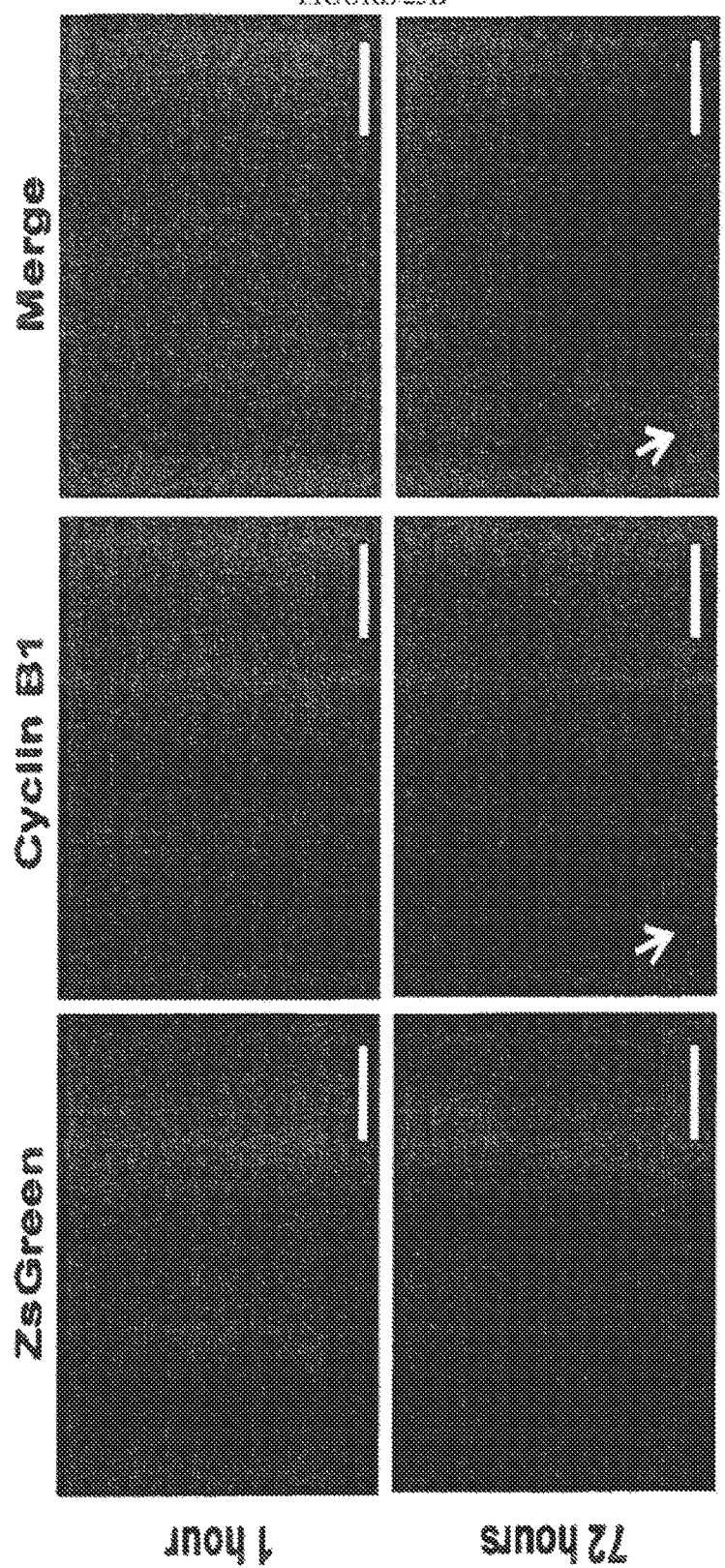

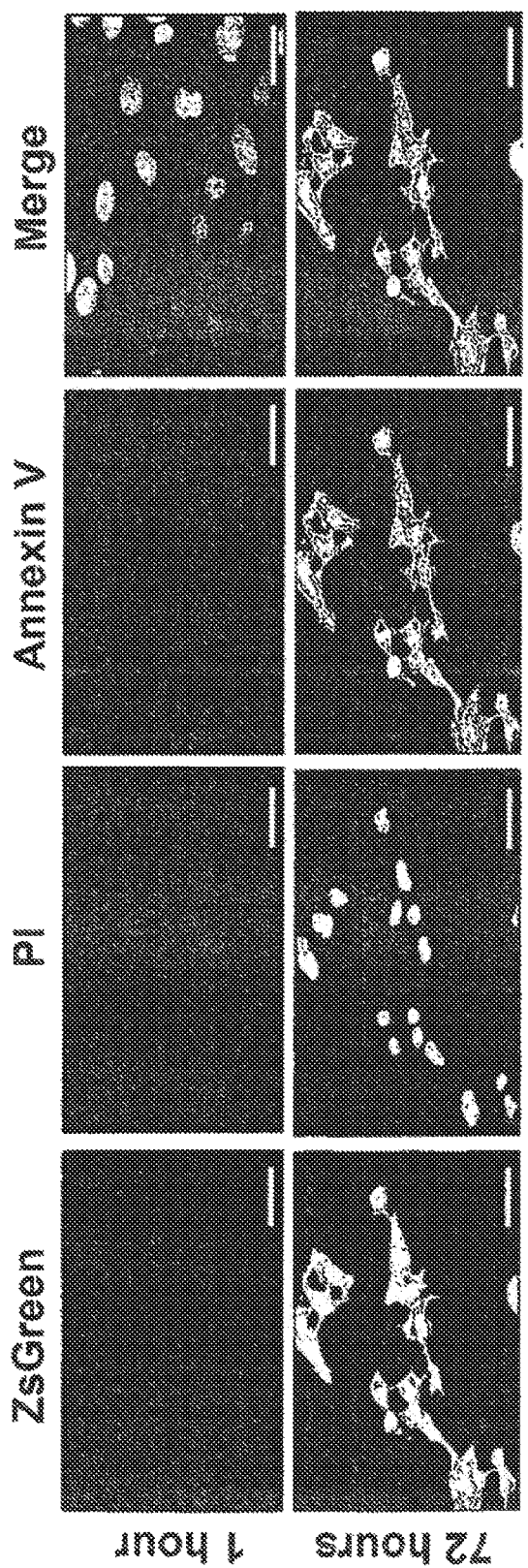

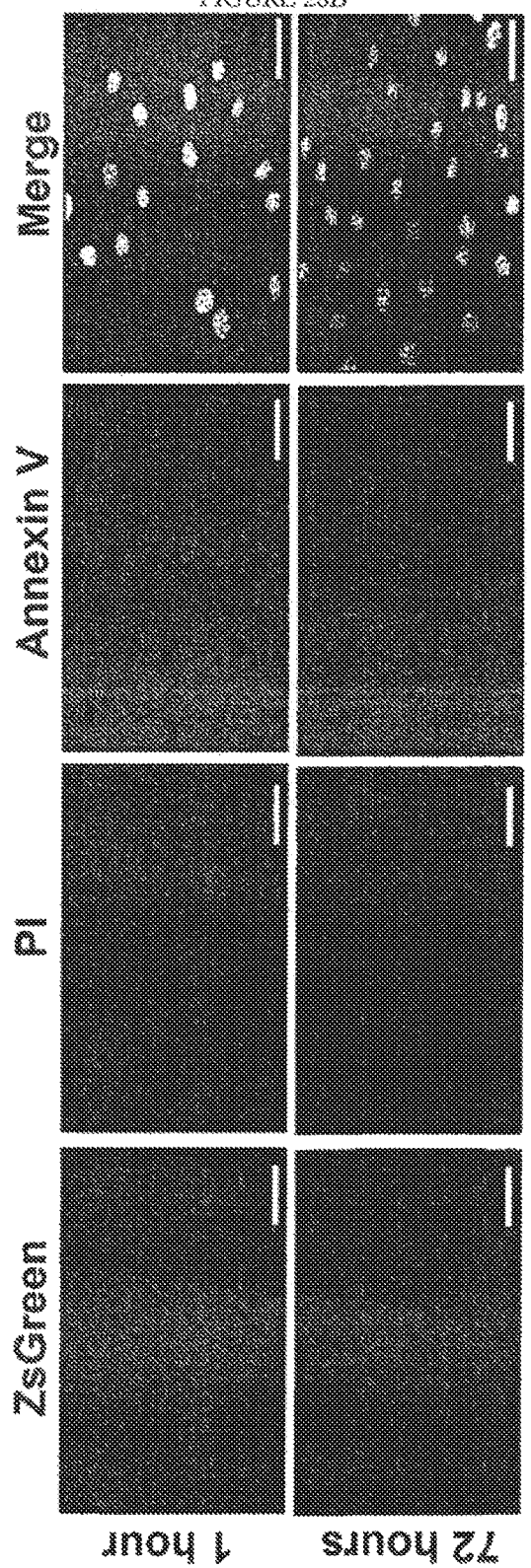

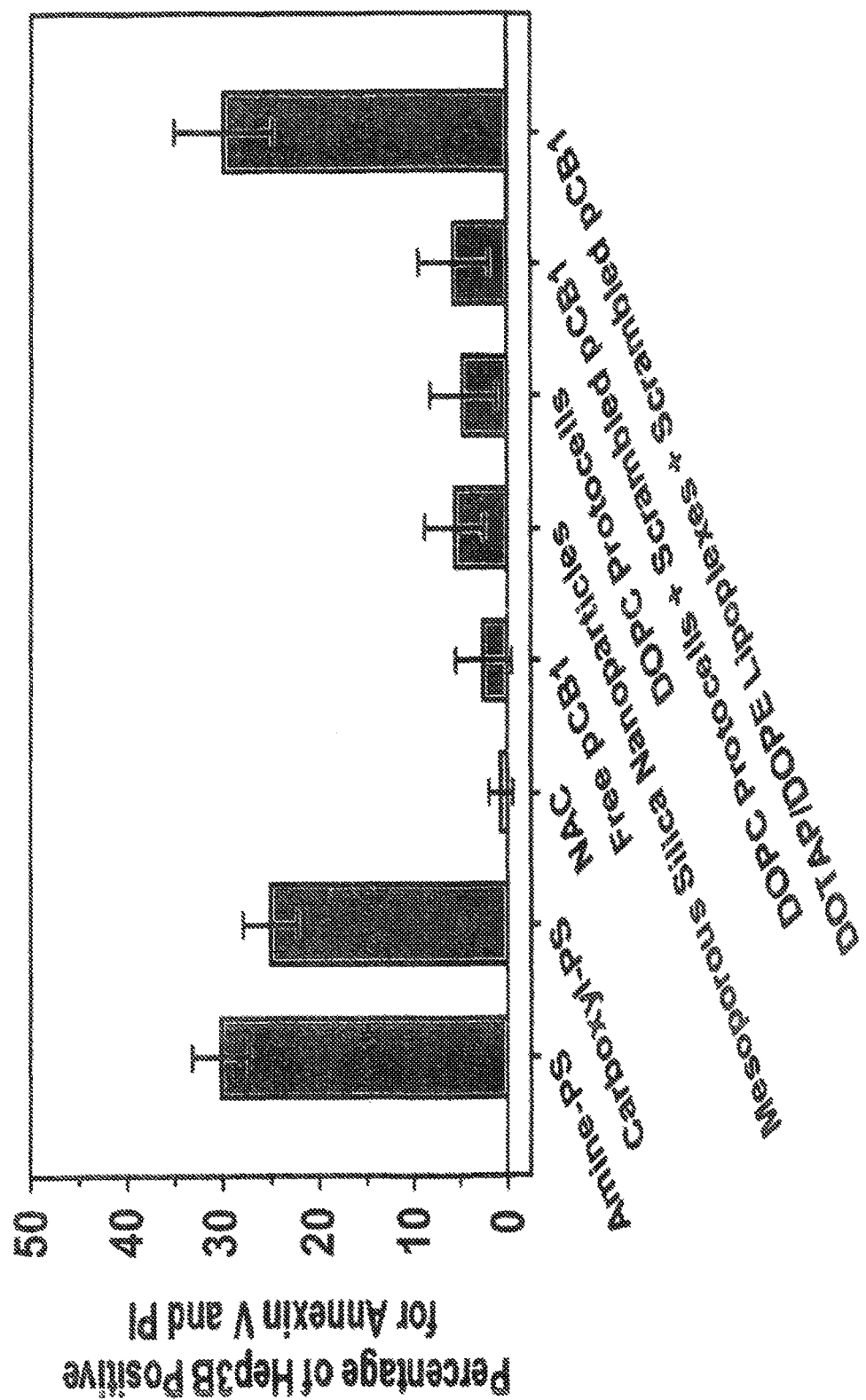

POROUS NANOPARTICLE-SUPPORTED LIPID BILAYERS (PROTOCELLS) FOR TARGETED DELIVERY AND METHODS OF USING SAME

RELATED APPLICATIONS AND GOVERNMENT SUPPORT

This invention was made with government support under grant no. U01CA151792 of the National Institutes of Health; grant nos. DE-AC04-94AL85000, LDRD 141704 and LDRD 151379 of the Department of Energy. The government has certain rights in the invention.

This invention was made with government support under grant no. PHS 2 PN2 EY016570B of the National Institutes of Health; grant no. awarded by 1U01CA151792-01 of the National Cancer Institute; grant no. FA 9550-07-1-0054/9550-10-1-0054 of the Air Force Office of Scientific Research; 1U19ES019528-01 of NIEHS; NSF:EF-0820117 of the National Science Foundation and DGE-0504276 of the National Science Foundation. The government has certain rights in the invention.

FIELD OF THE INVENTION

Embodiments of the present invention are directed to protocells for specific targeting of cells within a patient's body, especially including hepatocellular and other cancer cells which comprise a 1) a nanoporous silica or metal oxide core; 2) a supported lipid bilayer; 3) at least one agent which facilitates cancer cell death (such as a traditional small molecule, a macromolecular cargo (e.g. siRNA, shRNA other micro RNA, or a protein toxin such as ricin toxin A-chain or diphtheria toxin A-chain) and/or DNA, including double stranded or linear DNA, plasmid DNA which may be supercoiled and/or packaged such as with histones and disposed within the nanoporous silica core (preferably supercoiled in order to more efficiently package the DNA into protocells) which is optionally modified with a nuclear localization sequence to assist in localizing protocells within the nucleus of the cancer cell and the ability to express peptides involved in therapy (apoptosis/cell death) of the cancer cell or as a reporter, a targeting peptide which targets cancer cells in tissue to be treated such that binding of the protocell to the targeted cells is specific and enhanced and a fusogenic peptide that promotes endosomal escape of protocells and encapsulated cargo, including DNA. Protocells according to the present invention may be used to treat cancer, especially including hepatocellular (liver) cancer using novel binding peptides (c-MET peptides) which selectively bind to hepatocellular tissue or to function in diagnosis of cancer, including cancer treatment and drug discovery.

BACKGROUND OF THE INVENTION

Targeted delivery of drugs encapsulated within nanocarriers can potentially ameliorate a number of problems exhibited by conventional 'free' drugs, including poor solubility, limited stability, rapid clearing, and, in particular, lack of selectivity, which results in non-specific toxicity to normal cells and prevents the dose escalation necessary to eradicate diseased cells. Passive targeting schemes, which rely on the enhanced permeability of the tumor vasculature and decreased draining efficacy of tumor lymphatics to direct accumulation of nanocarriers at tumor sites (the so-called enhanced permeability and retention, or EPR effect), overcome many of these problems, but the lack of cell-specific interactions needed to induce nanocarrier internalization decreases therapeutic efficacy and can result in drug expulsion and induction of multiple drug resistance.

One of the challenges in nanomedicine is to engineer nanostructures and materials that can efficiently encapsulate cargo, for example, drugs, at high concentration, cross the cell membrane, and controllably release the drugs at the target site over a prescribed period of time. Recently, inorganic nanoparticles have emerged as a new generation of drug or therapy delivery vehicles in nanomedicine. More recently, gating methods that employ coumarin, azobenzene, rotaxane, polymers, or nanoparticles have been developed to seal a cargo within a particle and allow a triggered release according to an optical or electrochemical stimulus.

While liposomes have been widely used in drug delivery due to their low immunogenicity and low toxicity, they still need to be improved in several aspects. First, the loading of cargo can only be achieved under the condition in which liposomes are prepared. Therefore, the concentration and category of cargo may be limited. Second, the stability of liposomes is relatively low. The lipid bilayer of the liposomes often tends to age and fuse, which changes their size and size distribution. Third, the release of cargo in liposomes is instantaneous upon rupture of the liposome which makes it difficult to control the release.

A porous nanoparticle-supported lipid bilayer (protocell), formed via fusion of liposomes to nanoporous silica particles, is a novel type of nanocarrier that addresses multiple challenges associated with targeted delivery of cancer therapeutics and diagnostics. Like liposomes, protocells are biocompatible, biodegradable, and non-immunogenic, but their nanoporous silica core confers a drastically enhanced cargo capacity and prolonged bilayer stability when compared to similarly-sized liposomal delivery agents. The porosity and surface chemistry of the core can, furthermore, be modulated to promote encapsulation of a wide variety of therapeutic agents, such as drugs, nucleic acids, and protein toxins. The rate of cargo release can be controlled by pore size, chemical composition and the overall degree of silica condensation of the core, making protocells useful in applications requiring either burst or controlled release profiles. Finally, the protocell's supported lipid bilayer (SLB) can be modified with variously with ligands to promote selective delivery and with PEG to extend circulation times.

The need to improve the activity of chemotherapeutic agents and to enhance cancer therapy is ongoing. The use of protocells in conjunction with alternative approaches to targeting, binding, enhancing invasion of cancer and depositing chemotherapeutic agents in proximity to their site of activity are important facets of cancer therapy. The present invention is undertaken to advance the art of cancer therapy and to improve the delivery of agents which can influence therapeutic outcome, whether by enhancing the administration of cancer therapeutic agents or in diagnostics, to facilitate approaches to diagnosing cancer and monitoring cancer therapy.

OBJECTS OF THE INVENTION

Objects of the invention are directed to providing improvements to protocell technology, to the protocells themselves, to pharmaceutical compositions which comprise such protocells and methods of using protocells and pharmaceutical compositions according to the invention for therapy and diagnostics, including monitoring therapy.

Additional objects of embodiments of the invention relate to novel MET binding peptides, their use in pharmaceutical compositions and methods according to other embodiments the present invention.

These and/or other objects of the invention may be readily gleaned from a review of a description as presented in the specification.

BRIEF DESCRIPTION OF THE INVENTION

Embodiments of the present invention are directed to protocells for specific targeting of cells, in particular aspects, hepatocellular and other cancer cells.

In certain aspects, the present invention is directed to a cell-targeting porous protocell comprising a nanoporous silica or metal oxide core with a supported lipid bilayer, and at least one further component selected from the group consisting of
  a cell targeting species;
  a fusogenic peptide that promotes endosomal escape of protocells and encapsulated DNA, and other cargo comprising at least one cargo component selected from the group consisting of double stranded linear DNA or a plasmid DNA;
  a drug;
  an imaging agent,
  small interfering RNA, small hairpin RNA, microRNA, or a mixture thereof,
  wherein one of said cargo components is optionally conjugated further with a nuclear localization sequence.

In certain embodiments, protocells according to embodiments of the invention comprise a nanoporous silica core with a supported lipid bilayer; a cargo comprising at least one therapeutic agent which optionally facilitates cancer cell death such as a traditional small molecule, a macromolecular cargo (e.g. siRNA such as S565, S7824 and/or s10234, among others, shRNA or a protein toxin such as a ricin toxin A-chain or diphtheria toxin A-chain) and/or a packaged plasmid DNA (in certain embodiments—histone packaged) disposed within the nanoporous silica core (preferably supercoiled as otherwise described herein in order to more efficiently package the DNA into protocells as a cargo element) which is optionally modified with a nuclear localization sequence to assist in localizing/presenting the plasmid within the nucleus of the cancer cell and the ability to express peptides involved in therapy (e.g., apoptosis/cell death of the cancer cell) or as a reporter (fluorescent green protein, fluorescent red protein, among others, as otherwise described herein) for diagnostic applications. Protocells according to the present invention include a targeting peptide which targets cells for therapy (e.g., cancer cells in tissue to be treated) such that binding of the protocell to the targeted cells is specific and enhanced and a fusogenic peptide that promotes endosomal escape of protocells and encapsulated DNA. Protocells according to the present invention may be used in therapy or diagnostics, more specifically to treat cancer and other diseases, including viral infections, especially including hepatocellular (liver) cancer. In other aspects of the invention, proctocells use novel binding peptides (MET binding peptides as otherwise described herein) which selectively bind to cancer tissue (including hepatocellular, ovarian and cervical cancer tissue, among other tissue) for therapy and/or diagnosis of cancer, including the monitoring of cancer treatment and drug discovery.

In one aspect, protocells according to embodiments of the present invention comprise a porous nanoparticle protocell which often comprises a nanoporous silica core with a supported lipid bilayer. In this aspect of the invention, the protocell comprises a targeting peptide which is often a MET receptor binding peptide as otherwise described herein, often in combination with a fusogenic peptide on the surface of the protocell. The protocell may be loaded with various therapeutic and/or diagnostic cargo, including for example, small molecules (therapeutic and/or diagnostic, especially including anticancer and/or antiviral agents (for treatment of HBV and/or HCV), macromolecules including polypeptides and nucleotides, including RNA (shRNA and siRNA) or plasmid DNA which may be supercoiled and histone-packaged including a nuclear localization sequence, which may be therapeutic and/or diagnostic (including a reporter molecule such as a fluorescent peptide, including fluorescent green protein/FGP, fluorescent red protein/FRP, among others).

Other aspects of embodiments of the present invention are directed to pharmaceutical compositions. Pharmaceutical compositions according to the present invention comprise a population of protocells which may be the same or different and are formulated in combination with a pharmaceutically acceptable carrier, additive or excipient. The protocells may be formulated alone or in combination with another bioactive agent (such as an additional anti-cancer agent or an antiviral agent) depending upon the disease treated and the route of administration (as otherwise described herein). These compositions comprise protocells as modified for a particular purpose (e.g. therapy, including cancer therapy, or diagnostics, including the monitoring of cancer therapy). Pharmaceutical compositions comprise an effective population of protocells for a particular purpose and route of administration in combination with a pharmaceutically acceptable carrier, additive or excipient.

An embodiment of the present invention also relates to methods of utilizing the novel protocells as described herein. Thus, in alternative embodiments, the present invention relates to a method of treating a disease and/or condition comprising administering to a patient or subject in need an effective amount of a pharmaceutical composition as otherwise described herein. The pharmaceutical compositions according to the present invention are particularly useful for the treatment of a number disease states, especially including cancer, and disease states or conditions which occur secondary to cancer or are the cause of cancer (in particular, HBV and/or HCV infections).

In further alternative aspects, the present invention relates to methods of diagnosing cancer, the method comprising administering a pharmaceutical composition comprising a population of protocells which have been modified to deliver a diagnostic agent or reporter imaging agent selectively to cancer cells to identify cancer in the patient. In this method, protocells according to the present invention may be adapted to target cancer cells through the inclusion of at least one targeting peptide which binds to cancer cells which express polypeptides or more generally, surface receptors to cell membrane components, which are the object of the targeting peptide and through the inclusion of a reporter component (including an imaging agent) of the protocell targeted to the cancer cell, may be used to identify the existence and size of cancerous tissue in a patient or subject by comparing a signal from the reporter with a standard. The standard may be obtained for example, from a population of healthy patients or patients known to have a disease for which diagnosis is made. Once diagnosed, appropriate therapy with pharmaceutical compositions according to the present invention, or alternative therapy may be implemented.

In still other aspects of the invention, the compositions according to the present invention may be used to monitor the progress of therapy of a particular disease state and/or condition, including therapy with compositions according to the present invention. In this aspect of the invention, a composition comprising a population of protocells which are specific for cancer cell binding and include a reporter component may be administered to a patient or subject undergoing therapy such that progression of the therapy of the disease state can be monitored.

Alternative aspects of the invention relate to five (5) novel MET binding peptides as otherwise described herein, which can be used as targeting peptides on protocells of certain embodiments of the present invention, or in pharmaceutical compositions for their benefit in binding MET protein in a variety of cancer cells, including hepatocellular, cervical and ovarian cells, among numerous other cells in cancerous tissue. One embodiment of the invention relates to five (5) different 7 mer peptides which show activity as novel binding peptides for MET receptor (a.k.a. hepatocyte growth factor receptor, expressed by gene c-MET). These five (5) 7 mer peptides are as follows:

SEQ ID NO: 1
ASVHFPP (Ala-Ser-Val-His-Phe-Pro-Pro)

SEQ ID NO: 2
TATFWFQ (Thr-Ala-Thr-Phe-Trp-Phe-Gln)

SEQ ID NO: 3
TSPVALL (Thr-Ser-Pro-Val-Ala-Leu-Leu)

SEQ ID NO: 4
IPLKVHP (Ile-Pro-Leu-Lys-Val-His-Pro)

SEQ ID NO: 5
WPRLTNM (Trp-Pro-Arg-Leu-Thr-Asn-Met)

Each of these peptides may be used alone or in combination with other MET binding peptides within the above group or with a spectrum of other targeting peptides (e.g., SP94 peptides as described herein) which may assist in binding protocells according to an embodiment of the present invention to cancer cells, including hepatocellular cancer cells, ovarian cancer cells, breast cancer cells and cervical cancer cells, among numerous others. These binding peptides may also be used in pharmaceutical compounds alone as MET binding peptides to treat cancer and otherwise inhibit hepatocyte growth factor binding receptor. These peptides may be formulated alone or in combination with other bioactive agents for purposes of providing an intended result. Pharmaceutical compositions comprise an effective amount of at least one of the five (5) MET-binding peptides identified above, in combination with a pharmaceutically acceptable carrier, additive or excipient optionally in combination with an additional bioactive agent, which may include an anticancer agent, antiviral agent or other bioactive agent.

BRIEF DESCRIPTION OF THE FIGURES

FIG. 2A shows the pore size and framework designed to be tailorable for multiple types of cargo and that aerosolized auxiliary components are easily incorporated according to one embodiment.

FIG. 2B shows that that a, b, c, and e of FIG. 2A are templated by CTAB, B58, P123 and PS+B56. A, B, C, D and E are templated by CTAP+NaCl, 3% wt P123, 3% wt P123+poly(propylene glycol acrylate), microemulsion and CTAB(NH4)S04.

FIG. 7 provides a schematic depicting the process by which MC40-targeted protocells deliver histone-packaged pCB1 to HCC. [1] MC40-targeted protocells bind to Hep3B cells with high affinity due to the recruitment of targeting peptides to Met, which is over-expressed by a variety of HCC lines. The fluid DOPC SLB promotes peptide mobility and, therefore, enables protocells modified with a low MC40 density to retain a high specific affinity for Hep3B (see FIG. 8A). [2] MC40-targeted protocells become internalized by Hep3B via receptor-mediated endocytosis (see FIGS. 8B and FIG. 15A). [3] Endosomal conditions destabilize the SLB [insert Nature Materials ref] and cause protonation of the H5WYG endosomolytic peptide, both of which enable histone-packaged pCB1 to become dispersed in the cytosol of Hep3B cells (see FIG. 16B). [4] pCB1-histone complexes, when modified with a nuclear localization sequence (NLS), become concentrated in the nuclei of Hep3B cells within ~24 hours (see FIG. 16C), which enables efficient transfection of both dividing and non-dividing cancer cells (see FIG. 17).

FIG. 10 shows MC40-targeted, pCB1-loaded protocells induce selective apoptosis of HCC 2500-fold more effectively than corresponding lipoplexes. (A) Zeta potential values for DOPC protocells, DOPC protocells modified with 10 wt % PEG-2000 (18:1), lipoplexes composed of pCB1 and a mixture of DOTAP and DOPE (1:1 w/w), and DOTAP/DOPE lipoplexes modified with 10 wt % PEG-2000. All zeta potential measurements were conducted in 0.5×PBS (pH 7.4). (B, left axis) The percentage of Hep3B and hepatocytes that become apoptotic upon continual exposure to 5 pM of pCB1, delivered via MC40-targeted protocells or lipoplexes, for 48 hours at 37° C. (B, right axis) The number of MC40-targeted, pCB1-loaded protocells or lipoplexes necessary to induce apoptosis in 90% of 1×10$^6$ Hep3B cells within 48 hours at 37° C. For (B), cells were stained with Alexa Fluor® 647-labeled annexin V and propidium iodide; single-and double-positive cells were considered to be apoptotic. Protocell SLBs were composed of DOPC with 5 wt % DOPE, 30 wt % cholesterol, and 10 wt % PEG-2000 (when indicated) and were modified with 0.015 wt % MC40 and 0.500 wt % H5WYG. DOTAP/DOPE lipoplexes were modified with 10 wt % PEG-2000 (when indicated), 0.015 wt % MC40, and 0.500 wt % H5WYG. pCB1 was modified with the NLS in all experiments. All error bars represent 95% confidence intervals (1.96σ) for n=3.

FIG. 14 shows nitrogen sorption analysis of unloaded and pCB1-loaded mesoporous silica nanoparticles. (A) Nitrogen sorption isotherms for mesoporous silica nanoparticles before and after loading with histone-packaged pCB1. (B) Brunauer-Emmett-Teller (BET) surface area of mesoporous silica nanoparticles, before and after loading with histone-packaged pCB1. Error bars represent 95% confidence intervals (1.96σ) for n=3.

FIG. 17 shows zeta potential (ζ) values for mesoporous silica nanoparticles ('unmodified cores'), mesoporous silica nanoparticles that were soaked in 20% (v/v) APTES for 12 hours at room temperature ('APTES-modified cores'), the CB1 plasmid ('pCB1'), histone-packaged pCB1 ('pCB1-histone complex'), and pCB1 packaged with a 1:1 (w/w) mixture of DOTAP and DOPE ('DOTAP/DOPE Lipoplexes'). Zeta potential measurements were conducted in 0.5×PBS (pH 7.4). Error bars represent 95% confidence intervals (1.96σ) for n=3.

Figure 1:
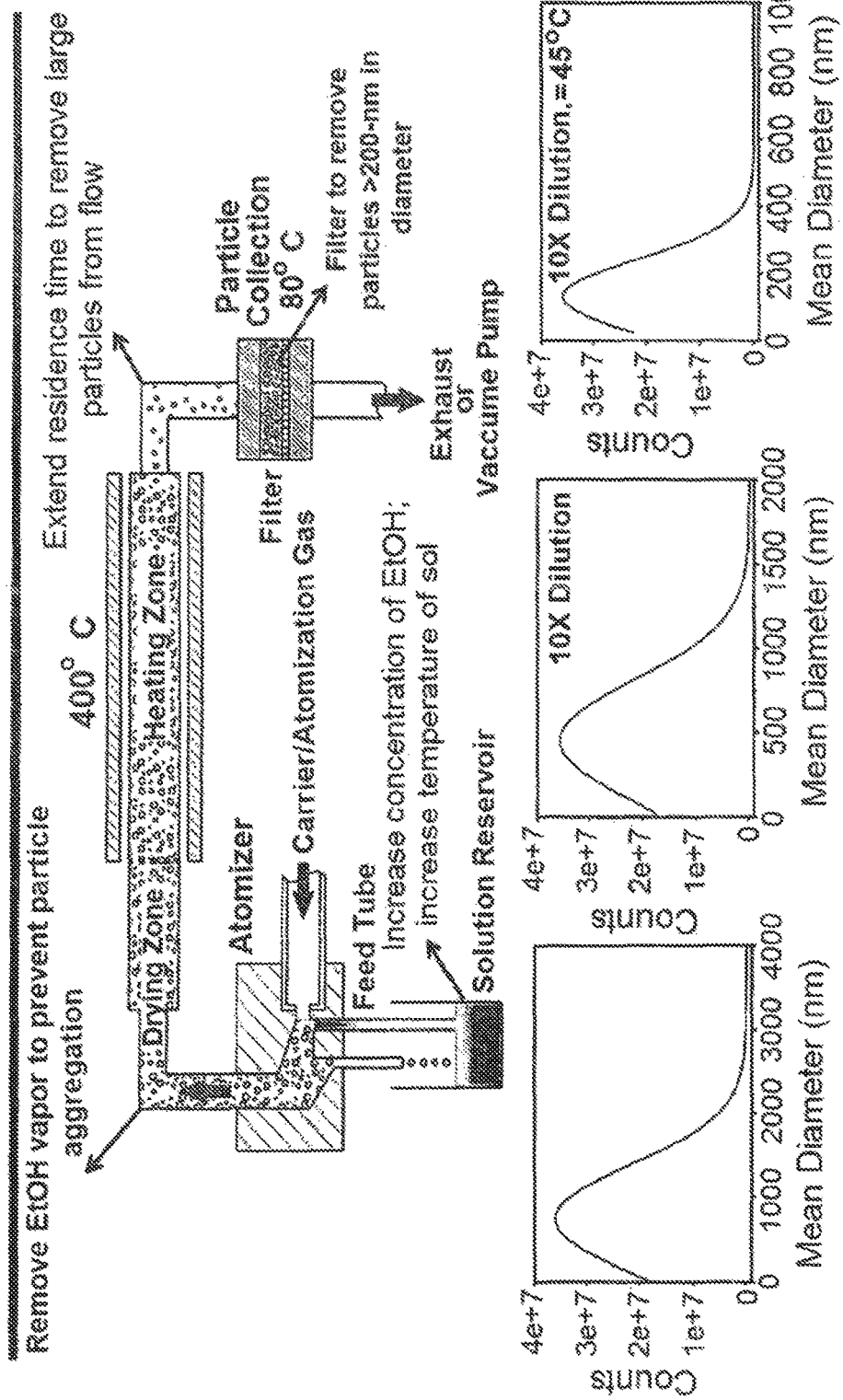
FIG. 1 shows that the nanoparticles according to one embodiment used in the present invention which are prepared by an aerosol-assisted EISA process can be altered to control particle size and distribution.

To determine the dissociation constants in FIG. 8A, $1\times10^6$ Hep3B or hepatocytes were pre-treated with cytochalasin B to inhibit endocytosis and incubated with various concentrations of Alexa Fluor® 647-labeled, MC40-targeted protocells for 1 hour at 37° C. Flow cytometry was used to determine mean fluorescence intensities for the resulting cell populations, which were plotted against protocell concentrations to obtain total binding curves. Non-specific binding was determined by incubating cells with Alexa Fluor® 647-labeled, MC40-targeted protocells in the presence of a saturating concentration of unlabeled hepatocyte growth factor. Specific binding curves were obtained by subtracting non-specific binding curves from total binding curves; $K_d$ values were calculated from specific binding curves. In the experiments depicted in this figure, protocell SLBs were composed of DOPC with 5 wt % DOPE, 30 wt % cholesterol, and 10 wt % PEG-2000 (18:1) and were modified with 0.015 wt % (~6 peptides/particle) of the MC40 targeting peptide; the corresponding $K_d$ value is 1050±142 pM. All error bars represent 95% confidence intervals (1.96σ) for n=5.

FIG. 22 shows that MC40-targeted protocells are internalized via receptor-mediated endocytosis and, in the absence of the H5WYG peptide, are directed to lysosomes. (A) The average number of MC40-targeted protocells internalized by each Hep3B or hepatocyte cell within one hour at 37° C. $1\times10^6$ cells were incubated with various concentrations of protocells in the absence (−) or presence (+) of a saturating concentration (100 µg/mL) of human hepatocyte growth factor (HGF), and flow cytometry was used to determine the average number of particles associated with each cell. Protocells were labeled with NBD and pHrodo™ to distinguish surface-bound particles from those internalized into acidic intracellular compartments (respectively). Error bars represent 95% confidence intervals (1.96σ) for n=3. (B) Pearson's correlation coefficients (r-values) between protocells and: (1) Rab5, (2) Rab7, (3) Lysosomal-Associated Membrane Protein 1 (LAMP-1), or (4) Rab11a. Hep3B cells were incubated with a 1000-fold excess of Alexa Fluor® 594-labeled protocells for 1 hour at 37° C. before being fixed, permeabilized, and incubated with Alexa Fluor® 488-labeled antibodies against Rab5, Rab7, LAMP-1, or Rab11a. SlideBook software was used to determine r-values, which are expressed as the mean value±the standard deviation for n=3×50 cells. Differential Interference Contrast (DIC) images were employed to define the boundaries of Hep3B cells so that pixels outside of the cell boundaries could be disregarded when calculating r-values. Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG.

FIG. 23 shows that histone-packaged pCB1, when modified with a NLS and delivered via MC40-targeted protocells, becomes concentrated in the nuclei of HCC cells in a time-dependent manner. (A)-(C) Confocal fluorescence microscopy images of Hep3B cells exposed to a 1000-fold excess of MC40-targeted, pCB1-loaded protocells for 15 minutes (A), 12 hours (B), or 24 hours (C) at 37° C. For (B), endosomal escape of protocells and cytosolic dispersion of pCB1 was evident after ~2 hours; ZsGreen expression was not detectable until 12-16 hours, however. At 24 hours, Cy5-labeled pCB1 remained distributed throughout the cells; cytosolic staining is not visible in (C), however, since the gain of the Cy5 channel was reduced to avoid saturation of pixels localized within the nuclei. Silica cores were labeled with Alexa Fluor® 594 (red), pCB1 was labeled with Cy5 (white), and cell nuclei were counterstained with Hoechst 33342 (blue). Scale bars=20 µm. (D) Pearson's correlation coefficients (r-values) versus time for Cy5-labeled pCB1 and Hoechst 33342-labeled Hep3B nuclei. SlideBook software was used to determine r-values, which are expressed as the mean value±the standard deviation for n=3×50 cells. Differential Interference Contrast (DIC) images were employed to define the boundaries of Hep3B cells so that pixels outside of the cell boundaries could be disregarded when calculating r-values. Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG.

FIG. 24 shows that histone-packaged pCB1, when modified with a NLS and delivered via MC40-targeted protocells, selectively transfects both dividing and non-dividing HCC cells with nearly 100% efficacy. (A), (C), and (E) Confocal fluorescence microscopy images of Hep3B cells exposed to a 1000-fold excess of MC40-targeted, pCB1-loaded protocells for 24 hours at 37° C. Hep3B cells were dividing in (A) and ~95% confluent in (C) and (E); pCB1 was pre-packaged with histones in all images, and the pCB1-histone complex was further modified with a NLS in (E). Silica cores were labeled with Alexa Fluor® 594 (red), pCB1 was labeled with Cy5 (white), and cell nuclei were counterstained with Hoechst 33342 (blue). Scale bars=20 µm. (B), (D), and (F) The percentage of $1\times10^6$ Hep3B and hepatocytes that become positive for ZsGreen expression upon continual exposure to $1\times10^9$ MC40-targeted, pCB1-loaded protocells ('PC') for 24 hours at 37° C. Cells were dividing in (B) and ~95% confluent in (D) and (F); the x-axes indicate whether CB1 plasmids ('pCB1') and pCB1-histone complexes ('complex') were modified with the NLS. pCB1 alone, as well as pCB1 packaged with a 1:1 (w/w) mixture of DOTAP and DOPE were employed as controls. Cells were exposed to 20 mg/mL of wheat germ agglutinin (WGA) to block translocation of NLS-modified pCB1 through the nuclear pore complex. Error bars represent 95% confidence intervals (1.96σ) for n=3. (G)-(I) Cell cycle histograms for cells employed in (A), (C), and (E), respectively. The percentage of cells in $G_0/G_1$ phase is given for each histogram. In all experiments, protocell SLBs were composed of DOPC with 5 wt % DOPE, 30 wt % cholesterol, and 10 wt % PEG-2000 (18:1) and were modified with 0.015 wt % MC40 and 0.500 wt % H5WYG.

Figure 25A:
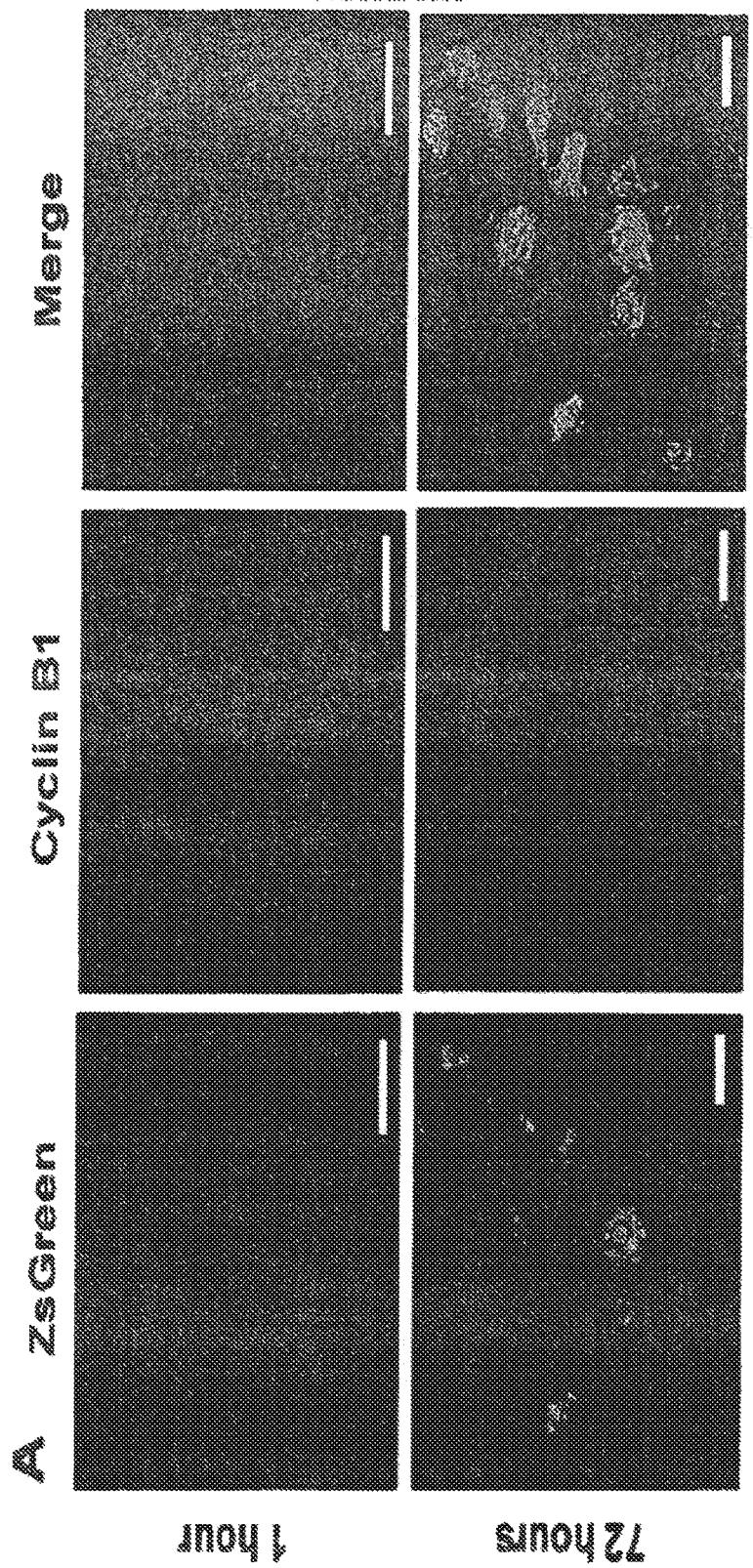

FIG. 25 shows confocal fluorescence microscopy images of Hep3B (A) and hepatocytes (B) that were exposed to MC40-targeted, pCB1-loaded protocells for either 1 hour or 72 hours at 37° C.; the pCB1 concentration was maintained at 5 pM in all experiments. The arrows in (B) indicate mitotic cells. Cyclin B1 was labeled with an Alexa Fluor® 594-labeled monoclonal antibody (red), and cell nuclei were stained with Hoechst 33342 (blue). Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. All scale bars=20 μm.

FIG. 26 shows confocal fluorescence microscopy images of Hep3B (A) and hepatocytes (B) that were exposed to MC40-targeted, pCB1-loaded protocells for either 1 hour or 72 hours at 37° C.; the pCB1 concentration was maintained at 5 pM in all experiments. Cells were stained with Alexa Fluor 647-labeled annexin V (white) and propidium iodide (red) to assay for early and late apoptosis, respectively, and cell nuclei were counterstained with Hoechst 33342 (blue). Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. All scale bars=20 μm.

FIG. 27 shows that protocells with a SLB composed of zwitterionic lipids induce minimal non-specific cytotoxicity. The percentage of $1 \times 10^6$ Hep3B that become apoptotic upon continual exposure to $1 \times 10^9$ APTES-modified mesoporous silica nanoparticles, DOPC protocells with APTES-modified cores, DOPC protocells loaded with a plasmid that encodes a scrambled shRNA sequence ('scrambled pCB1'), or DOTAP/DOPE (1:1 w/w) lipoplexes loaded with scrambled pCB1 for 48 hours at 37° C. Protocells and lipoplexes were modified with 10 wt % PEG-2000, 0.015 wt % MC40, and 0.500 wt % H5WYG. Positively-and negatively-charged polystyrene nanoparticles ('amine-PS' and 'Carboxyl-PS', respectively) were employed as positive controls, while Hep3B exposed to 10 mM of the antioxidant, N-acetylcysteine (NAC), or to 1 pmol of free pCB1 were used as negative controls. All error bars represent 95% confidence intervals (1.96σ) for n=3.

DETAILED DESCRIPTION OF THE INVENTION

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diastereomers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein.

The term "bioactive agent" refers to any biologically active compound or drug which may be formulated for use in an embodiment of the present invention. Exemplary bioactive agents include the compounds according to the present invention which are used to treat cancer or a disease state or condition which occurs secondary to cancer and may include antiviral agents, especially anti-HIV, anti-HBV and/ or anti-HCV agents (especially where hepatocellular cancer is to be treated) as well as other compounds or agents which are otherwise described herein.

The terms "treat", "treating", and "treatment", are used synonymously to refer to any action providing a benefit to a patient at risk for or afflicted with a disease, including improvement in the condition through lessening, inhibition, suppression or elimination of at least one symptom, delay in progression of the disease, prevention, delay in or inhibition of the likelihood of the onset of the disease, etc. In the case of viral infections, these terms also apply to viral infections and preferably include, in certain particularly favorable embodiments the eradication or elimination (as provided by limits of diagnostics) of the virus which is the causative agent of the infection.

Treatment, as used herein, encompasses both prophylactic and therapeutic treatment, principally of cancer, but also of other disease states, including viral infections, especially including HBV and/or HCV. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease (inhibition) that subsequently occurs, especially including metastasis of cancer. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present invention is effective to decrease the severity of the disease or lengthen the lifespan of the mammal so afflicted, as in the case of cancer, or inhibit or even eliminate the causative agent of the disease, as in the case of hepatitis B virus (HBV) and/or hepatitis C virus infections (HCV) infections.

The term "pharmaceutically acceptable" as used herein means that the compound or composition is suitable for administration to a subject, including a human patient, to achieve the treatments described herein, without unduly deleterious side effects in light of the severity of the disease and necessity of the treatment.

The term "inhibit" as used herein refers to the partial or complete elimination of a potential effect, while inhibitors are compounds/compositions that have the ability to inhibit.

The term "prevention" when used in context shall mean "reducing the likelihood" or preventing a disease, condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients or subjects, administration with compounds according to the present invention will reduce the likelihood or inhibit a particular condition or disease state (in particular, the worsening of a disease state such as the growth or metastasis of cancer) or other accepted indicators of disease progression from occurring.

The term "protocell" is used to describe a porous nanoparticle which is made of a material comprising silica, polystyrene, alumina, titania, zirconia, or generally metal oxides, organometallates, organosilicates or mixtures thereof. A porous spherical silica nanoparticle is used for the preferred protocells and is surrounded by a supported lipid or polymer bilayer or multilayer. Various embodiments according to the present invention provide nanostructures and methods for constructing and using the nanostructures and providing protocells according to the present invention. Many of the protocells in their most elemental form are known in the art. Porous silica particles of varying sizes ranging in size (diameter) from less than 5 nm to 200 nm or 500 nm or more are readily available in the art or can be readily prepared using methods known in the art (see the examples section) or alternatively, can be purchased from Melorium Technologies, Rochester, N.Y. SkySpring Nanomaterials, Inc., Houston, Tex., USA or from Discovery Scientific, Inc., Vancouver, British Columbia. Multimodal silica nanoparticles may be readily prepared using the procedure of Carroll, et al., *Langmuir,* 25, 13540-13544 (2009). Protocells can be readily obtained using methodologies known in the art. The examples section of the present application provides certain methodology for obtaining protocells which are useful in the present invention. Protocells according to the present invention may be readily prepared, including protocells comprising lipids which are fused to the surface of the silica nanoparticle. See, for example, Liu, et al., *Chem. Comm.,* 5100-5102 (2009), Liu, et al., *J. Amer. Chem. Soc.,* 131, 1354-1355 (2009), Liu, et al., *J. Amer. Chem. Soc.,* 131, 7567-7569 (2009) Lu, et al., *Nature,* 398, 223-226 (1999), Preferred protocells for use in the present invention are prepared according to the procedures which are presented in Ashley, et al., *Nature Materials,* 2011, May; 10(5):389-97, Lu, et al., *Nature,* 398, 223-226 (1999), Caroll, et al., *Langmuir,* 25, 13540-13544 (2009), and as otherwise presented in the experimental section which follows.

In an embodiment of the present invention, the nanostructures include a core-shell structure which comprises a porous particle core surrounded by a shell of lipid preferably a bilayer, but possibly a monolayer or multilayer (see Liu, et al., *JACS,* 2009, Id). The porous particle core can include, for example, a porous nanoparticle made of an inorganic and/or organic material as set forth above surrounded by a lipid bilayer. In the present invention, these lipid bilayer surrounded nanostructures are referred to as "protocells" or "functional protocells," since they have a supported lipid bilayer membrane structure. In embodiments according to the present invention, the porous particle core of the protocells can be loaded with various desired species ("cargo"), including small molecules (e.g. anticancer agents as otherwise described herein), large molecules (e.g. including macromolecules such as RNA, including small interfering RNA or siRNA or small hairpin RNA or shRNA or a polypeptide which may include a polypeptide toxin such as a ricin toxin A-chain or other toxic polypeptide such as diphtheria toxin A-chain DTx, among others) or a reporter polypeptide (e.g. fluorescent green protein, among others) or semiconductor quantum dots, or metallic nanoparticles, or metal oxide nanoparticles or combinations thereof. In certain preferred aspects of the invention, the protocells are loaded with super-coiled plasmid DNA, which can be used to deliver a therapeutic and/or diagnostic peptide(s) or a small hairpin RNA/shRNA or small interfering RNA/siRNA which can be used to inhibit expression of proteins (such as, for example growth factor receptors or other receptors which are responsible for or assist in the growth of a cell especially a cancer cell, including epithelial growth factor/EGFR, vascular endothelial growth factor receptor/VEGFR-2 or platelet derived growth factor receptor/PDGFR-$\alpha$, among numerous others, and induce growth arrest and apoptosis of cancer cells).

In certain embodiments, the cargo components can include, but are not limited to, chemical small molecules (especially anticancer agents and antiviral agents, including anti-HIV, anti-HBV and/or anti-HCV agents, nucleic acids (DNA and RNA, including siRNA and shRNA and plasmids which, after delivery to a cell, express one or more polypeptides or RNA molecules), such as for a particular purpose, such as a therapeutic application or a diagnostic application as otherwise disclosed herein.

In embodiments, the lipid bilayer of the protocells can provide biocompatibility and can be modified to possess targeting species including, for example, targeting peptides including antibodies, aptamers, and PEG (polyethylene glycol) to allow, for example, further stability of the protocells and/or a targeted delivery into a bioactive cell.

The protocells particle size distribution, according to the present invention, depending on the application, may be monodisperse or polydisperse. The silica cores can be rather monodisperse (i.e., a uniform sized population varying no more than about 5% in diameter e.g., ±10-nm for a 200 nm diameter protocell especially if they are prepared using solution techniques) or rather polydisperse (i.e., a polydisperse population can vary widely from a mean or medium diameter, e.g., up to ±200-nm or more if prepared by aerosol. See FIG. 1, attached. Polydisperse populations can be sized into monodisperse populations. All of these are suitable for protocell formation. In the present invention, preferred protocells are preferably no more than about 500 nm in diameter, preferably no more than about 200 nm in diameter in order to afford delivery to a patient or subject and produce an intended therapeutic effect.

Protocells according to the present invention generally range in size from greater than about 8-10 nm to about 5 µm in diameter, preferably about 20-nm-3 µm in diameter, about 10 nm to about 500 nm, more preferably about 20-200-nm (including about 150 nm, which may be a mean or median diameter). As discussed above, the protocell population may be considered monodisperse or polydisperse based upon the mean or median diameter of the population of protocells. Size is very important to therapeutic and diagnostic aspects of the present invention as particles smaller than about 8-nm diameter are excreted through kidneys, and those particles larger than about 200 nm are trapped by the liver and spleen. Thus, an embodiment of the present invention focuses in smaller sized protocells for drug delivery and diagnostics in the patient or subject.

Protocells according the present invention are characterized by containing mesopores, preferably pores which are found in the nanostructure material. These pores (at least one, but often a large plurality) may be found intersecting the surface of the nanoparticle (by having one or both ends of the pore appearing on the surface of the nanoparticle) or internal to the nanostructure with at least one or more mesopore interconnecting with the surface mesopores of the nanoparticle. Interconnecting pores of smaller size are often found internal to the surface mesopores. The overall range of pore size of the mesopores can be 0.03-50-nm in diameter.

Preferred pore sizes of mesopores range from about 2-30 nm; they can be monosized or bimodal or graded—they can be ordered or disordered (essentially randomly disposed or worm-like). See FIG. 2A.

Mesopores (IUPAC definition 2-50-nm in diameter) are 'molded' by templating agents including surfactants, block copolymers, molecules, macromolecules, emulsions, latex beads, or nanoparticles. In addition, processes could also lead to micropores (IUPAC definition less than 2-nm in diameter) all the way down to about 0.03-nm e.g. if a templating moiety in the aerosol process is not used. They could also be enlarged to macropores, i.e., 50-nm in diameter.

Figure 3:
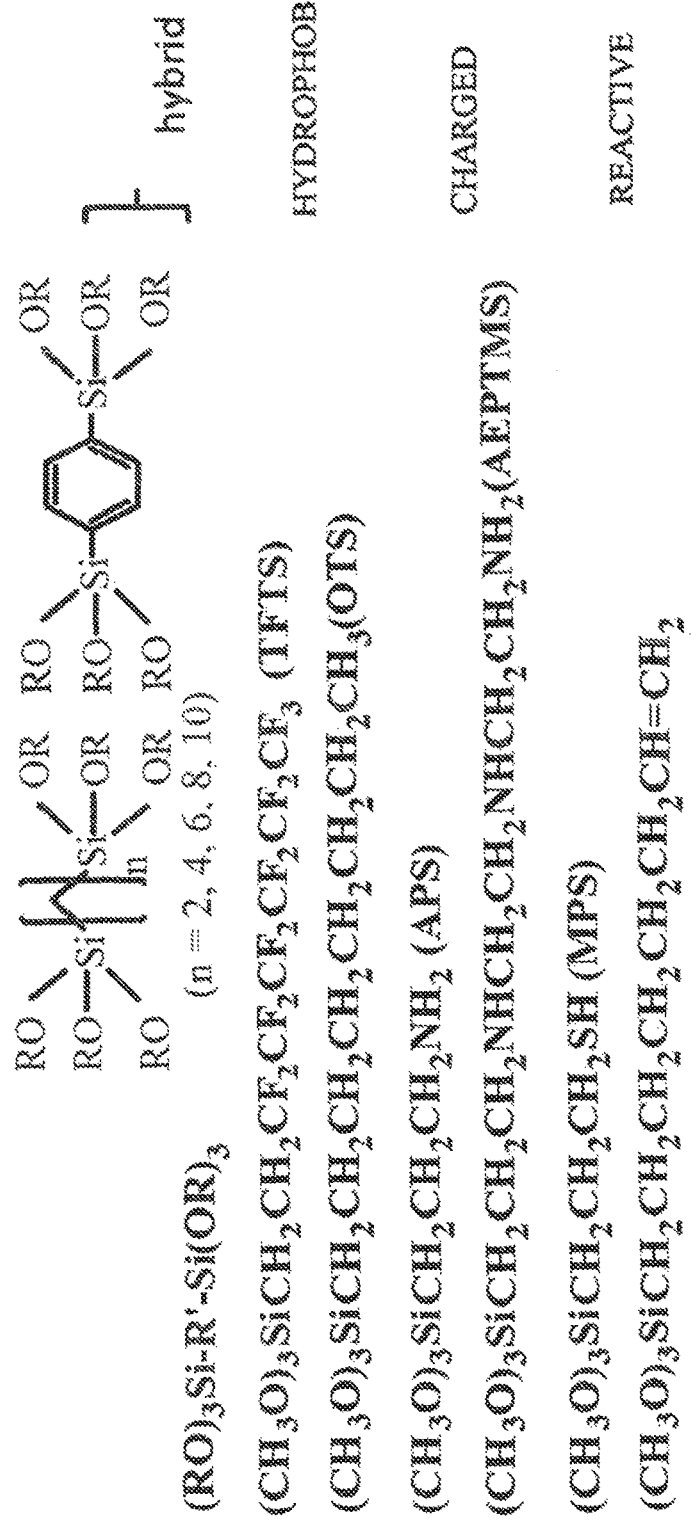
FIG. 3 shows that pore surface chemistry (i.e., charge and hydrophobicity) and pore size is controlled principally by co-condensation of organo-silanes and silicic acids either by co-self-assembly or post-self-assembly derivatization according to one embodiment. See Lin, et al., *Chem. Mater.* 15, 4247-56 2003; Liu, J. et al., *J. Phys. Chem.*, 104, 8328-2339, 2000; Fan, H. et al., *Nature,* 405, 56-60, 2000 and Lu, Y. et al., *J. Am. Chem. Soc.*, 122, 5258-5261, 2000.
Figure 4A:
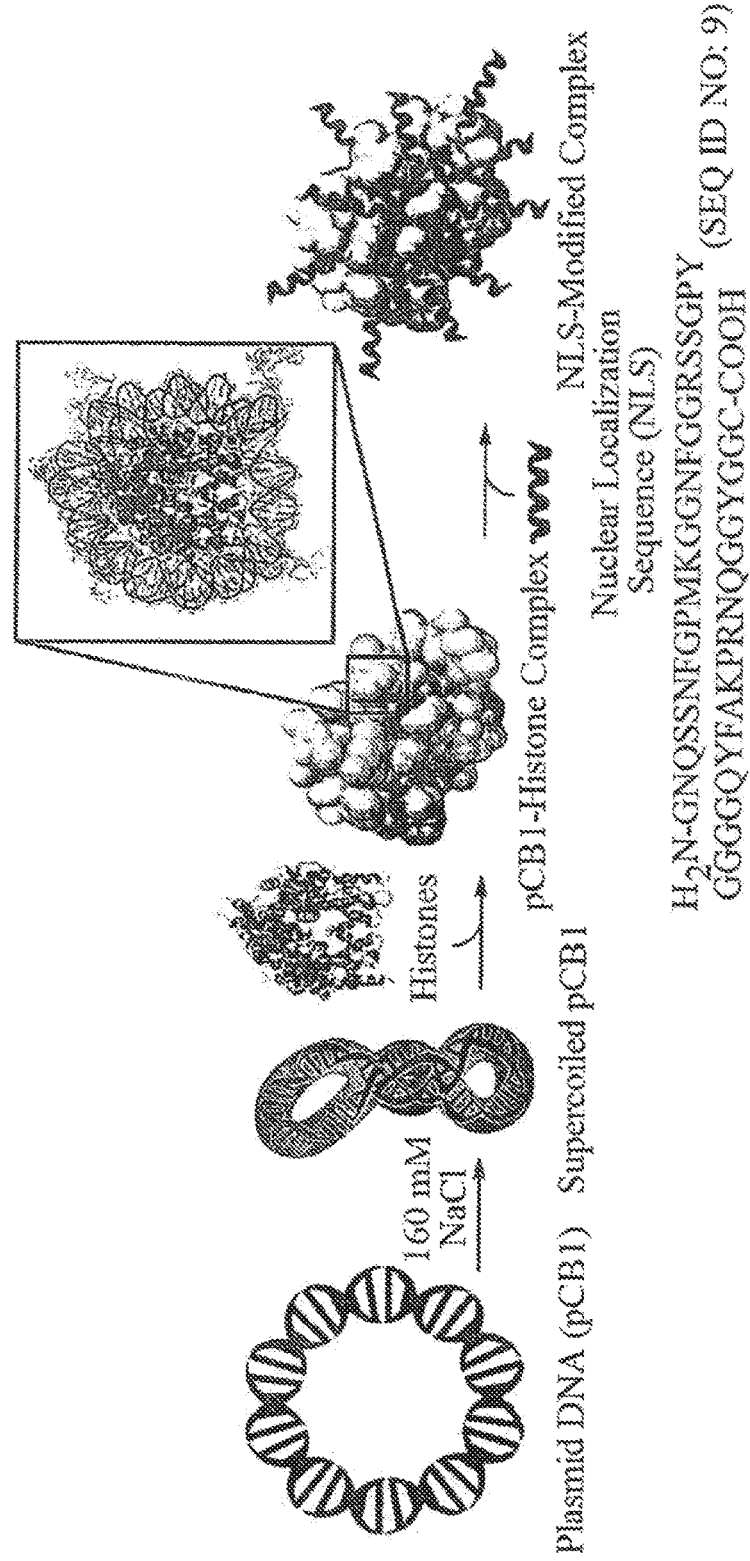
FIG. 4 depicts the packaging of the CB1 plasmid with histone proteins. (A) Schematic depicting the process used to supercoil the CB1 plasmid (pCB1), package supercoiled pCB1 with histones H1, H2A, H2B, H3, and H4, and modify the resulting pCB1-histone complex with a nuclear localization sequence (NLS) that promotes translocation through nuclear pores. (B) and (D) Atomic force microscopy (AFM) images of the CB1 plasmid (B) and histone-packaged pCB1 (D). Scale bars=100 nm. (C) and (E) Height profiles that correspond to the red lines in (B) and (D), respectively.
Figure 4B:
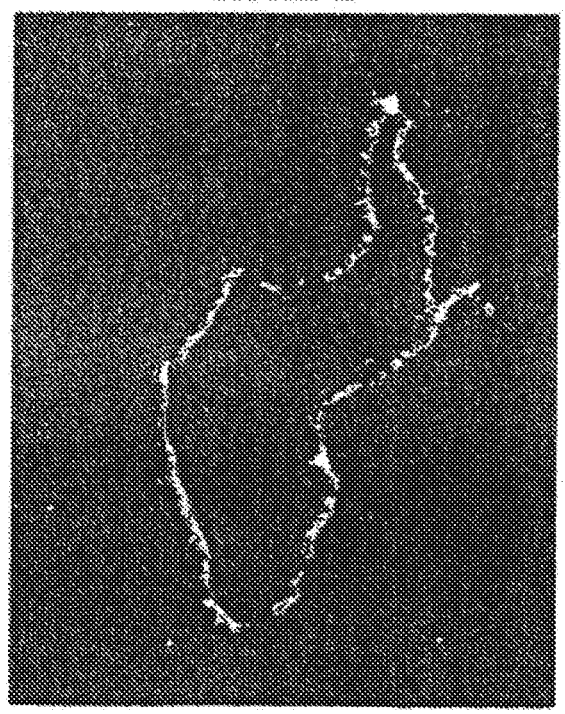
Figure 4D:
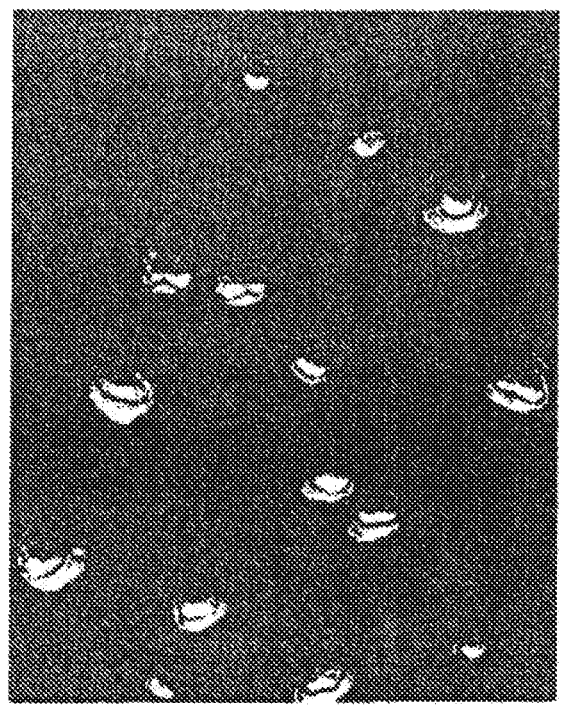
Figure 4E:
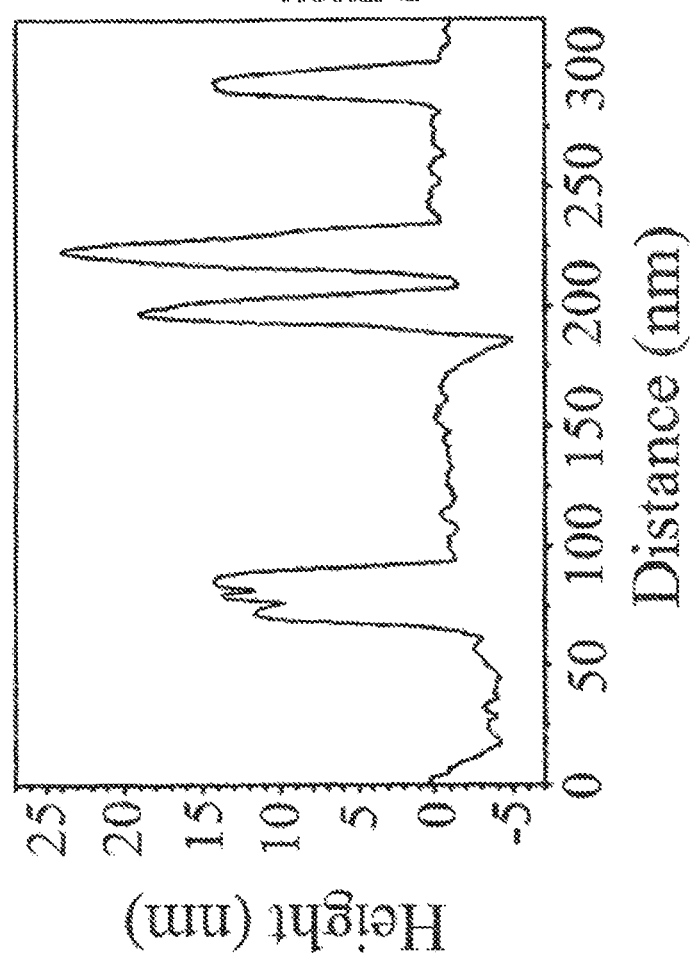

Pore surface chemistry of the nanoparticle material can be very diverse—all organosilanes yielding cationic, anionic, hydrophilic, hydrophobic, reactive groups—pore surface chemistry, especially charge and hydrohobicity, affect loading capacity. See FIG. 3, attached. Attractive electrostatic interactions or hydrophobic interactions control/enhance loading capacity and control release rates. Higher surface areas can lead to higher loadings of drugs/cargos through these attractive interactions. See below.

The surface area of nanoparticles, as measured by the N2 BET method, ranges from about 100 m2/g to >about 1200 m2/g. In general, the larger the pore size, the smaller the surface area. See FIG. 2B. The surface area theoretically could be reduced to essentially zero, if one does not remove the templating agent or if the pores are sub-0.5-nm and therefore not measurable by N2 sorption at 77K due to kinetic effects. However, in this case, they could be measured by CO2 or water sorption, but would probably be considered non-porous. This would apply if biomolecules are encapsulated directly in the silica cores prepared without templates, in which case particles (internal cargo) would be released by dissolution of the silica matrix after delivery to the cell.

Typically the protocells according to the present invention are loaded with cargo to a capacity up to about 50 weight %: defined as (cargo weight/weight of loaded protocell)×100. The optimal loading of cargo is often about 0.01 to 10% but this depends on the drug or drug combination which is incorporated as cargo into the protocell. This is generally expressed in µM per $10^{10}$ particles where we have values ranging from 2000-100 µM per $10^{10}$ particles. Preferred protocells according to the present invention exhibit release of cargo at pH about 5.5, which is that of the endosome, but are stable at physiological pH of 7 or higher (7.4).

The surface area of the internal space for loading is the pore volume whose optimal value ranges from about 1.1 to 0.5 cubic centimeters per gram (cc/g). Note that in the protocells according to one embodiment of the present invention, the surface area is mainly internal as opposed to the external geometric surface area of the nanoparticle.

The lipid bilayer supported on the porous particle according to one embodiment of the present invention has a lower melting transition temperature, i.e. is more fluid than a lipid bilayer supported on a non-porous support or the lipid bilayer in a liposome. This is sometimes important in achieving high affinity binding of targeting ligands at low peptide densities, as it is the bilayer fluidity that allows lateral diffusion and recruitment of peptides by target cell surface receptors. One embodiment provides for peptides to cluster, which facilitates binding to a complementary target.

In the present invention, the lipid bilayer may vary significantly in compositon. Ordinarily, any lipid or polymer which is may be used in liposomes may also be used in protocells. Preferred lipids are as otherwise described herein. Particularly preferred lipid bilayers for use in protocells according to the present invention comprise a mixtures of lipids (as otherwise described herein) at a weight ratio of 5% DOPE, 5% PEG, 30% cholesterol, 60% DOPC or DPPC (by weight).

The charge of the mesoporous silica NP core as measured by the Zeta potential may be varied monotonically from −50 to +50 mV by modification with the amine silane, 2-(aminoethyl) propyltrimethoxy-silane (AEPTMS) or other organosilanes. This charge modification, in turn, varies the loading of the drug within the cargo of the protocell. Generally, after fusion of the supported lipid bilayer, the zeta-potential is reduced to between about −10 mV and +5 mV, which is important for maximizing circulation time in the blood and avoiding non-specific interactions.

Depending on how the surfactant template is removed, e.g. calcination at high temperature (500° C.) versus extraction in acidic ethanol, and on the amount of AEPTMS incorporated in the silica framework, the silica dissolution rates can be varied widely. This in turn controls the release rate of the internal cargo. This occurs because molecules that are strongly attracted to the internal surface area of the pores diffuse slowly out of the particle cores, so dissolution of the particle cores controls in part the release rate.

Further characteristics of protocells according to an embodiment of the present invention are that they are stable at pH 7, i.e. they don't leak their cargo, but at pH 5.5, which is that of the endosome lipid or polymer coating becomes destabilized initiating cargo release. This pH-triggered release is important for maintaining stability of the protocell up until the point that it is internalized in the cell by endocytosis, whereupon several pH triggered events cause release into the endosome and consequently, the cytosol of the cell. Quantitative experimental evidence has shown that targeted protocells illicit only a weak immune response, because they do not support T-Cell help required for higher affinitiy IgG, a favorable result.

Protocells according to the present invention exhibits at least one or more a number of characteristics (depending upon the embodiment) which distinguish them from prior art protocells:

1) In contrast to the prior art, an embodiment of the present invention specifies nanoparticles whose average size (diameter) is less than about 200-nm—this size is engineered to enable efficient cellular uptake by receptor mediated endocytosis;
2) An embodiment of the present invention can specify both monodisperse and/or polydisperse sizes to enable control of biodistribution.
3) An embodiment of the present invention is directed to targeted nanoparticles that induce receptor mediated endocytosis.
4) An embodiment of the present invention induces dispersion of cargo into cytoplasm through the inclusion of fusogenic or endosomolytic peptides.
5) An embodiment of the present invention provides particles with pH triggered release of cargo.
6) An embodiment of the present invention exhibits controlled time dependent release of cargo (via extent of thermally induced crosslinking of silica nanoparticle matrix).
7) An embodiment of the present invention can exhibit time dependent pH triggered release.
8) An embodiment of the present invention can contain and provide cellular delivery of complex multiple cargoes.
9) An embodiment of the present invention shows the killing of target cancer cells.
10) An embodiment of the present invention shows diagnosis of target cancer cells.
11) An embodiment of the present invention shows selective entry of target cells.
12) An embodiment of the present invention shows selective exclusion from off-target cells (selectivity).
13) An embodiment of the present invention shows enhanced fluidity of the supported lipid bilayer.
14) An embodiment of the present invention exhibits sub-nanomolar and controlled binding affinity to target cells.
15) An embodiment of the present invention exhibits sub-nanomolar binding affinity with targeting ligand densities below concentrations found in the prior art.
16) An embodiment of the present invention can further distinguish the prior art with with finer levels of detail unavailable in the prior art.

The term "lipid" is used to describe the components which are used to form lipid bilayers on the surface of the nanoparticles which are used in the present invention. Various embodiments provide nanostructures which are constructed from nanoparticles which support a lipid bilayer(s). In embodiments according to the present invention, the nanostructures preferably include, for example, a core-shell structure including a porous particle core surrounded by a shell of lipid bilayer(s). The nanostructure, preferably a porous silica nanostructure as described above, supports the lipid bilayer membrane structure. In embodiments according to the invention, the lipid bilayer of the protocells can provide biocompatibility and can be modified to possess targeting species including, for example, targeting peptides, fusogenic peptides, antibodies, aptamers, and PEG (polyethylene glycol) to allow, for example, further stability of the protocells and/or a targeted delivery into a bioactive cell, in particular a cancer cell. PEG, when included in lipid bilayers, can vary widely in molecular weight (although PEG ranging from about 10 to about 100 units of ethylene glycol, about 15 to about 50 units, about 15 to about 20 units, about 15 to about 25 units, about 16 to about 18 units, etc, may be used and the PEG component which is generally conjugated to phospholipid through an amine group comprises about 1% to about 20%, preferably about 5% to about 15%, about 10% by weight of the lipids which are included in the lipid bilayer.

Numerous lipids which are used in liposome delivery systems may be used to form the lipid bilayer on nanoparticles to provide protocells according to the present invention. Virtually any lipid which is used to form a liposome may be used in the lipid bilayer which surrounds the nanoparticles to form protocells according to an embodiment of the present invention. Preferred lipids for use in the present invention include, for example, 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glycero-3-Phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof. Cholesterol, not technically a lipid, but presented as a lipid for purposes of an embodiment of the present invention given the fact that cholesterol may be an important component of the lipid bilayer of protocells according to an embodiment of the invention. Often cholesterol is incorporated into lipid bilayers of protocells in order to enhance structural integrity of the bilayer. These lipids are all readily available commercially from Avanti Polar Lipids, Inc. (Alabaster, Ala., USA). DOPE and DPPE are particularly useful for conjugating (through an appropriate crosslinker) peptides, polypeptides, including antibodies, RNA and DNA through the amine group on the lipid.

The term "reporter" is used to describe an imaging agent or moiety which is incorporated into the phospholipid bilayer or cargo of protocells according to an embodiment of the present invention and provides a signal which can be measured. The moiety may provide a fluorescent signal or may be a radioisotope which allows radiation detection, among others. Exemplary fluorescent labels for use in protocells (preferably via conjugation or adsorption to the lipid bilayer or silica core, although these labels may also be incorporated into cargo elements such as DNA, RNA, polypeptides and small molecules which are delivered to cells by the protocells, include Hoechst 33342 (350/461), 4',6-diamidino-2-phenylindole (DAPI, 356/451), Alexa Fluor® 405 carboxylic acid, succinimidyl ester (401/421), CellTracker™ Violet BMQC (415/516), CellTracker™ Green CMFDA (492/517), calcein (495/515), Alexa Fluor® 488 conjugate of annexin V (495/519), Alexa Fluor® 488 goat anti-mouse IgG (H+L) (495/519), Click-iT® AHA Alexa Fluor® 488 Protein Synthesis HCS Assay (495/519), LIVE/DEAD® Fixable Green Dead Cell Stain Kit (495/519), SYTOX® Green nucleic acid stain (504/523), MitoSOX™ Red mitochondrial superoxide indicator (510/580). Alexa Fluor® 532 carboxylic acid, succinimidyl ester(532/554), pHrodo™ succinimidyl ester (558/576), CellTracker™ Red CMTPX (577/602), Texas Red® 1,2-dihexadecanoyl-sn-glycero-3-phosphoethanolamine (Texas Red® DHPE, 583/608), Alexa Fluor® 647 hydrazide (649/666), Alexa Fluor® 647 carboxylic acid, succinimidyl ester (650/668), Ulysis™ Alexa Fluor® 647 Nucleic Acid Labeling Kit (650/670) and Alexa Fluor® 647 conjugate of annexin V (650/665). Moities which enhance the fluorescent signal or slow the fluorescent fading may also be incorporated and include SlowFade® Gold antifade reagent (with and without DAPI) and Image-iT® FX signal enhancer. All of these are well known in the art. Additional reporters include polypeptide reporters which may be expressed by plasmids (such as histone-packaged supercoiled DNA plasmids) and include polypeptide reporters such as fluorescent green protein and fluorescent red protein. Reporters pursuant to the present invention are utilized principally in diagnostic applications including diagnosing the existence or progression of cancer (cancer tissue) in a patient and or the progress of therapy in a patient or subject.

The term "histone-packaged supercoiled plasmid DNA" is used to describe a preferred component of protocells according to the present invention which utilize a preferred plasmid DNA which has been "supercoiled" (i.e., folded in on itself using a supersaturated salt solution or other ionic solution which causes the plasmid to fold in on itself and "supercoil" in order to become more dense for efficient packaging into the protocells). The plasmid may be virtually any plasmid which expresses any number of polypeptides or encode RNA, including small hairpin RNA/shRNA or small interfering RNA/siRNA, as otherwise described herein. Once supercoiled (using the concentrated salt or other anionic solution), the supercoiled plasmid DNA is then complexed with histone proteins to produce a histone-packaged "complexed" supercoiled plasmid DNA.

"Packaged" DNA herein refers to DNA that is loaded into protocells (either adsorbed into the pores or confined directly within the nanoporous silica core itself). To minimize the DNA spatially, it is often packaged, which can be accomplished in several different ways, from adjusting the charge of the surrounding medium to creation of small complexes of the DNA with, for example, lipids, proteins, or other nanoparticles (usually, although not exclusively cationic). Packaged DNA is often achieved via lipoplexes (i.e. complexing DNA with cationic lipid mixtures). In addition, DNA has also been packaged with cationic proteins (including proteins other than histones), as well as gold nanoparticles (e.g. NanoFlares—an engineered DNA and metal complex in which the core of the nanoparticle is gold).

Any number of histone proteins, as well as other means to package the DNA into a smaller volume such as normally cationic nanoparticles, lipids, or proteins, may be used to package the supercoiled plasmid DNA "histone-packaged supercoiled plasmid DNA", but in therapeutic aspects which relate to treating human patients, the use of human histone proteins are preferably used. In certain aspects of the invention, a combination of human histone proteins H1, H2A, H2B, H3 and H4 in a preferred ratio of 1:2:2:2:2, although other histone proteins may be used in other, similar ratios, as is known in the art or may be readily practiced pursuant to the teachings of the present invention. The DNA may also be double stranded linear DNA, instead of plasmid DNA, which also may be optionally supercoiled and/or packaged with histones or other packaging components.

Other histone proteins which may be used in this aspect of the invention include, for example, H1F, H1F0, H1FNT, H1FOO, H1FX H1H1 HIST1H1A, HIST1H1B, HIST1H1C, HIST1H1D, HIST1H1E, HIST1H1T; H2AF, H2AFB1, H2AFB2, H2AFB3, H2AFJ, H2AFV, H2AFX, H2AFY, H2AFY2, H2AFZ, H2A1, HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, H2A2, HIST2H2AA3, HIST2H2AC, H2BF, H2BFM, HSBFS, HSBFWT, H2B1, HIST1H2BA, HIST1HSBB, HIST1HSBC, HIST1HSBD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, H2B2, HIST2H2BE, H3A1, HIST1H3A, HIST1H3B, HIST1H3C, HIST1H3D, HIST1H3E, HIST1H3F, HIST1H3G, HIST1H3H, HIST1H3I, HIST1H3J, H3A2, HIST2H3C, H3A3, HIST3H3, H41, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, H44 and HIST4H4.

The term "nuclear localization sequence" refers to a peptide sequence incorporated or otherwise crosslinked into histone proteins which comprise the histone-packaged supercoiled plasmid DNA. In certain embodiments, protocells according to the present invention may further comprise a plasmid (often a histone-packaged supercoiled plasmid DNA) which is modified (crosslinked) with a nuclear localization sequence (note that the histone proteins may be crosslinked with the nuclear localization sequence or the plasmid itself can be modified to express a nuclear localization sequence) which enhances the ability of the histone-packaged plasmid to penetrate the nucleus of a cell and deposit its contents there (to facilitate expression and ultimately cell death. These peptide sequences assist in carrying the histone-packaged plasmid DNA and the associated histones into the nucleus of a targeted cell whereupon the plasmid will express peptides and/or nucleotides as desired to deliver therapeutic and/or diagnostic molecules (polypeptide and/or nucleotide) into the nucleus of the targeted cell. Any number of crosslinking agents, well known in the art, may be used to covalently link a nuclear localization sequence to a histone protein (often at a lysine group or other group which has a nucleophilic or electrophilic group in the side chain of the amino acid exposed pendant to the polypeptide) which can be used to introduce the histone packaged plasmid into the nucleus of a cell. Alternatively, a nucleotide sequence which expresses the nuclear localization sequence can be positioned in a plasmid in proximity to that which expresses histone protein such that the expression of the histone protein conjugated to the nuclear localization sequence will occur thus facilitating transfer of a plasmid into the nucleus of a targeted cell.

Proteins gain entry into the nucleus through the nuclear envelope. The nuclear envelope consists of concentric membranes, the outer and the inner membrane. These are the gateways to the nucleus. The envelope consists of pores or large nuclear complexes. A protein translated with a NLS will bind strongly to importin (aka karyopherin), and together, the complex will move through the nuclear pore. Any number of nuclear localization sequences may be used to introduce histone-packaged plasmid DNA into the nucleus of a cell. Preferred nuclear localization sequences include $H_2N$-GNQSSNFGPMKGGNFGGRSS-GPYGGGGQYFAKPRNQGGYGGC-COOH SEQ I.D NO: 9, RRMKWKK (SEQ ID NO:10), PKKKRKV (SEQ ID NO: 11), and KR[PAATKKAGQA]KKKK (SEQ ID NO:12), the NLS of nucleoplasmin, a prototypical bipartite signal comprising two clusters of basic amino acids, separated by a spacer of about 10 amino acids. Numerous other nuclear localization sequences are well known in the art. See, for example, LaCasse, et al., *Nuclear localization signals overlap DNA-or RNA-binding domains in nucleic acid-binding proteins. Nucl. Acids Res.,* 23, 1647-1656 1995); Weis, K. *Importins and exportins: how to get in and out of the nucleus [published erratum appears in Trends Biochem Sci* 1998 July; 23(7):235*]. TIBS,* 23, 185-9 (1998); and Murat Cokol, Raj Nair & Burkhard Rost, "Finding nuclear localization signals", at the website ubic.bioc.columbia.edu/papers/2000 nls/paper.html#tab2.

The term "cancer" is used to describe a proliferation of tumor cells (neoplasms) having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of dysplasia, or loss of differentiation and orientation of cells, and have the properties of invasion and metastasis. The term cancer also within context, includes drug resistant cancers, including multiple drug resistant cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver (hepatocellular), lung, nasopharyngeal, neck, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germline tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. It is noted that certain tumors including hepatocellular and cervical cancer, among others, are shown to exhibit increased levels of MET receptors specifically on cancer cells and are a principal target for compositions and therapies according to embodiments of the present invention which include a MET binding peptide complexed to the protocell.

The terms "coadminister" and "coadministration" are used synonymously to describe the administration of at least one of the protocell compositions according to the present invention in combination with at least one other agent, often at least one additional anti-cancer agent (as otherwise described herein), which are specifically disclosed herein in amounts or at concentrations which would be considered to be effective amounts at or about the same time. While it is preferred that coadministered compositions/agents be administered at the same time, agents may be administered at times such that effective concentrations of both (or more) compositions/agents appear in the patient at the same time for at least a brief period of time. Alternatively, in certain aspects of the present invention, it may be possible to have each co administered composition/agent exhibit its inhibitory effect at different times in the patient, with the ultimate result being the inhibition and treatment of cancer, especially including hepatoccellular or cellular cancer as well as the reduction or inhibition of other disease states, conditions or complications. Of course, when more than disease state, infection or other condition is present, the present compounds may be combined with other agents to treat that other infection or disease or condition as required.

The term "anti-cancer agent" is used to describe a compound which can be formulated in combination with one or more compositions comprising protocells according to the present invention and optionally, to treat any type of cancer, in particular hepatocellular or cervical cancer, among numerous others. Anti-cancer compounds which can be formulated with compounds according to the present invention include, for example, Exemplary anti-cancer agents which may be used in the present invention include, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 345-(methylsulfonylpiperadinemethyl)-indolylj-quinolone, vatalanib, AG-013736, AVE-0005, the acetate salt of [D-Ser(Bu t)6, Azgly 10] (pyro-Glu-His-Trp-Ser-Tyr-D-Ser(Bu t)-Leu-Arg-Pro-Azgly-$NH_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, woitmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "antihepatocellular cancer agent" is used throughout the specification to describe an anticancer agent which may be used to inhibit, treat or reduce the likelihood of hepatocellular cancer, or the metastasis of that cancer. Anticancer agents which may find use in the present invention include for example, nexavar (sorafenib), sunitinib, bevacizumab, tarceva (erlotinib), tykerb (lapatinib) and mixtures thereof. In addition, other anticancer agents may also be used in the present invention, where such agents are found to inhibit metastasis of cancer, in particular, hepatocellular cancer.

The term "antiviral agent" is used to describe a bioactive agent/drug which inhibits the growth and/or elaboration of a virus, including mutant strains such as drug resistant viral strains. Preferred antiviral agents include anti-HIV agents, anti-HBV agents and anti-HCV agents. In certain aspects of the invention, especially where the treatment of hepatocellular cancer is the object of therapy, the inclusion of an anti-hepatitis C agent or anti-hepatitis B agent may be combined with other traditional anticancer agents to effect therapy, given that hepatitis B virus (HBV) and/or hepatitis C virus (HCV) is often found as a primary or secondary infection or disease state associated with hepatocellular cancer. Anti-HBV agents which may be used in the present invention, either as a cargo component in the protocell or as an additional bioactive agent in a pharmaceutical composition which includes a population of protocells includes such agents as Hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Typical anti-HCV agents for use in the invention include such agents as boceprevir, daclatasvir, asunapavir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, ribavirin, pegylated interferon, PHX1766, SP-30 and mixtures thereof.

The term "anti-HIV agent" refers to a compound which inhibits the growth and/or elaboration of HIV virus (I and/or II) or a mutant strain thereof. Exemplary anti-HIV agents for use in the present invention which can be included as cargo in protocells according to the present invention include, for example, including nucleoside reverse transcriptase inhibitors (NRTI), other non-nucloeoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof.

The term "targeting active species" is used to describe a compound or moiety which is complexed or preferably covalently bonded to the surface of a protocell according to the present invention which binds to a moiety on the surface of a cell to be targeted so that the protocell may selectively bind to the surface of the targeted cell and deposit its contents into the cell. The targeting active species for use in the present invention is preferably a targeting peptide as otherwise described herein, a polypeptide including an antibody or antibody fragment, an aptamer, or a carbohydrate, among other species which bind to a targeted cell.

The term "targeting peptide" is used to describe a preferred targeting active species which is a peptide of a particular sequence which binds to a receptor or other polypeptide in cancer cells and allows the targeting of protocells according to the present invention to particular cells which express a peptide (be it a receptor or other functional polypeptide) to which the targeting peptide binds. In the present invention, exemplary targeting peptides include, for example, SP94 free peptide (H$_2$N-SFSIILT-PILPL-COOH, SEQ ID NO: 6), SP94 peptide modified with a C-terminal cysteine for conjugation with a crosslinking agent (H$_2$N-SFSIILTPILPLGGC-COOH, SEQ ID NO: 7), a modified SP94 peptide (H$_2$N-SFSIILTPILPLEEEGGC-COOH, SEQ ID NO: 8) or a MET binding peptide as otherwise disclosed herein. Other targeting peptides are known in the art. Targeting peptides may be complexed or preferably, covalently linked to the lipid bilayer through use of a crosslinking agent as otherwise described herein.

The term "MET binding peptide" or "MET receptor binding peptide" is used to describe five (5) 7-mer peptides which have been shown to bind MET receptors on the surface of cancer cells with enhanced binding efficiency. Pursuant to the present invention, several small peptides with varying amino acid sequences were identified which bind the MET receptor (a.k.a. hepatocyte growth factor receptor, expressed by gene c-MET) with varying levels of specificity and with varying ability to activate MET receptor signaling pathways. 7-mer peptides were identified using phage display biopanning, with examples of resulting sequences which evidence enhanced binding to MET receptor and consequently to cells such as cancer cells (e.g. hepatocellular, ovarian and cervical) which express high levels of MET receptors, which appear below. Binding data for several of the most commonly observed sequences during the biopanning process is also presented in the examples section of the present application. These peptides are particularly useful as targeting ligands for cell-specific therapeutics. However, peptides with the ability to activate the receptor pathway may have additional therapeutic value themselves or in combination with other therapies. Many of the peptides have been found bind not only hepatocellular carcinoma, which was the original intended target, but also to bind a wide variety of other carcinomas including ovarian and cervical cancer. These peptides are believed to have wide-ranging applicability for targeting or treating a variety of cancers and other physiological problems associated with expression of MET and associated receptors.

The following five 7 mer peptide sequences show substantial binding to MET receptor and are particularly useful as targeting peptides for use on protocells according to the the present invention.

SEQ ID NO: 1
ASVHFPP (Ala-Ser-Val-His-Phe-Pro-Pro)

SEQ ID NO: 2
TATFWFQ (Thr-Ala-Thr-Phe-Trp-Phe-Gln)

-continued

SEQ ID NO: 3
TSPVALL (Thr-Ser-Pro-Val-Ala-Leu-Leu)

SEQ ID NO: 4
IPLKVHP (Ile-Pro-Leu-Lys-Val-His-Pro)

SEQ ID NO: 5
WPRLTNM (Trp-Pro-Arg-Leu-Thr-Asn-Met)

Each of these peptides may be used alone or in combination with other MET peptides within the above group or with other targeting peptides which may assist in binding protocells according to the present invention to cancer cells, including hepatocellular cancer cells, ovarian cancer cells and cervical cancer cells, among numerous others. These binding peptides may also be used in pharmaceutical compounds alone as MET binding peptides to treat cancer and otherwise inhibit hepatocyte growth factor binding.

The terms "fusogenic peptide" and "endosomolytic peptide" are used synonymously to describe a peptide which is optionally and preferred crosslinked onto the lipid bilayer surface of the protocells according to the present invention. Fusogenic peptides are incorporated onto protocells in order to facilitate or assist escape from endosomal bodies and to facilitate the introduction of protocells into targeted cells to effect an intended result (therapeutic and/or diagnostic as otherwise described herein). Representative and preferred fusogenic peptides for use in protocells according to the present invention include H5WYG peptide, H$_2$N-GLFHA-IAHFIHGGWHGLIHGWYGGC-COOH (SEQ ID. NO: 13) or an 8 mer polyarginine (H$_2$N-RRRRRRRR-COOH, SEQ ID NO:14), among others known in the art.

The term "crosslinking agent" is used to describe a bifunctional compound of varying length containing two different functional groups which may be used to covalently link various components according to the present invention to each other. Crosslinking agents according to the present invention may contain two electrophilic groups (to react with nucleophilic groups on peptides of oligonucleotides, one electrophilic group and one nucleophilic group or two nucleophlic groups). The crosslinking agents may vary in length depending upon the components to be linked and the relative flexibility required. Crosslinking agents are used to anchor targeting and/or fusogenic peptides to the phospholipid bilayer, to link nuclear localization sequences to histone proteins for packaging supercoiled plasmid DNA and in certain instances, to crosslink lipids in the lipid bilayer of the protocells. There are a large number of crosslinking agents which may be used in the present invention, many commercially available or available in the literature. Preferred crosslinking agents for use in the present invention include, for example, 1-Ethyl-3-[3-dimethylaminopropyl]carbodiimide hydrochloride (EDC), succinimidyl 4-[N-maleimidomethyl]cyclohexane-1-carboxylate (SMCC), N-[β-Maleimidopropionic acid] hydrazide (BMPH), NHS-(PEG)$_n$-maleimide, succinimidyl-[(N-maleimidopropionamido)-tetracosaethyleneglycol] ester (SM(PEG)$_{24}$), and succinimidyl 6-[3'-(2-pyridyldithio)-propionamido]hexanoate (LC-SPDP), among others.

As discussed in detail above, the porous nanoparticle core of the present invention can include porous nanoparticles having at least one dimension, for example, a width or a diameter of about 3000 nm or less, about 1000 nm or less, about 500 nm or less, about 200 nm or less. Preferably, the nanoparticle core is spherical with a preferred diameter of about 500 nm or less, more preferably about 8-10 nm to about 200 nm. In embodiments, the porous particle core can have various cross-sectional shapes including a circular, rectangular, square, or any other shape. In certain embodiments, the porous particle core can have pores with a mean pore size ranging from about 2 nm to about 30 nm, although the mean pore size and other properties (e.g., porosity of the porous particle core) are not limited in accordance with various embodiments of the present teachings.

In general, protocells according to the present invention are biocompatible. Drugs and other cargo components are often loaded by adsorption and/or capillary filling of the pores of the particle core up to approximately 50% by weight of the final protocell (containing all components). In certain embodiments according to the present invention, the loaded cargo can be released from the porous surface of the particle core (mesopores), wherein the release profile can be determined or adjusted by, for example, the pore size, the surface chemistry of the porous particle core, the pH value of the system, and/or the interaction of the porous particle core with the surrounding lipid bilayer(s) as generally described herein.

In the present invention, the porous nanoparticle core used to prepare the protocells can be tuned in to be hydrophilic or progressively more hydrophobic as otherwise described herein and can be further treated to provide a more hydrophilic surface. For example, mesoporous silica particles can be further treated with ammonium hydroxide and hydrogen peroxide to provide a higher hydrophilicity. In preferred aspects of the invention, the lipid bilayer is fused onto the porous particle core to form the protocell. Protocells according to the present invention can include various lipids in various weight ratios, preferably including 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glycero-3-Phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof.

The lipid bilayer which is used to prepare protocells according to the present invention can be prepared, for example, by extrusion of hydrated lipid films through a filter with pore size of, for example, about 100 nm, using standard protocols known in the art or as otherwise described herein. The filtered lipid bilayer films can then be fused with the porous particle cores, for example, by pipette mixing. In certain embodiments, excess amount of lipid bilayer or lipid bilayer films can be used to form the protocell in order to improve the protocell colloidal stability.

In certain diagnostic embodiments, various dyes or fluorescent (reporter) molecules can be included in the protocell cargo (as expressed by as plasmid DNA) or attached to the porous particle core and/or the lipid bilayer for diagnostic purposes. For example, the porous particle core can be a silica core or the lipid bilayer and can be covalently labeled with FITC (green fluorescence), while the lipid bilayer or the particle core can be covalently labeled with FITC Texas red (red fluorescence). The porous particle core, the lipid bilayer and the formed protocell can then be observed by, for example, confocal fluorescence for use in diagnostic applications. In addition, as discussed herein, plasmid DNA can be used as cargo in protocells according to the present invention such that the plasmid may express one or more fluorescent proteins such as fluorescent green protein or fluorescent red protein which may be used in diagnostic applications.

In various embodiments, the protocell is used in a synergistic system where the lipid bilayer fusion or liposome fusion (i.e., on the porous particle core) is loaded and sealed with various cargo components with the pores (mesopores) of the particle core, thus creating a loaded protocell useful for cargo delivery across the cell membrane of the lipid bilayer or through dissolution of the porous nanoparticle, if applicable. In certain embodiments, in addition to fusing a single lipid (e.g., phospholipids) bilayer, multiple bilayers with opposite charges can be successively fused onto the porous particle core to further influence cargo loading and/or sealing as well as the release characteristics of the final protocell A fusion and synergistic loading mechanism can be included for cargo delivery. For example, cargo can be loaded, encapsulated, or sealed, synergistically through liposome fusion on the porous particles. The cargo can include, for example, small molecule drugs (e.g. especially including anticancer drugs and/or antiviral drugs such as anti-HBV or anti-HCV drugs), peptides, proteins, antibodies, DNA (especially plasmid DNA, including the preferred histone-packaged super coiled plasmid DNA), RNAs (including shRNA and siRNA (which may also be expressed by the plasmid DNA incorporated as cargo within the protocells) fluorescent dyes, including fluorescent dye peptides which may be expressed by the plasmid DNA incorporated within the protocell.

In embodiments according to the present invention, the cargo can be loaded into the pores (mesopores) of the porous particle cores to form the loaded protocell. In various embodiments, any conventional technology that is developed for liposome-based drug delivery, for example, targeted delivery using PEGylation, can be transferred and applied to the protocells of the present invention.

As discussed above, electrostatics and pore size can play a role in cargo loading. For example, porous silica nanoparticles can carry a negative charge and the pore size can be tunable from about 2 nm to about 10 nm or more. Negatively charged nanoparticles can have a natural tendency to adsorb positively charged molecules and positively charged nanoparticles can have a natural tendency to adsorb negatively charged molecules. In various embodiments, other properties such as surface wettability (e.g., hydrophobicity) can also affect loading cargo with different hydrophobicity.

In various embodiments, the cargo loading can be a synergistic lipid-assisted loading by tuning the lipid composition. For example, if the cargo component is a negatively charged molecule, the cargo loading into a negatively charged silica can be achieved by the lipid-assisted loading. In certain embodiments, for example, a negatively species can be loaded as cargo into the pores of a negatively charged silica particle when the lipid bilayer is fused onto the silica surface showing a fusion and synergistic loading mechanism. In this manner, fusion of a non-negatively charged (i.e., positively charged or neutral) lipid bilayer or liposome on a negatively charged mesoporous particle can serve to load the particle core with negatively charged cargo components. The negatively charged cargo components can be concentrated in the loaded protocell having a concentration exceed about 100 times as compared with the charged cargo components in a solution. In other embodiments, by varying the charge of the mesoporous particle and the lipid bilayer, positively charged cargo components can be readily loaded into protocells.

Once produced, the loaded protocells can have a cellular uptake for cargo delivery into a desirable site after administration. For example, the cargo-loaded protocells can be administered to a patient or subject and the protocell comprising a targeting peptide can bind to a target cell and be internalized or uptaken by the target cell, for example, a cancer cell in a subject or patient. Due to the internalization of the cargo-loaded protocells in the target cell, cargo components can then be delivered into the target cells. In certain embodiments the cargo is a small molecule, which can be delivered directly into the target cell for therapy. In other embodiments, negatively charged DNA or RNA (including shRNA or siRNA), especially including a DNA plasmid which is preferably formulated as histone-packaged supercoiled plasmid DNA preferably modified with a nuclear localization sequence can be directly delivered or internalized by the targeted cells. Thus, the DNA or RNA can be loaded first into a protocell and then into then through the target cells through the internalization of the loaded protocells.

As discussed, the cargo loaded into and delivered by the protocell to targeted cells includes small molecules or drugs (especially anti-cancer or anti-HBV and/or anti-HCV agents), bioactive macromolecules (bioactive polypeptides such as ricin toxin A-chain or diphtheria toxin A-chain or RNA molecules such as shRNA and/or siRNA as otherwise described herein) or histone-packaged supercoiled plasmid DNA which can express a therapeutic or diagnostic peptide or a therapeutic RNA molecule such as shRNA or siRNA, wherein the histone-packaged supercoiled plasmid DNA is optionally and preferably modified with a nuclear localization sequence which can localize and concentrate the delivered plasmid DNA into the nucleus of the target cell. As such, loaded protocells can deliver their cargo into targeted cells for therapy or diagnostics.

In various embodiments according to the present invention, the protocells and/or the loaded protocells can provide a targeted delivery methodology for selectively delivering the protocells or the cargo components to targeted cells (e.g., cancer cells). For example, a surface of the lipid bilayer can be modified by a targeting active species that corresponds to the targeted cell. The targeting active species may be a targeting peptide as otherwise described herein, a polypeptide including an antibody or antibody fragment, an aptamer, a carbohydrate or other moiety which binds to a targeted cell. In preferred aspects of the invention, the targeting active species is a targeting peptide as otherwise described herein. In certain embodiments, preferred peptide targeting species include a MET binding peptide as otherwise described herein.

For example, by providing a targeting active species (preferably, a targeting peptide) on the surface of the loaded protocell, the protocell selectively binds to the targeted cell in accordance with the present teachings. In one embodiment, by conjugating an exemplary targeting peptide SP94 or analog or a MET binding peptide as otherwise described herein that targets cancer cells, including cancer liver cells to the lipid bilayer, a large number of the cargo-loaded protocells can be recognized and internalized by this specific cancer cells due to the specific targeting of the exemplary SP94 or MET binding peptide with the cancer (including liver) cells. In most instances, if the protocells are conjugated with the targeting peptide, the protocells will selectively bind to the cancer cells and no appreciable binding to the non-cancerous cells occurs.

Once bound and taken up by the target cells, the loaded protocells can release cargo components from the porous particle and transport the released cargo components into the target cell. For example, sealed within the protocell by the liposome fused bilayer on the porous particle core, the cargo components can be released from the pores of the lipid bilayer, transported across the protocell membrane of the lipid bilayer and delivered within the targeted cell. In embodiments according to the present invention, the release profile of cargo components in protocells can be more controllable as compared with when only using liposomes as known in the prior art. The cargo release can be determined by, for example, interactions between the porous core and the lipid bilayer and/or other parameters such as pH value of the system. For example, the release of cargo can be achieved through the lipid bilayer, through dissolution of the porous silica; while the release of the cargo from the protocells can be pH-dependent.

In certain embodiments, the pH value for cargo is often less than 7, preferably about 4.5 to about 6.0, but can be about pH 14 or less. Lower pHs tend to facilitate the release of the cargo components significantly more than compared with high pHs. Lower pHs tend to be advantageous because the endosomal compartments inside most cells are at low pHs (about 5.5), but the rate of delivery of cargo at the cell can be influenced by the pH of the cargo. Depending upon the cargo and the pH at which the cargo is released from the protocell, the release of cargo can be relative short (a few hours to a day or so) or a span for several days to about 20-30 days or longer. Thus, the present invention may accommodate immediate release and/or sustained release applications from the protocells themselves.

In certain embodiments, the inclusion of surfactants can be provided to rapidly rupture the lipid bilayer, transporting the cargo components across the lipid bilayer of the protocell as well as the targeted cell. In certain embodiments, the phospholipid bilayer of the protocells can be ruptured by the application/release of a surfactant such as sodium dodecyl sulfate (SDS), among others to facilitate a rapid release of cargo from the protocell into the targeted cell. In certain embodiments, the rupture of the lipid bilayer can in turn induce immediate and complete release of the cargo components from the pores of the particle core of the protocells. In this manner, the protocell platform can provide versatile delivery systems as compared with other delivery systems in the art. For example, when compared to delivery systems using nanoparticles only, the disclosed protocell platform can provide a simple system and can take advantage of the low toxicity and immunogenicity of liposomes or lipid bilayers along with their ability to be PEGylated or to be conjugated to extend circulation time and effect targeting. In another example, when compared to delivery systems using liposome only, the protocell platform can provide a more stable system and can take advantage of the mesoporous core to control the loading and/or release profile.

In addition, the lipid bilayer and its fusion on porous particle core can be fine-tuned to control the loading, release, and targeting profiles and can further comprise fusogenic peptides and related peptides to facilitate delivery of the protocells for greater therapeutic and/or diagnostic effect. Further, the lipid bilayer of the protocells can provide a fluidic interface for ligand display and multivalent targeting, which allows specific targeting with relatively low surface ligand density due to the capability of ligand reorganization on the fluidic lipid interface. Furthermore, the disclosed protocells can readily enter targeted cells while empty liposomes without the support of porous particles cannot be internalized by the cells.

Pharmaceutical compositions according to the present invention comprise an effective population of protocells as otherwise described herein formulated to effect an intended result (e.g. therapeutic result and/or diagnostic analysis, including the monitoring of therapy) formulated in combination with a pharmaceutically acceptable carrier, additive or excipient. The protocells within the population of the composition may be the same or different depending upon the desired result to be obtained. Pharmaceutical compositions according to the present invention may also comprise an addition bioactive agent or drug, such as an anticancer agent or an antiviral agent, for example, an anti-HIV, anti-HBV or an anti-HCV agent.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, intrathecal or intramuscular injection, among others, including buccal, rectal and transdermal administration. Subjects contemplated for treatment according to the method of the invention include humans, companion animals, laboratory animals, and the like. The invention contemplates immediate and/or sustained/controlled release compositions, including compositions which comprise both immediate and sustained release formulations. This is particularly true when different populations of protocells are used in the pharmaceutical compositions or when additional bioactive agent(s) are used in combination with one or more populations of protocells as otherwise described herein.

Formulations containing the compounds according to the present invention may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients.

An injectable composition for parenteral administration (e.g. intravenous, intramuscular or intrathecal) will typically contain the compound in a suitable i.v. solution, such as sterile physiological salt solution. The composition may also be formulated as a suspension in an aqueous emulsion.

Liquid compositions can be prepared by dissolving or dispersing the population of protocells (about 0.5% to about 20% by weight or more), and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject according to the present invention.

Methods of treating patients or subjects in need for a particular disease state or infection (especially including cancer and/or a HBV, HCV or HIV infection) comprise administration an effective amount of a pharmaceutical composition comprising therapeutic protocells and optionally at least one additional bioactive (e.g. antiviral) agent according to the present invention.

Diagnostic methods according to the present invention comprise administering to a patient in need (a patient suspected of having cancer) an effective amount of a population of diagnostic protocells (e.g., protocells which comprise a target species, such as a targeting peptide which binds selectively to cancer cells and a reporter component to indicate the binding of the protocells to cancer cells if the cancer cells are present) whereupon the binding of protocells to cancer cells as evidenced by the reporter component (moiety) will enable a diagnosis of the existence of cancer in the patient.

An alternative of the diagnostic method of the present invention can be used to monitor the therapy of cancer or other disease state in a patient, the method comprising administering an effective population of diagnostic protocells (e.g., protocells which comprise a target species, such as a targeting peptide which binds selectively to cancer cells or other target cells and a reporter component to indicate the binding of the protocells to cancer cells if the cancer cells are present) to a patient or subject prior to treatment, determining the level of binding of diagnostic protocells to target cells in said patient and during and/or after therapy, determining the level of binding of diagnostic protocells to target cells in said patient, whereupon the difference in binding before the start of therapy in the patient and during and/or after therapy will evidence the effectiveness of therapy in the patient, including whether the patient has completed therapy or whether the disease state has been inhibited or eliminated (including remission of a cancer).

The following non-limiting examples are illustrative of the invention and its advantageous properties, and are not to be taken as limiting the disclosure or claims in any way. In the examples, as well as elsewhere in this application, all parts and percentages are by weight unless otherwise indicated.

Examples

As provided in the following examples, the porous nanoparticle-supported lipid bilayer (protocell), formed via fusion of liposomes to nanoporous silica particles, is a novel type of nanocarrier that addresses multiple challenges associated with targeted delivery of cancer therapeutics and diagnostics. Like liposomes, protocells are biocompatible, biodegradable, and non-immunogenic, but their nanoporous silica core confers a drastically enhanced cargo capacity and prolonged bilayer stability when compared to similarly-sized liposomal delivery agents. The porosity and surface chemistry of the core can, furthermore, be modulated to promote encapsulation of a wide variety of therapeutic agents, such as drugs, nucleic acids, and protein toxins. The rate of cargo release can be controlled by pore size and the overall degree of silica condensation, making protocells useful in applications requiring either burst or controlled release profiles. Finally, the protocell's supported lipid bilayer (SLB) can be modified with ligands to promote selective delivery and with PEG to extend circulation times. In the examples, the inventors report the use of peptide targeted protocells to achieve highly specific delivery of a plasmid that encodes small hairpin RNA (shRNA), which induces growth arrest and apoptosis of transfected cells by silencing cyclin B1. As set forth in the examples section below, the inventors have prepared synthesized silica nanoparticles with pores large enough to accommodate histone-packaged plasmids using a dual surfactant approach. A non-ionic surfactant (Pluronic® F-127), when employed in conjunction with a swelling agent (1,3,5-trimethylbenzene) served as the template for large pores, while a fluorocarbon surfactant (FC-4) promoted growth of the silica core. Resulting particles had diameters ranging from 100-nm to 300-nm and contained an ordered network of 20-nm pores with 17.3-nm pore entrances. Supercoiled plasmid DNA was packaged with histones, and the resulting complex (about 15-nm in diameter) was modified with a nuclear localization sequence (NLS) prior to being loaded into the silica core. Fusion of liposomes to the nanoporous core promoted long-term retention (>1 month) of encapsulated DNA upon exposure to simulated body fluids at 37° C. Using phage display, the inventors identified a targeting peptide with nanomolar affinity for hepatocyte growth factor receptor (c-Met), which is known to be overexpressed by various types of hepatocellular carcinoma (HCC). Protocells loaded with the DNA-histone-NLS complex and modified with "240 copies each of the targeting peptide and a fusogenic peptide that promotes endosomal escape of protocells and encapsulated DNA were capable of transfecting both dividing and non-dividing HCC. Furthermore, targeted protocells effectively induced GJM arrest and apoptosis of HCC (LC, =25 nM) without affecting the viability of non-cancerous cells, including hepatocytes, endothelial cells, and immune cells (PBMCs, B cells, and T cells).

Methods

The nanoporous silica particles that form the core of the protocell are prepared, as previously described[1,2] (see also Ashley, et al., *Nature Materials,* 2011, May; 10(5):389-97) from a homogenous mixture of water-soluble silica precursor(s) and amphipathic surfactant(s) using either aerosol-assisted evaporation-induced self-assembly (EISA) or solvent extraction-driven self-assembly within water-in-oil emulsion droplets[1]. Solvent evaporation or extraction concentrates the aerosol or emulsion droplets in surfactant(s), which directs the formation of periodic, ordered structures, around which silica assembles and condenses. Surfactants are removed via thermal calcination, which results in porous nanoparticles with well-defined, uniform pore sizes and topologies. Particles formed via aerosol-assisted EISA ('unimodal' particles) possess an average diameter of approximately 120-nm (after size exclusion-based separation), a Brunauer-Emmer-Teller (BET) surface area in excess of 1200 $m^2/g$, a pore volume fraction of about 50%, and a unimodal pore diameter of 2.5-nm. Particles formed within emulsion droplets ('multimodal' particles) have an average diameter of ~150 nm (after size exclusion-based separation), a BET surface area of >600 $m^2/g$, a pore volume fraction of ~65%, and a multimodal pore morphology composed of large (20-30 nm), surface-accessible pores interconnected by 6-12 nm pores. The liquid-vapor or liquid-liquid interfacial tensions associated with aerosol or emulsion processing (respectively) enforce a spherical shape with minimal surface roughness. Both types of particles, additionally, have fully accessible three-dimensional pore networks, as evidenced by analysis of nitrogen sorption isotherms.

The high pore volume, surface area, and accessibility of the nanoporous silica cores imparts a high cargo capacity and enables rapid loading of multiple types of therapeutic and diagnostic agents. Unimodal nanoporous cores have a high capacity for low molecular weight chemotherapeutic agents, while multimodal cores possess the large, surface-accessible pores necessary for encapsulation of siRNA, protein toxins, and other high molecular weight cargos (e.g. plasmid DNA). The rate of cargo release can be precisely controlled by the degree to which the silica core is condensed. Incorporating various amounts of AEPTMS, an amine-containing silane, into the sol used to form the nanoporous silica cores reduces the level of achievable condensation and promotes more rapid dissolution of the cores under neutral pH, high ionic strength (i.e. cytosolic) conditions. Particles that contain no AEPTMS dissolve over the course of 2 weeks in a simulated body fluid, while particles that contain 30 mol % AEPTMS dissolve within 24 hours. Protocells can, therefore, be adapted for applications requiring continuous or burst release profiles.

Incorporating AEPTMS into the precursor sol used to form nanoporous silica particles accelerates particle dissolution under cytosolic conditions and promotes more rapid release of encapsulated cargo than can be achieved via simple diffusion. AEPTMS-modified particles also have a reduced capacity for weakly basic chemotherapeutic drugs (e.g. doxorubicin), however. Therefore, in order to maximize both capacity and intracellular release, we characterized zeta potential, cargo (e.g. drug (Doxorubicin/DOX)/chemotherapy) capacity, silica dissolution rates, and cargo release rates as a function of AEPTMS concentration. As previously demonstrated, unmodified unimodal particles ($\zeta = -104.5 \pm 5.6$) have a high capacity for cargo (in the case of DOX ~1.8 mM per $10^{10}$ particles) but release only 20% of their encapsulated cargo (drug) within 24 hours (i.e. the typical doubling time of HCC). Conversely, unimodal particles modified with 30 wt % AEPTMS ($\zeta = 88.9 \pm 5.5$) release all of their encapsulated cargo (drug) within 6 hours but have a reduced drug (DOX) capacity (~0.15 mM per $10^{10}$ particles). Unimodal particles that contain 15 wt % AEPTMS ($\zeta = -21.3 \pm 5.1$) retain their high capacity for drug (DOX) (~1.1 mM per $10^{10}$ particles) and release nearly all of their encapsulated (drug) within 24 hours when exposed to a simulated body fluid; therefore these particles are selected for all experiments involving delivery of cargo. It is important to note that, while the zeta potential of unimodal silica particles increases as a function of AEPTMS concentration, the pore volume fraction of AEPTMS-modified particles (~45% for particles that contain 30 wt % AEPTMS) is not substantially different from that of unmodified particles (~50%). Therefore, we attribute the decreased cargo capacity of AEPTMS-modified unimodal particles to electrostatic repulsion rather than decreased pore volume. Multimodal particles are included as a control to demonstrate the effect of pore size on cargo capacity and the kinetics of cargo release.

General Reagents

Absolute ethanol, hydrochloric acid (37%), tetraethyl orthosilicate (TEOS, 98%), 3-aminopropyltriethoxysilane (APTES, ≥98%), 3-[2-(2-aminoethylamino)ethylamino]propyltrimethoxysilane (AEPTMS, technical grade), 2-cyanoethyl triethoxysilane (CETES, ≥97.0%), hexadecyltrimethylammonium bromide (CTAB, ≥99%), Brij®-56, sodium dodecyl sulfate (SDS, ≥98.5%), Triton® X-100, hexadecane (≥99%), doxorubicin hydrochloride (≥98%), 5-fluorouracil (≥99%), cis-diammineplatinum(II) dichloride (cisplatin, ≥99.9%), diphtheria toxin from Corynebacterium diphtheriae, cyclosporin A from Tolypocladium inflatum (CsA, ≥95%), N-Acetyl-L-cysteine (NAC, ≥99%), human epidermal growth factor, L-α-phosphatidylethanolamine, thymidine (≥99%), hypoxanthine (≥99%), bovine fibronectin, bovine collagen type I, gelatin, soybean trypsin inhibitor (≥98%), 2-mercaptoethanol (≥99.0%), DL-dithiothreitol (≥99.5%), dimethyl sulfoxide (≥99.9%), pH 5 citric acid buffer, ethylenediaminetetraacetic acid (EDTA, 99.995%), 4-(2-Hydroxyethyl)piperazine-1-ethanesulfonic acid (HEPES, ≥99.5%), ammonium phosphate dibasic (≥99.99%), and Sepharose® CL-4B were purchased from Sigma-Aldrich (St. Louis, Mo.). ABIL® EM 90 (cetyl PEG/PPG-10/1 dimethicone) was purchased from Evonik Industries (Essen, Germany). Ultra pure, EM-grade formaldehyde (16%, methanol-free) was purchased from Polysciences, Inc. (Warrington, Pa.). Hellmanex® II was purchased from Hellma (Müllheim, Germany).

Lipids 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glycero-3-Phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), and cholesterol were purchased from Avanti Polar Lipids, Inc. (Alabaster, Ala.).

Cell Lines and Growth Media

Human Hep3B (HB-8064), human hepatocytes (CRL-11233), human peripheral blood mononuclear cells (CRL-9855), human umbilical cord vein endothelial cells (CRL-2873), T lymphocytes (CRL-8293), B lymphocytes (CCL-156), Eagle's Minimum Essential Medium (EMEM), Dulbecco's Modified Eagle's Medium (DMEM), Iscove's Modified Dulbecco's Medium (IMDM), RPMI 1640 medium, fetal bovine serum (FBS), and 1× trypsin-EDTA solution (0.25% trypsin with 0.53 mM EDTA) were purchased from American Type Culture Collection (ATCC; Manassas, Va.). BEGM Bullet Kits were purchased from Lonza Group Limited (Clonetics; Walkersville, Md.). DMEM without phenol red was purchased from Sigma-Aldrich (St. Louis, Mo.).

Fluorescent Stains and Microscopy Reagents

Hoechst 33342 (350/461), 4',6-diamidino-2-phenylindole (DAPI, 356/451), Alexa Fluor® 405 carboxylic acid, succinimidyl ester (401/421), CellTracker™ Violet BMQC (415/516), CellTracker™ Green CMFDA (492/517), calcein (495/515), Alexa Fluor® 488 conjugate of annexin V (495/519), Alexa Fluor® 488 goat anti-mouse IgG (H+L) (495/519), Click-iT® AHA Alexa Fluor® 488 Protein Synthesis HCS Assay (495/519), LIVE/DEAD® Fixable Green Dead Cell Stain Kit (495/519), SYTOX® Green nucleic acid stain (504/523), MitoSOX™ Red mitochondrial superoxide indicator (510/580), Alexa Fluor® 532 carboxylic acid, succinimidyl ester (532/554), propidium iodide (535/617), pHrodo™ succinimidyl ester (558/576), CellTracker™ Red CMTPX (577/602), Texas Red® 1,2-dihexadecanoyl-sn-glycero-3-phosphoethanolamine (Texas Red® DHPE, 583/608), Alexa Fluor® 647 hydrazide (649/666), Alexa Fluor® 647 carboxylic acid, succinimidyl ester (650/668), Ulysis™ Alexa Fluor® 647 Nucleic Acid Labeling Kit (650/670), Alexa Fluor® 647 conjugate of annexin V (650/665), SlowFade® Gold antifade reagent (with and without DAPI), Image-iT® FX signal enhancer, 1× Dulbecco's phosphate-buffered saline (D-PBS), bovine albumin fraction V solution (BSA, 7.5%), and transferrin were purchased from Invitrogen Life Sciences (Carlsbad, Calif.). Red Fluorescent Protein (RFP, 557/585), CaspGLOW™ Fluorescein Active Caspase-3 Staining Kit (485/535), and CaspGLOW™ Red Active Caspase-8 Staining Kit (540/570) were purchased from BioVision, Inc. (Mountain View, Calif.). Water soluble CdSe/ZnS quantum dots, CZWD640 (640/660), were purchased from NN-Labs (Fayetteville, Ark.).

Crosslinkers

1-Ethyl-3-[3-dimethylaminopropyl]carbodiimide hydrochloride (EDC), succinimidyl 4-[N-maleimidomethyl]cyclohexane-1-carboxylate (SMCC), N-[β-Maleimidopropionic acid] hydrazide (BMPH), succinimidyl-[(N-maleimidopropionamido)-tetracosaethyleneglycol] ester (SM(PEG)$_{24}$), succinimidyl 6-[3"-(2-pyridyldithio)-propionamido]hexanoate (LC-SPDP), and the Sulfhydryl Addition Kit were purchased from Pierce Protein Research Products (Thermo Fisher Scientific LSR; Rockford, Ill.).

Other Silica Nanoparticles

Sub-5-nm silicon nanoparticles were purchased from Melorium Technologies, Inc. (Rochester, N.Y.). 10-20 nm silicon oxide nanoparticles were purchased from SkySpring Nanomaterials, Inc. (Houston, Tex.). 30-nm, 40-nm, 50-nm, 60-nm, 70-nm, 80-nm, 90-nm, 100-nm, 150-nm, 200-nm, and 10-μm silica particles were purchased from Discovery Scientific, Inc. (Vancouver, British Columbia).

Synthetic siRNA and Peptides

Silencer select siRNAs (siRNA IDs for EGFR, VEGFR-2, and PDGFR-α are s565, s7824, and s10234, respectively) were purchased from Ambion, Inc. (Austin, Tex.). The double stranded-DNA oligonucleotide (5'-AAACATGTG-GATTACCCATGTC-3') with 5' amino modifier C12 was purchased from Integrated DNA Technologies (IDT; Coralville, Iowa). 'Free' SP94 peptide (H$_2$N-SFSIILTPILPL-COOH, SEQ ID NO: 6), SP94 peptide modified with C-terminal Cys for conjugation (H$_2$N-SFSIILTPILPLGGC-COOH, SEQ ID NO: 7), and SP94 peptide used in the FIG. 2d recruitment experiments (H$_2$N-SFSIILTPILPLEEEGGC-COOH, SEQ ID NO: 8) were synthesized by New England Peptide (Gardner, Mass.). The H5WYG peptide (H$_2$N-GLF-HAIAHFIHGGWHGLIHGWYGGGC-COOH) and nuclear localization sequence (H$_2$N-NQSSNFGPMKGGNFG-GRSSGPYGGGGQYFAKPRNQGGYGGC-COOH) were synthesized by Biopeptide Co., Inc. (San Diego, Calif.). The emboldened portions of peptides are the original sequences; additional amino acid residues were added for conjugation or labeling purposes. All antibodies (CHALV-1, anti-Rab11a, anti-LAMP-1, anti-EGFR, anti-VEGFR-2, anti-PDGFR-α) were purchased from Abcam, Inc. (Cambridge, Mass.).

Cell Culture Conditions

Hep3B, hepatocytes, PBMCs, T-lymphocytes, and B-lymphocytes were obtained from ATCC and grown per manufacturer's instructions. Briefly, Hep3B was maintained in EMEM with 10% FBS. Hepatocytes were grown in flasks coated with BSA, fibronectin, and bovine collagen type I; the culture medium used was BEGM (gentamycin, amphotericin, and epinephrine were discarded from the BEGM Bullet kit) with 5 ng/mL epidermal growth factor, 70 ng/mL phosphatidylethanolamine, and 10% FBS. HUVECs were grown in DMEM with 20% FBS; gelatin-coated flasks were used to promote adhesion. PBMCs, T lymphocytes, and B lymphocytes were maintained in suspension flasks (Greiner Bio-One; Monroe, N.C.). PBMCs were grown in IMDM supplemented with 0.02 mM thymidine, 0.1 mM hypoxanthine, 0.05 mM 2-mercaptoethanol, and 10% FBS. T and B lymphocytes were grown in IMDM with 20% FBS and RPMI 1640 medium with 20% FBS, respectively. All cells were maintained at 37° C. in a humidified atmosphere (air supplemented with 5% CO$_2$). Adherent cells were passaged with 0.05% trypsin at a sub-cultivation ratio of 1:3, while non-adherent cells were seeded at a density of 2×10$^5$ cells/mL and maintained at 1-5×10$^6$ cells/mL.

Synthesis and Characterization of Nanoporous Silica Particles

Synthesis of Unimodal Silica Nanoparticles

The aerosol-assisted evaporation-induced self-assembly method employed to prepare nanoporous silica particles with unimodal porosity has been described by Lu, et al.[2]. Briefly, a homogenous sol containing a silica precursor (TEOS), a structure-directing surfactant (CTAB, initially at a concentration much less than the critical micelle concentration, or CMC), and HCl dissolved in a solution of water and ethanol was aerosolized using a modified commercial atomizer (Model 9302A; TSI, Inc.; St Paul, Minn.). Nitrogen was used as the carrier gas, and all heating zones were maintained at 400° C. to evaporate the solvent and increase the effective surfactant concentration. Pressure drop at the pinhole was 20 psi. Particles were collected on a Durapore membrane filter (Millipore; Billerica, Mass.) maintained at 80° C. A typical reaction mixture contained 55.9 mL of deionized H$_2$O, 43 mL of 200-proof ethanol, 1.10 mL of 1.0 N HCl, 4.0 g of CTAB, and 10.32 g of TEOS. To prepare nanoporous silica particles that dissolve more rapidly under intracellular (neutral pH, relatively high salt concentrations) conditions, various amounts of TEOS and AEPTMS, an amine-containing silane, were incorporated into the precursor sol, and the pH of the system was adjusted to 2.0 using concentrated HCl. For example, to prepare particles with 15 wt % AEPTMS, 9.36 g of TEOS and 1.33 g of AEPTMS were used.

Synthesis of Multimodal Silica Nanoparticles

The emulsion processing used to synthesize nanoporous silica particles with multimodal porosity has been described by Carroll, et al.[1]. Briefly, 1.82 g of CTAB (soluble in the aqueous phase) was added to 20 g of deionized water, stirred at 40° C. until dissolved, and allowed to cool to 25° C. 0.57 g of 1.0 N HCl, 5.2 g of TEOS, and 0.22 g of NaCl were added to the CTAB solution, and the resulting sol was stirred for 1 hour. An oil phase composed of hexadecane with 3 wt % Abil EM 90 (a non-ionic emulsifier soluble in the oil phase) was prepared. The precursor sol was combined with the oil phase (1:3 volumetric ratio of sol:oil) in a 1000-mL round-bottom flask, stirred vigorously for 2 minutes to promote formation of a water-in-oil emulsion, affixed to a rotary evaporator (R-205; Buchi Laboratory Equipment; Switzerland), and placed in an 80° C. water bath for 30 minutes. The mixture was then boiled under a reduced pressure of 120 mbar (35 rpm for 3 hours) to remove the solvent. Particles were the centrifuged (Model Centra MP4R; International Equipment Company; Chattanooga, Tenn.) at 3000 rpm for 20 minutes, and the supernatant was decanted. Finally, the particles were calcined at 500° C. for 5 hours to remove surfactants and other excess organic matter. As described by Carroll, et al., solvent extraction enriches the aqueous phase in CTAB (>CMC), and the resulting micelles template 6-12 nm pores upon condensation of silica particles (in the aqueous phase). Additionally, adsorption of two surfactants (CTAB and Abil EM 90) at the water-oil interface synergistically decreases the interfacial tension, which results in the spontaneous formation of 20-30 nm microemulsion droplets that template large, surface-accessible pores.

Characterization of Silica Nanoparticles

Dynamic light scattering of nanoporous silica particles was performed using a Zetasizer Nano (Malvern; Worcestershire, United Kingdom). Samples were prepared by diluting 48 μL of silica particles (25 mg/mL) in 2.4 ml of 1×D-PBS. Solutions were transferred to 1 mL polystyrene cuvettes (Sarstedt; Nümbrecht, Germany) for analysis. Nitrogen sorption was performed using an ASAP 2020 Surface Area and Porosity Analyzer (Micromeritics Instrument Corporation; Norcross, Ga.). Zeta potential measurements were made using a Zetasizer Nano (Malvern; Worcestershire, United Kingdom). In a typical experiment, silica particles, liposomes, or protocells were diluted 1:50 in a simulated body fluid (pH 7.4) or citric acid buffer (pH 5.0), both of which were adjusted to contain 150 mM NaCl, and transferred to 1-mL folded capillary cells (Malvern; Worcestershire, United Kingdom) for analysis. See Supplementary FIG. 1 for DLS and nitrogen sorption data and Supplementary FIG. 12 for zeta potential values of silica nanoparticles, liposomes, and protocells.

Synthesis, Loading, and Surface Functionalization of Protocells

Liposome Fusion to Nanoporous Silica Particles

The procedure used to synthesize protocells has been described by Liu, et al.[25-27] and will be mentioned only briefly. Lipids were ordered from Avanti Polar Lipids pre-dissolved in chloroform and stored at 20° C. Immediately prior to protocell synthesis, 2.5 mg of lipid was dried under a stream of nitrogen and placed in a vacuum oven (Model 1450M, VWR International, West Chester, Pa.) overnight to remove residual solvent. Lipids were re-hydrated in 0.5×D-PBS at a concentration of 2.5 mg/mL and were passed through a 100-nm filter at least 10 times using a Mini-Extruder set (Avanti Polar Lipids, Inc.; Alabaster, Ala.). DPPC and DSPC were dissolved in 0.5×D-PBS pre-warmed to their respective transition temperatures (41° C. and 55° C.) and maintained at 60° C. during the extrusion process. Resulting liposomes (~120-nm in diameter) were stored at 4° C. for no more than one week. Nanoporous silica cores were dissolved in 0.5×D-PBS (25 mg/mL) and exposed to an excess of liposomes (1:2-1:4 volumetric ratio of lipid:silica) for 30-90 minutes at room temperature. Protocells were stored in the presence of excess lipid for up to 3 months at 4° C. To remove excess lipid, protocells were centrifuged at 10,000 rpm for 5 minutes, washed twice, and re-suspended in 0.5×D-PBS.

Optimization of the Supported Lipid Bilayer Composition

The composition of the SLB was optimized to minimize non-specific binding and toxicity to control cells; see Supplementary FIG. 4 for structures of the various lipids that were used. The protocells used in all surface binding, internalization, and delivery experiments had SLBs composed of DOPC (or DPPC) with 5 wt % DOPE (or DPPE), 30 wt % cholesterol, and 5 wt % 18:1 (or 16:0) PEG-2000 PE. If necessary, fluorescent lipids (18:1-12:0 NBD-PC, 16:0-12:0 NBD-PC, or Texas Red® DHPE) were incorporated into the SLB at 1-5 wt %. Lipids were lyophilized together prior to rehydration and extrusion; for example 75 of DOPC (25 mg/mL), 5 μL of DOPE (25 mg/mL), 10 μL of cholesterol (75 mg/mL), 5 μL of 18:1 PEG-2000 PE (25 mg/mL), and 5 μL of 18:1-12:0 NBD-PC (5 mg/mL) were combined and dried to form liposomes composed of DOPC with 5 wt % DOPE, 30 wt % cholesterol, 5 wt % PEG-2000, and 1 wt % NBD-PC.

Modification of the Supported Lipid Bilayer with Various Types of Targeting Ligands The specific affinity of protocells for HCC was optimized by conjugating various types of targeting ligands in various densities to the SLB. The SP94 and H5WYG peptides (synthesized with C-terminal cysteine residues) were conjugated to primary amines present in the head groups of PE via the heterobifunctional crosslinker, NHS-(PEG)$_n$-maleimide, which is reactive toward sulfhydryl and amine moieties and possesses a PEG spacer arm, the length of which can be altered to optimize specific affinity. SM(PEG)$_{24}$ was used in most studies (spacer arm=9.52 nm). Amine moieties present in transferrin, anti-EGFR, and CHALV-1 were converted to free sulfhydryls using the Sulfhydryl Addition Kit (per manufacturer's instructions). Functionalized transferrin and antibodies were conjugated to PE in the SLB using SM(PEG)$_{24}$. Ligand density was controlled by both reaction stoichiometry and incubation time. For example, protocells were incubated with a 10-fold molar excess of SP94 for 2 hours at room temperature to attain a peptide density of 0.015 wt % (~6 peptides/protocell), whereas protocells were incubated with a 5000-fold molar excess of SP94 overnight at 4° C. to attain a peptide density of 5.00 wt % (~2048 peptides/protocell). Average ligand density was determined by Tricine-SDS-PAGE (SP94 and H5WYG peptides) or Laemmli-SDS-PAGE (transferrin, anti-EGFR, and CHALV-1)[28]. Briefly, protocells were modified with various ligand densities using LC-SPDP (spacer arm=1.57 nm), a heterobifunctional crosslinker that reacts with primary amine and sulfhydryl moieties and is cleavable via reduction. Protocells were exposed to 10 mM dithiothreitol (DTT) for 30 minutes and centrifuged at 10,000 rpm for 5 minutes; the resulting supernatant contained free ligands, the concentration of which was determined via SDS-PAGE by comparing the band intensity of each sample to a standard curve using Image J Image Processing and Analysis software (National Institutes of Health; Bethesda, Md.). 20% gels (with 6% bis-acrylamide and 6 M urea) were used to analyze the SP94 and H5WYG peptide densities. 10% gels were employed to analyze antibody (anti-EGFR and CHALV-1) densities, while 15% gels were used to analyze the density of transferrin.

Preparation of Fluorescently-Labeled Nanoporous Cores

Nanoporous cores were fluorescently-labeled by adding 100 μL of particles (25 mg/mL) to 900 μL of 20% APTES in 0.5×D-PBS; the particles were incubated in APTES overnight at room temperature, centrifuged (10,000 rpm, 5 minutes) to remove unreacted APTES, and re-suspended in 1 mL of 0.5×D-PBS. An amine-reactive fluorophore (e.g. Alexa Fluor® 647 carboxylic acid, succinimidyl ester; 1 mg/mL in DMSO) was added (5 μL of dye per mL of particles), and the particles were kept at room temperature for 2 hours prior to being centrifuged to remove unreacted dye. Fluorescently-labeled particles were stored in 0.5×D-PBS at 4° C.

Loading of Unimodal Cores and Liposomes with Chemotherapeutic Drugs

Prior to liposome fusion, unimodal nanoporous cores modified to contain 15 wt % AEPTMS (25 mg/mL) were soaked in doxorubicin (5 mM) or a mixture of doxorubicin, cisplatin, and 5-fluorouracil (5 mM of each drug) for 1 hour at room temperature. Excess drug was removed via centrifugation of the particles at 10,000 rpm for 5 minutes. 120-nm liposomes were loaded with DOX using an ammonium phosphate gradient-based method that has been described previously[29]. Briefly, lipid films were re-hydrated with 300 mM (NH$_4$)$_2$HPO$_4$, and the liposome solution was extruded through a 100-nm membrane at least 10 times. Liposomes were equilibrated with an isotonic buffer solution (140 mM NaCl, 10 mM HEPES, pH 7.4) via dialysis (Float-A-Lyzer G2 dialysis units, 3.5-5 kDa MWCO; Spectrum Laboratories, Inc.; Rancho Dominguez, Calif.) and incubated with doxorubicin HCl (1:3 drug:lipid molar ratio) overnight at 4° C. Excess DOX was removed via size-exclusion chromatography on a 0.7 cm×10 cm Sepharose® CL-4B column. Liposomes were loaded with 5-FU or cisplatin as described previously[30,31].

Loading of Multimodal Cores with the Multicomponent Mixture, siRNA, and Diphtheria Toxin A-Chain Multimodal nanoporous cores modified to contain 20 wt % AEPTMS (25 mg/mL) were soaked in a solution of calcein (5 mM), Alexa Fluor® 647-labeled dsDNA oligonucleotides (100 μM), RFP (100 μM), and CdSe/ZnS quantum dots (10 μM) for 4 hours; the concentration of each cargo was varied in order to attain the optimal fluorescence intensity for hyperspectral imaging. Calcein was modified with the NLS (synthesized with a C-terminal cysteine residue) by dissolving 1 mg each of calcein and the NLS in 850 μL of 1×D-PBS; 100 μL of EDC (10 mg/mL in deionized water) and 50 μL of BMPH (10 mg/mL in DMSO) were added, and the mixture was incubated for 2 hours at room temperature. Excess calcein was removed via dialysis (Slide-A-Lyzer mini dialysis units, 2 kDa MWCO; Thermo Fisher Scientific LSR; Rockford, Ill.). The dsDNA oligonucleotide was labeled using the Ulysis™ Alexa Fluor® 647 Nucleic Acid Labeling Kit (per manufacturer's instructions) and modified with the NLS by combining 50 μL of dsDNA (2 mM in deionized water) with 50 μL of the NLS (1 mM in DMSO) and 10 μL of SMCC (10 mg/mL in DMSO); the mixture was incubated at room temperature for 2 hours, and excess NLS was removed via dialysis (Slide-A-Lyzer mini dialysis units, 7 kDa MWCO; Thermo Fisher Scientific LSR; Rockford, Ill.). For the delivery experiments described in Supplementary FIGS. 13-16, multimodal nanoporous cores modified with 20 wt % AEPTMS (25 mg/mL) were soaked in siRNA (100 μM) or diphtheria toxin A-chain (100 μM) for 2 hours at 4° C. Unencapsulated cargo was removed via centrifugation at 10,000 rpm for 5 minutes, and liposomes were immediately fused to cargo-loaded cores.

Packaging of the CB1 Plasmid with Histone Proteins.

The process used to supercoil the CB1 plasmid (pCB1) is depicted in FIG. 4. The schematic depicts the process used to supercoil the CB1 plasmid (pCB1) (the CB1 plasmid vector is presented below and in attached FIG. 12) using a highly saturated salt solution, package supercoiled pCB1 with histones H1, H2A, H2B, H3, and H4, and modifying the resulting pCB1-histone complex with a nuclear localization sequence(NLS) that promotes translocation through nuclear pores by conjugation to histone protein. FIGS. 4 (B) and (D) show atomic force microscopy (AFM) images of the CB1 plasmid (B) and histone-packaged pCB1 (D). Scale bars=100 nm. (C) and (E) Height profiles that correspond to the red lines in (B) and (D), respectively.

Synthesis of MC40-Targeted Mesoporous Silica Nanoparticle-Supported Lipid Bilayers (Protocells) Loaded with Histone-Packaged pCB1.

Figure 5A:
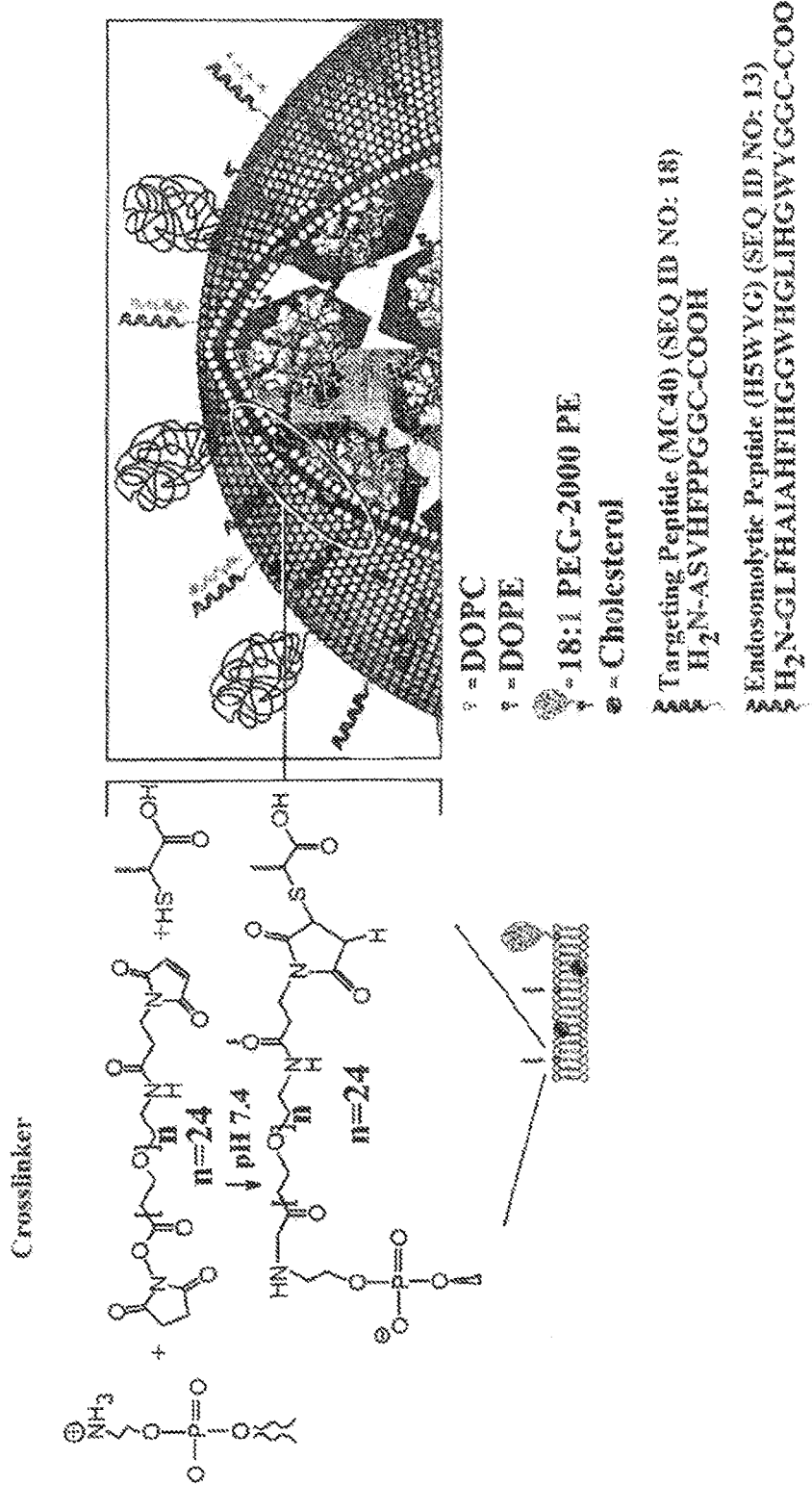
FIG. 5 depicts the synthesis of MC40-targeted mesoporous silica nanoparticle-supported lipid bilayers (protocells) loaded with histone-packaged pCB1. (A) Schematic depicting the process used to generate DNA-loaded, peptide-targeted protocells. Histone-packaged pCB1 is loaded into the mesoporous silica nanoparticles that form the core of the protocell by simply soaking the particles in a solution of the pCB1-histone complex. PEGylated liposomes are then fused to DNA-loaded cores to form a supported lipid bilayer (SLB) that is further modified with a targeting peptide (MC40) that binds to HCC and a endosomolytic peptide (H5WYG) that promotes endosomal escape of internalized protocells. A sulfhydryl-to-amine crosslinker (spacer arm=9.5 nm) was used to conjugate peptides, modified with a C-terminal cysteine residue, to DOPE moieties in the SLB. (B) Transmission electron microscopy (TEM) image of the mesoporous silica nanoparticles that are used as the core of the protocell. Scale bar=200 nm. Inset=scanning electron microscopy (SEM) image, which demonstrates that the 15-25 nm pores are surface-accessible. Inset scale bar=50 nm. (C) Size distribution for the mesoporous silica nanoparticles, as determined by dynamic light scattering (DLS). (D, left axis) Cumulative pore volume plot for the mesoporous silica nanoparticles, calculated from the adsorption branch of the nitrogen sorption isotherm shown in Figure S-4A using the Barrett-Joyner-Halenda (BJH) model. (D, right axis) Size distribution for the pCB1-histone complex, as determined by DLS.
Figure 5A:
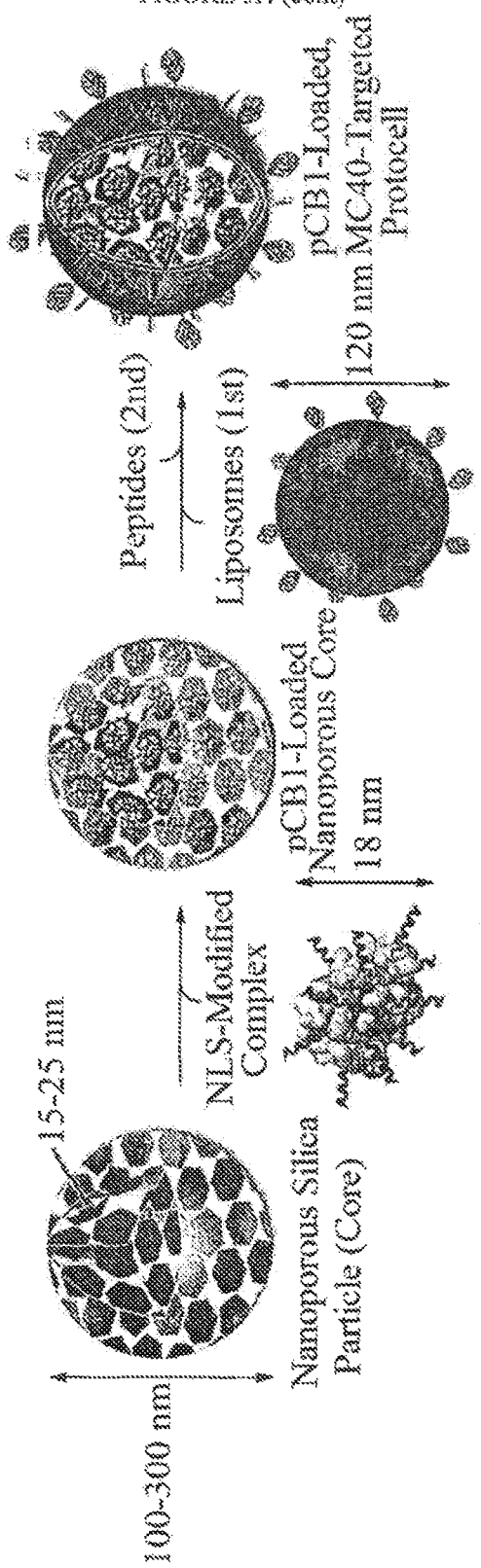
Figure 5C:
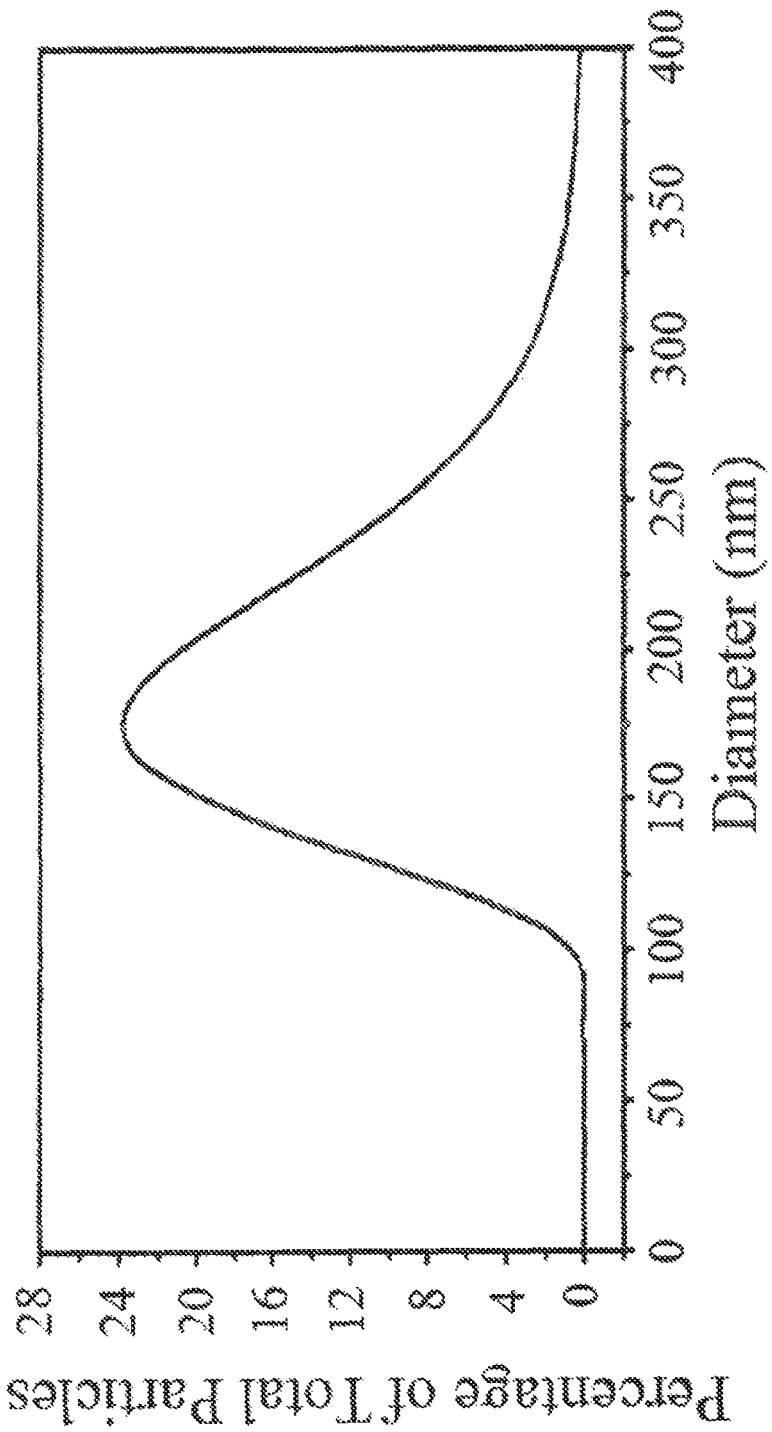

As depicted in FIG. 5, 5(A) provides a schematic depicting the process used to generate DNA-loaded, peptide-targeted protocells. Pursuant to this method Histone-packaged pCB1 is loaded into the mesoporous silica nanoparticles that form the core of the protocell by simply soaking the particles in a solution of the pCB1-histone complex. PEGylated liposomes are then fused to DNA-loaded cores to form a supported lipid bilayer (SLB) that is further modified with a targeting peptide (MC40) that binds to HCC and a endosomolytic peptide (H5WYG) that promotes endosomal escape of internalized protocells. A sulfhydryl-to-amine crosslinker (spacer arm=9.5 nm) was used to conjugate peptides, modified with a C-terminal cysteine residue, to DOPE moieties in the SLB. FIG. 5(B) shows the transmission electron microscopy (TEM) image of the mesoporous silica nanoparticles that are used as the core of the protocell. Scale bar=200 nm. Inset=scanning electron microscopy (SEM) image, which demonstrates that the 15-25 nm pores are surface-accessible. Inset scale bar=50 nm. 5(C) shows the size distribution for the mesoporous silica nanoparticles, as determined by dynamic light scattering (DLS). (5D, left axis) Cumulative pore volume plot for the mesoporous silica nanoparticles, calculated from the adsorption branch of the nitrogen sorption isotherm shown in Figure S-4A using the Barrett-Joyner-Halenda (BJH) model. (5D, right axis) Size distribution for the pCB1-histone complex, as determined by DLS.

Mesoporous Silica Nanoparticles have a High Capacity for Histone-Packaged pCB1, and the Resulting Protocells Release Encapsulated DNA Only Under Conditions that Mimic the Endosomal Environment.

Figure 6C:
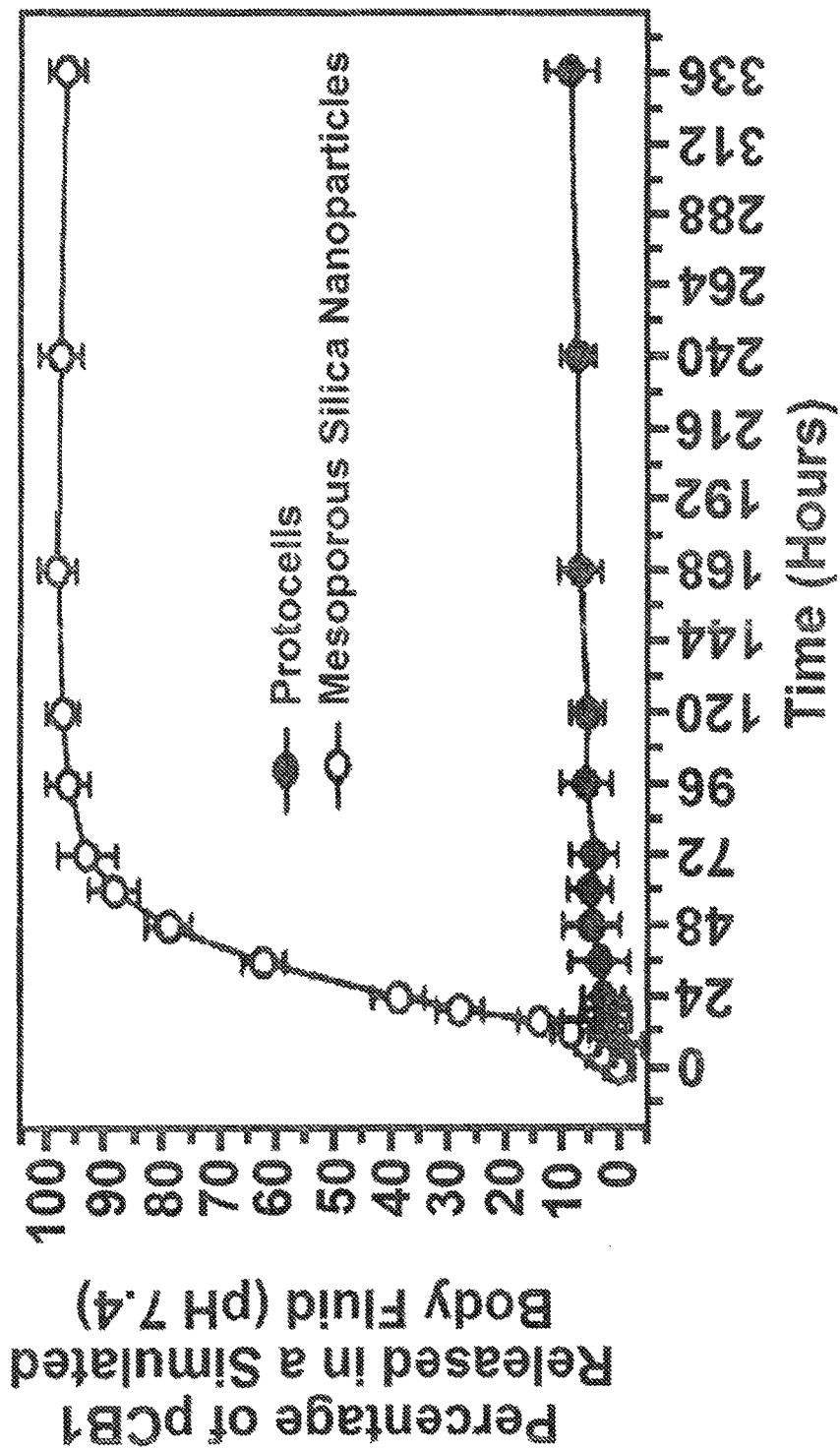
FIG. 6 shows that mesoporous silica nanoparticles have a high capacity for histone-packaged pCB1, and the resulting protocells release encapsulated DNA only under conditions that mimic the endosomal environment according to one embodiment. (A) The concentration of pCB1 or histone-packed pCB1 ('complex') that can be encapsulated within unmodified mesoporous silica nanoparticles ($\zeta$=−38.5 mV) or mesoporous silica nanoparticles modified with APTES, an amine-containing silane ($\zeta$=+11.5 mV). (B) The percentage of Hep3B that become positive for ZsGreen, a green fluorescent protein encoded by pCB1, when $1\times10^6$ cells/mL are incubated with $1\times10^9$ MC40-targeted, pCB1-loaded protocells for 24 hours at 37° C. The x-axis specifies whether the protocell core was modified with APTES and whether pCB1 was pre-packaged with histones. pCB1 packaged with a mixture of DOTAP and DOPE (1:1 w/w) was included as a control in (A) and (B). (C) and (D) The time-dependent release of histone-packaged pCB1 from unmodified mesoporous silica nanoparticles and corresponding protocells upon exposure to a simulated body fluid (C) or a pH 5 buffer (D). The protocell SLB was composed of DOPC with 5 wt % DOPE, 30 wt % cholesterol, and 10 wt % PEG-2000 and, for (B), was modified with 0.015 wt % MC40 and 0.500 wt % H5WYG. All error bars represent 95% confidence intervals (1.96σ) for n=3.

As depicted in FIG. 6(A), the concentration of pCB1 or histone-packed pCB1 ('complex') that can be encapsulated within unmodified mesoporous silica nanoparticles ($\zeta$=−38.5 mV) or mesoporous silica nanoparticles modified with APTES, an amine-containing silane ($\zeta$=+11.5 mV). FIG. 6(B) shows the percentage of Hep3B that become positive for ZsGreen, a green fluorescent protein encoded by pCB1, when $1\times10^6$ cells/mL are incubated with $1\times10^9$ MC40-targeted, pCB1-loaded protocells for 24 hours at 37° C. The x-axis specifies whether the protocell core was modified with APTES and whether pCB1 was pre-packaged with histones. pCB1 packaged with a mixture of DOTAP and DOPE (1:1 w/w) was included as a control in (A) and (B). FIGS. 6(C) and (D) show the time-dependent release of histone-packaged pCB1 from unmodified mesoporous silica nanoparticles and corresponding protocells upon exposure to a simulated body fluid (C) or a pH 5 buffer (D). The protocell SLB was composed of DOPC with 5 wt % DOPE, 30 wt % cholesterol, and 10 wt % PEG-2000 and, for (B), was modified with 0.015 wt % MC40 and 0.500 wt % H5WYG. All error bars represent 95% confidence intervals (1.96σ) for n=3.

The Process by which MC40-Targeted Protocells Deliver Histone-Packaged pCB1 to HCC.

As depicted in the schematic presented in attached FIG. 7 MC40-targeted protocells bind to Hep3B cells with high affinity due to the recruitment of targeting peptides to Met, which is over-expressed by a variety of HCC lines. The fluid DOPC SLB promotes peptide mobility and, therefore, enables protocells modified with a low MC40 density to retain a high specific affinity for Hep3B (see FIG. 8A). [2] MC40-targeted protocells become internalized by Hep3B via receptor-mediated endocytosis (see FIG. 8B and FIG. 15A). [3] Endosomal conditions destabilize the SLB [insert Nature Materials ref] and cause protonation of the H5WYG endosomolytic peptide, both of which enable histone-packaged pCB1 to become dispersed in the cytosol of Hep3B cells (see FIG. 15B). [4] pCB1-histone complexes, when modified with a nuclear localization sequence (NLS), become concentrated in the nuclei of Hep3B cells within ~24 hours (see FIG. 16C), which enables efficient transfection of both dividing and non-dividing cancer cells (see FIG. 17).

MC40-Targeted Protocells Bind to HCC with High Affinity and are Internalized by Hep3B but not by Normal Hepatocytes.

Figure 8B:
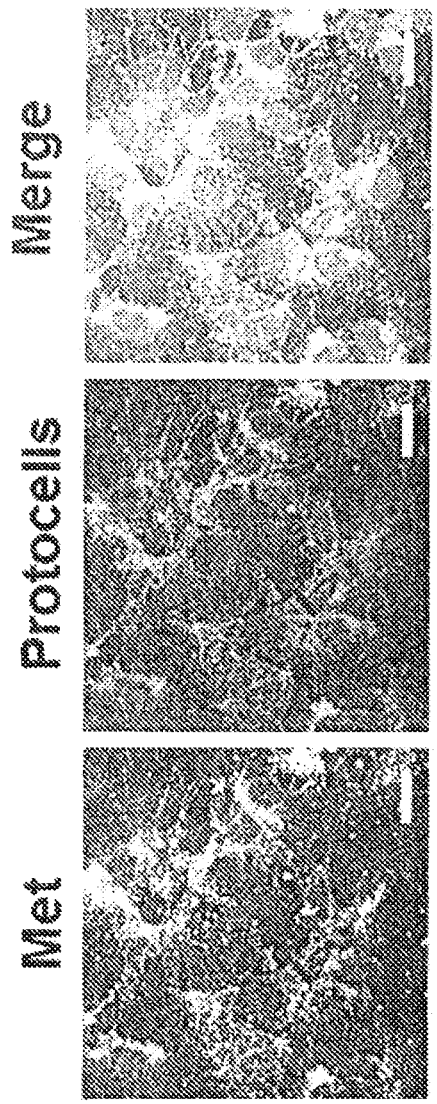
FIG. 8 shows that MC40-targeted protocells bind to HCC with high affinity and are internalized by Hep3B but not by normal hepatocytes. (A) Apparent dissociation constants ($K_d$) for MC40-targeted protocells when exposed to Hep3B or hepatocytes; $K_d$ values are inversely related to specific affinity and were determined from saturation binding curves (see Figure S-11). Error bars represent 95% confidence intervals (1.96σ) for n=5. (B) and (C) Confocal fluorescence microscopy images of Hep3B (B) and hepatocytes (C) that were exposed to a 1000-fold excess MC40-targeted protocells for 1 hour at 37° C. Met was stained with an Alexa Fluor® 488-labeled monoclonal antibody (green), the protocell core was labeled with Alexa Fluor® 594 (red), and cell nuclei were stained with Hoechst 33342 (blue). Scale bars=20 µm. Protocell SLBs were composed of DOPC with 5 wt % DOPE, 30 wt % cholesterol, and 10 wt % PEG-2000 (18:1) and were modified with either 0.015 wt % (A-C) or 0.500 wt % (A) of the MC40 targeting peptide.

FIG. 8(A) shows the apparent dissociation constants ($K_d$) for MC40-targeted protocells when exposed to Hep3B or hepatocytes; $K_d$ values are inversely related to specific affinity and were determined from saturation binding curves (see Figure S-11). Error bars represent 95% confidence intervals (1.96σ) for n=5. FIGS. 8(B) and (C) show the confocal fluorescence microscopy images of Hep3B (B) and hepatocytes (C) that were exposed to a 1000-fold excess MC40-targeted protocells for 1 hour at 37° C. Met was stained with an Alexa Fluor® 488-labeled monoclonal antibody (green), the protocell core was labeled with Alexa Fluor® 594 (red), and cell nuclei were stained with Hoechst 33342 (blue). Scale bars=20 µm. Protocell SLBs were composed of DOPC with 5 wt % DOPE, 30 wt % cholesterol, and 10 wt % PEG-2000 (18:1) and were modified with either 0.015 wt % (A-C) or 0.500 wt % (A) of the MC40 targeting peptide.

MC40-targeted, pCB1-loaded protocells induce apoptosis of HCC at picomolar concentrations but have a minimal impact on the viability of normal hepatocytes.

Figure 9B:
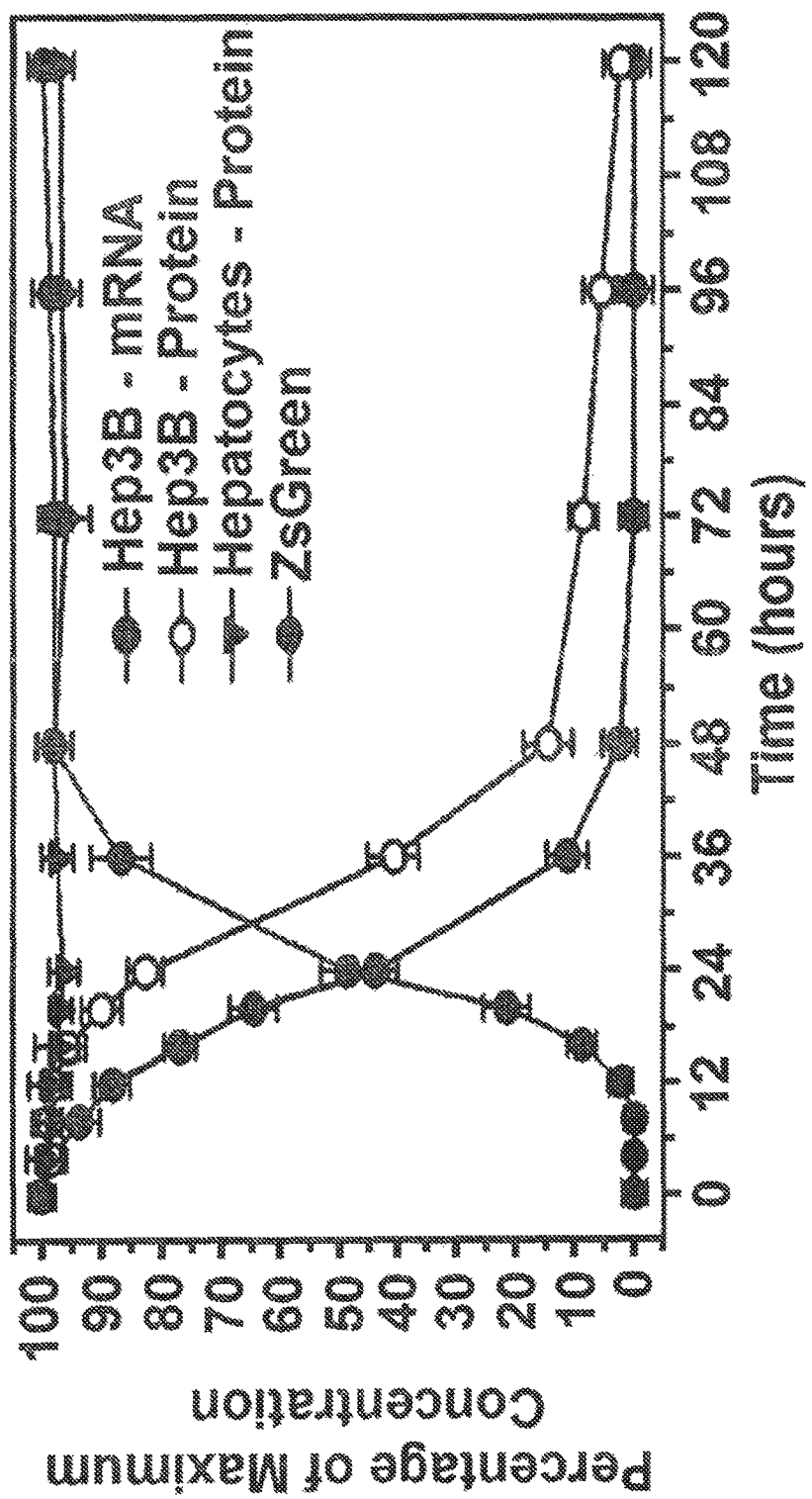
FIG. 9 shows MC40-targeted, pCB1-loaded protocells induce apoptosis of HCC at picomolar concentrations but have a minimal impact on the viability of normal hepatocytes. Dose (A) and time (B) dependent decreases in expression of cyclin B1 mRNA and cyclin B1 protein upon continual exposure of Hep3B to MC40-targeted, pCB1-loaded protocells at 37° C. Cells were exposed to various pCB1 concentrations for 48 hours in (A) and to 5 pM of pCB1 for various periods of time in (13). Expression of cyclin B1 protein in hepatocytes and ZsGreen in Hep3B are included as controls. Real-time PCR and immunofluorescence were employed to determine cyclin B1 mRNA and protein concentrations, respectively. (C) The percentage of Hep3B that become arrested in $G_2$/M phase after continual exposure to MC40-targeted, pCB1-loaded protocells ([pCB1]=5 pM) for various periods of time at 37° C. The percentage of hepatocytes in $G_2$/M phase and Hep3B in S phase are included for comparison. Cells were stained with Hoechst 33342 prior to cell cycle analysis. (D) The percentage of Hep3B that become apoptotic upon continual exposure to MC40-targeted, pCB1-loaded protocells ([pCB1]=5 pM) for various periods of time at 37° C. The percentage of hepatocytes positive for markers of apoptosis was included as a control. Cells positive for Alexa Fluor® 647-labeled annexin V were considered to be in the early stages of apoptosis, while cells positive for both annexin V and propidium iodide were considered to be in the late stages of apoptosis. The total number of apoptotic cells was determined by adding the numbers of single-and double-positive cells. In all experiments, protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. All error bars represent 95% confidence intervals (1.96σ) for n=3.
Figure 9C:
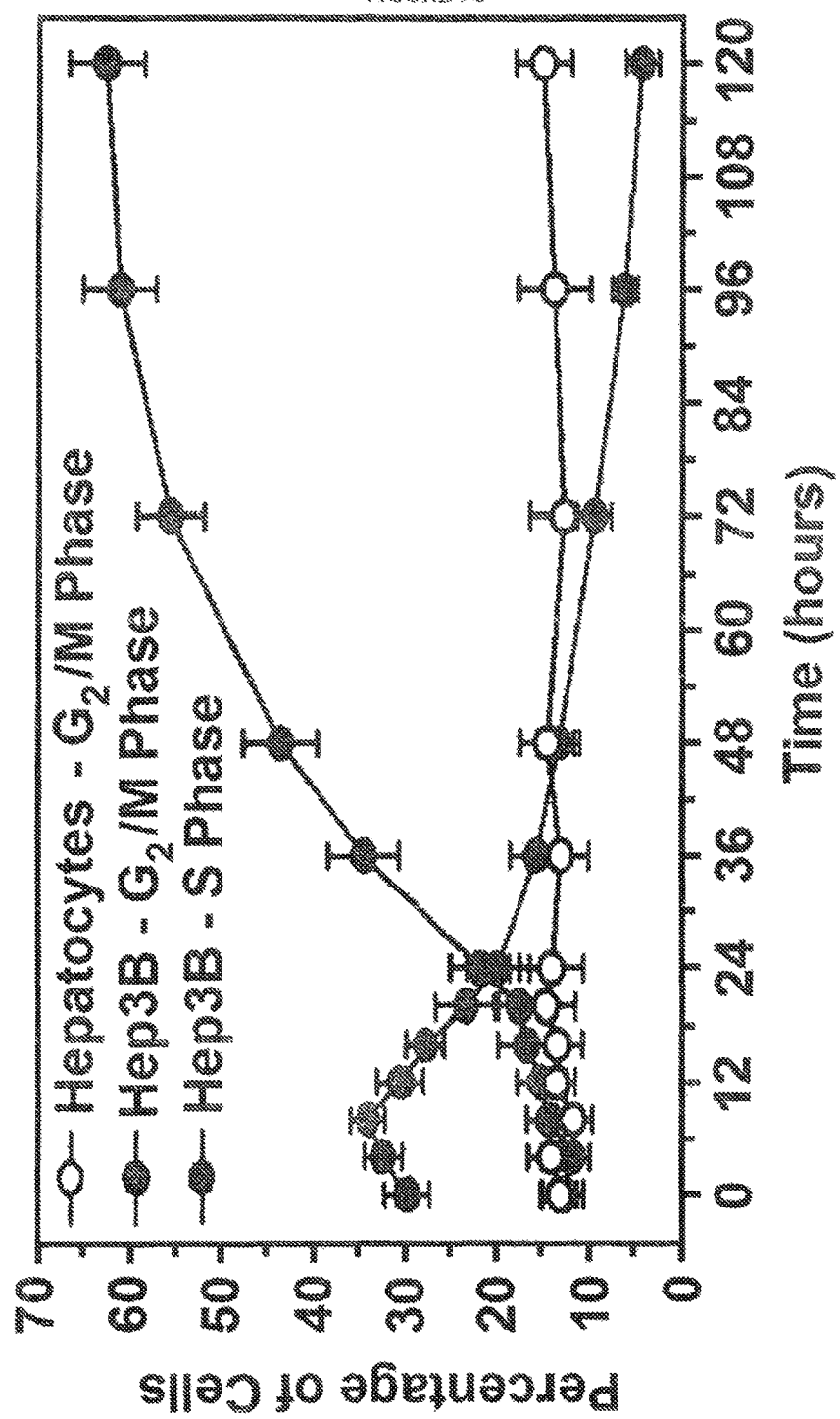
Figure 9D:
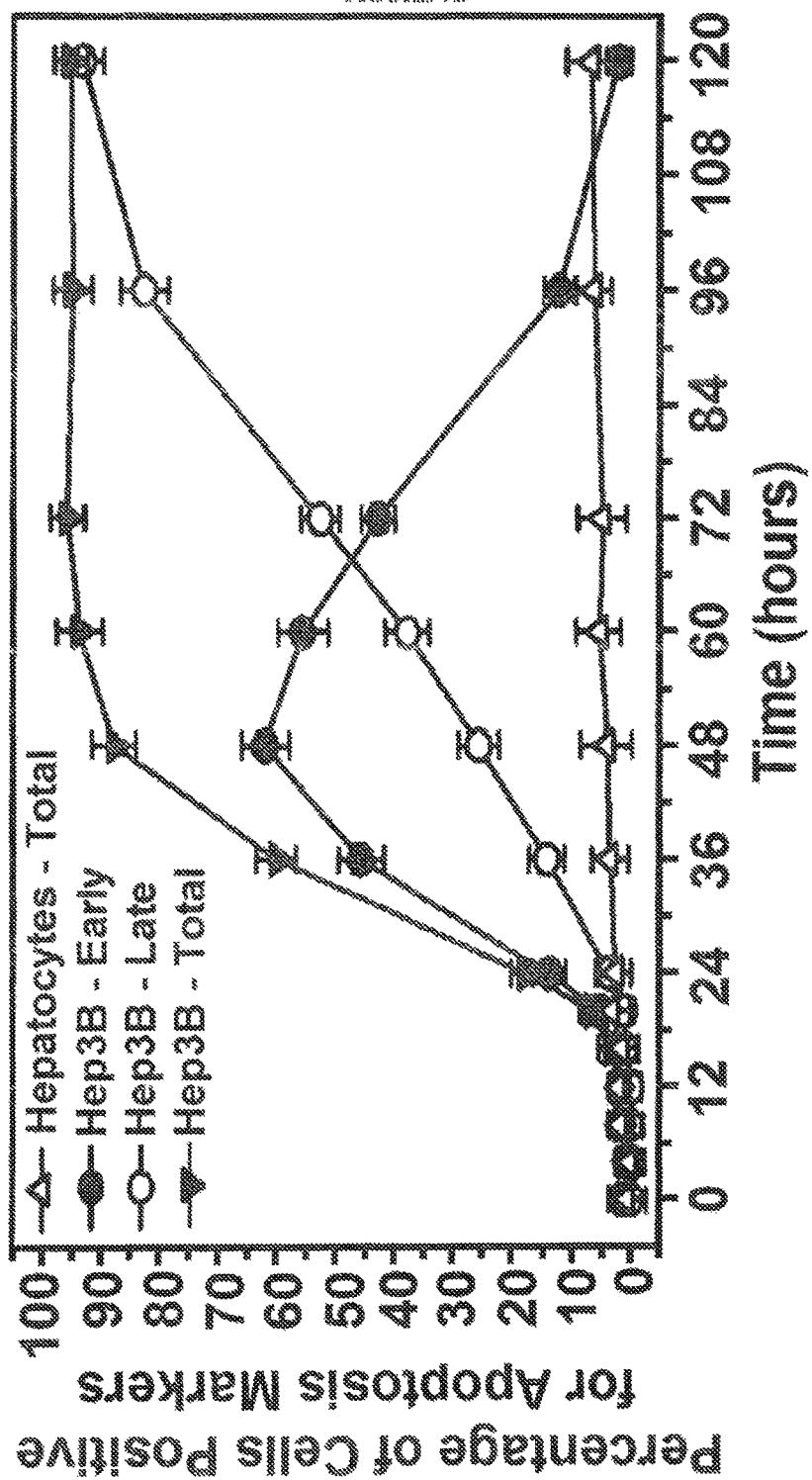

FIGS. 9(A) and (B) shows the dose (A) and time (B) dependent decreases in expression of cyclin B1 mRNA and cyclin B1 protein upon continual exposure of Hep3B to MC40-targeted, pCB1-loaded protocells at 37° C. Cells were exposed to various pCB1 concentrations for 48 hours in (A) and to 5 pM of pCB1 for various periods of time in (B). Expression of cyclin B1 protein in hepatocytes and ZsGreen in Hep3B are included as controls. Real-time PCR and immunofluorescence were employed to determine cyclin B1 mRNA and protein concentrations, respectively. FIG. 9(C) shows the percentage of Hep3B that become arrested in $G_2$/M phase after continual exposure to MC40-targeted, pCB1-loaded protocells ([pCB1]=5 pM) for various periods of time at 37° C. The percentage of hepatocytes in $G_2$/M phase and Hep3B in S phase are included for comparison. Cells were stained with Hoechst 33342 prior to cell cycle analysis. FIG. 9(D) shows the percentage of Hep3B that become apoptotic upon continual exposure to MC40-targeted, pCB1-loaded protocells ([pCB1]=5 pM) for various periods of time at 37° C. The percentage of hepatocytes positive for markers of apoptosis was included as a control. Cells positive for Alexa Fluor® 647-labeled annexin V were considered to be in the early stages of apoptosis, while cells positive for both annexin V and propidium iodide were considered to be in the late stages of apoptosis. The total number of apoptotic cells was determined by adding the numbers of single-and double-positive cells. In all experiments, protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. All error bars represent 95% confidence intervals (1.96σ) for n=3.

MC40-Targeted, pCB1-Loaded Protocells Induce Selective Apoptosis of HCC 2500-Fold more Effectively than Corresponding Lipoplexes.

FIG. 10(A) shows the zeta potential values for DOPC protocells, DOPC protocells modified with 10 wt % PEG-2000 (18:1), lipoplexes composed of pCB1 and a mixture of DOTAP and DOPE (1:1 w/w), and DOTAP/DOPE lipoplexes modified with 10 wt % PEG-2000. All zeta potential measurements were conducted in 0.5×PBS (pH 7.4). FIG. 10(B, left axis) shows the percentage of Hep3B and hepatocytes that become apoptotic upon continual exposure to 5 pM of pCB1, delivered via MC40-targeted protocells or lipoplexes, for 48 hours at 37° C. FIG. 10(B, right axis) shows the number of MC40-targeted, pCB1-loaded protocells or lipoplexes necessary to induce apoptosis in 90% of $1\times10^6$ Hep3B cells within 48 hours at 37° C. For (B), cells were stained with Alexa Fluor® 647-labeled annexin V and propidium iodide; single-and double-positive cells were considered to be apoptotic. Protocell SLBs were composed of DOPC with 5 wt % DOPE, 30 wt % cholesterol, and 10 wt % PEG-2000 (when indicated) and were modified with 0.015 wt % MC40 and 0.500 wt % H5WYG. DOTAP/DOPE lipoplexes were modified with 10 wt % PEG-2000 (when indicated), 0.015 wt % MC40, and 0.500 wt % H5WYG. pCB1 was modified with the NLS in all experiments. All error bars represent 95% confidence intervals (1.96σ) for n=3.

MC40-Targeted Protocells selectively Deliver High Concentrations of Taxol, Bcl-2-Specific siRNA, and pCB1 to HCC without Affecting the Viability of Hepatocytes.

Figure 11A:
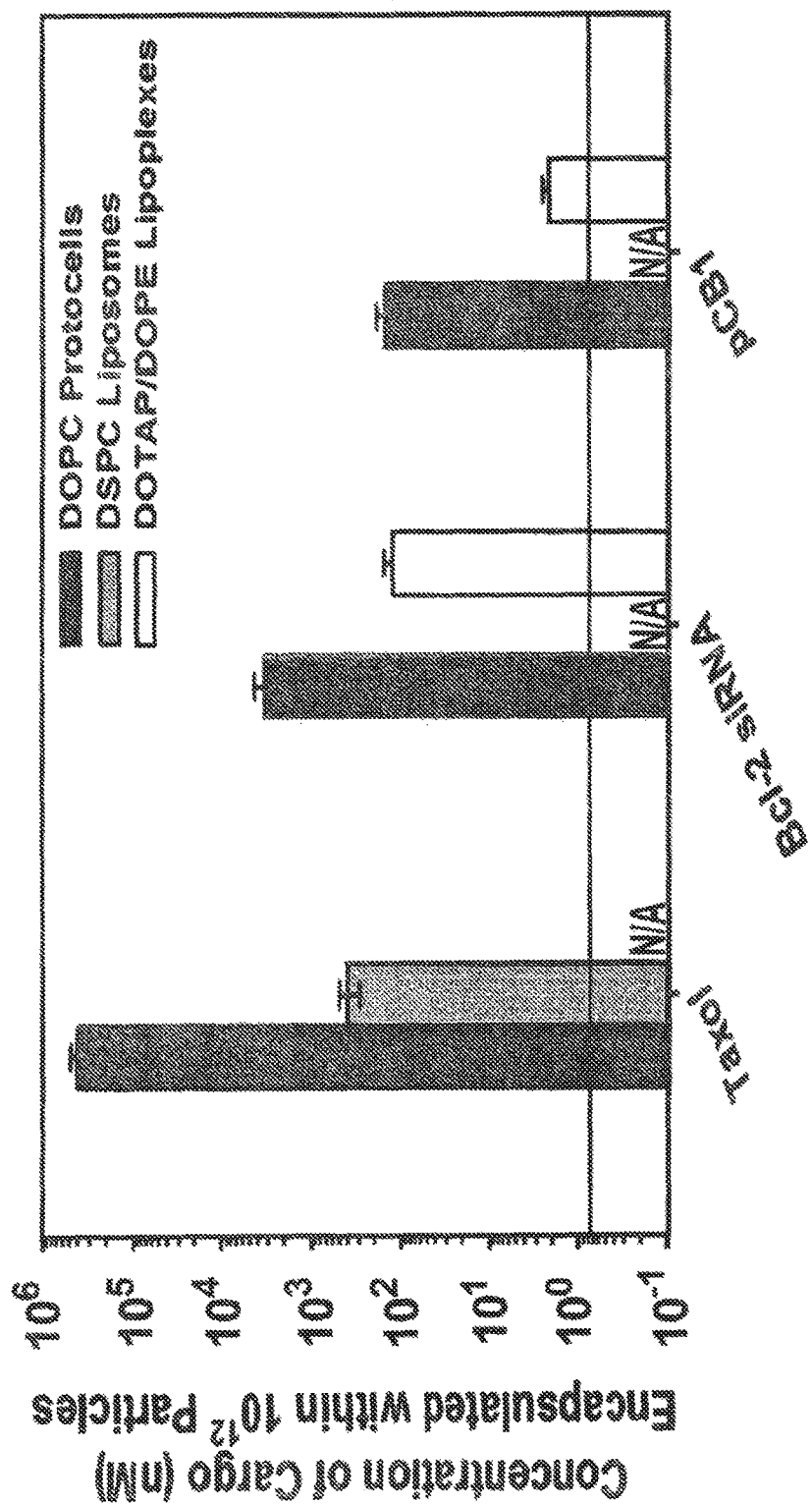
FIG. 11 shows that MC40-targeted protocells selectively deliver high concentrations of taxol, Bcl-2-specific siRNA, and pCB1 to HCC without affecting the viability of hepatocytes. (A) Concentrations of taxol, siRNA that silences expression of Bcl-2, and the CB1 plasmid that can be encapsulated within 10$^{12}$ protocells, liposomes, or lipoplexes. Red bars indicate how taxol and pCB1 concentrations change when both are loaded within protocells. Blue bars indicate how taxol, siRNA, and pCB1 concentrations change when all three are loaded within protocells or when siRNA and pCB1 are loaded within lipoplexes. (B) Confocal fluorescence microscopy image showing the intracellular distributions of Oregon Green® 488-labeled taxol (green), Alexa Fluor® 594-labeled siRNA (red), and Cy5-labeled pDNA (white) upon delivery to Hep3B via MC40-targeted protocells. Cells were incubated with a 1000-fold excess of MC40-targeted protocells for 24 hours at 37° C. prior to being fixed and stained with Hoechst 33342 (blue). Scale bars=10 µm. (C) Fractions of Hep3B, SNU-398, and hepatocyte cells that become arrested in $G_2$/M phase upon exposure to 10 nM of taxol and/or 5 pM of pCB1 for 48 hours at 37° C. Fractions were normalized against the percentage of logarithmically-growing cells in $G_2$/M. (D) The percentage of Hep3B, SNU-398, and hepatocyte cells that become positive for Alexa Fluor® 647-labeled annexin V and propidium iodide (PI) upon exposure to 10 nM of taxol, 250 pM of Bcl-2-specific siRNA, and/or 5 pM of pCB1 for 48 hours at 37° C. In (C) and (D), 'pCB1' refers to pCB1 that was packaged and delivered non-specifically to cells using a mixture of DOTAP and DOPE (1:1 w/w). In all experiments, protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. Liposomes were composed of DSPC with 5 wt % DMPE, 30 wt % cholesterol, and 10 wt % PEG-2000 (16:0) and were modified with 0.015 wt % MC40 and 0.500 wt % H5WYG. Lipoplexes were composed of a DOTAP:DOPE (1:1 w/w) mixture and were modified with 10 wt % PEG-2000, 0.015 wt % MC40, and 0.500 wt % H5WYG. pCB1 was modified with the NLS in all experiments. All error bars represent 95% confidence intervals (1.96σ) for n=3.
Figure 11B:
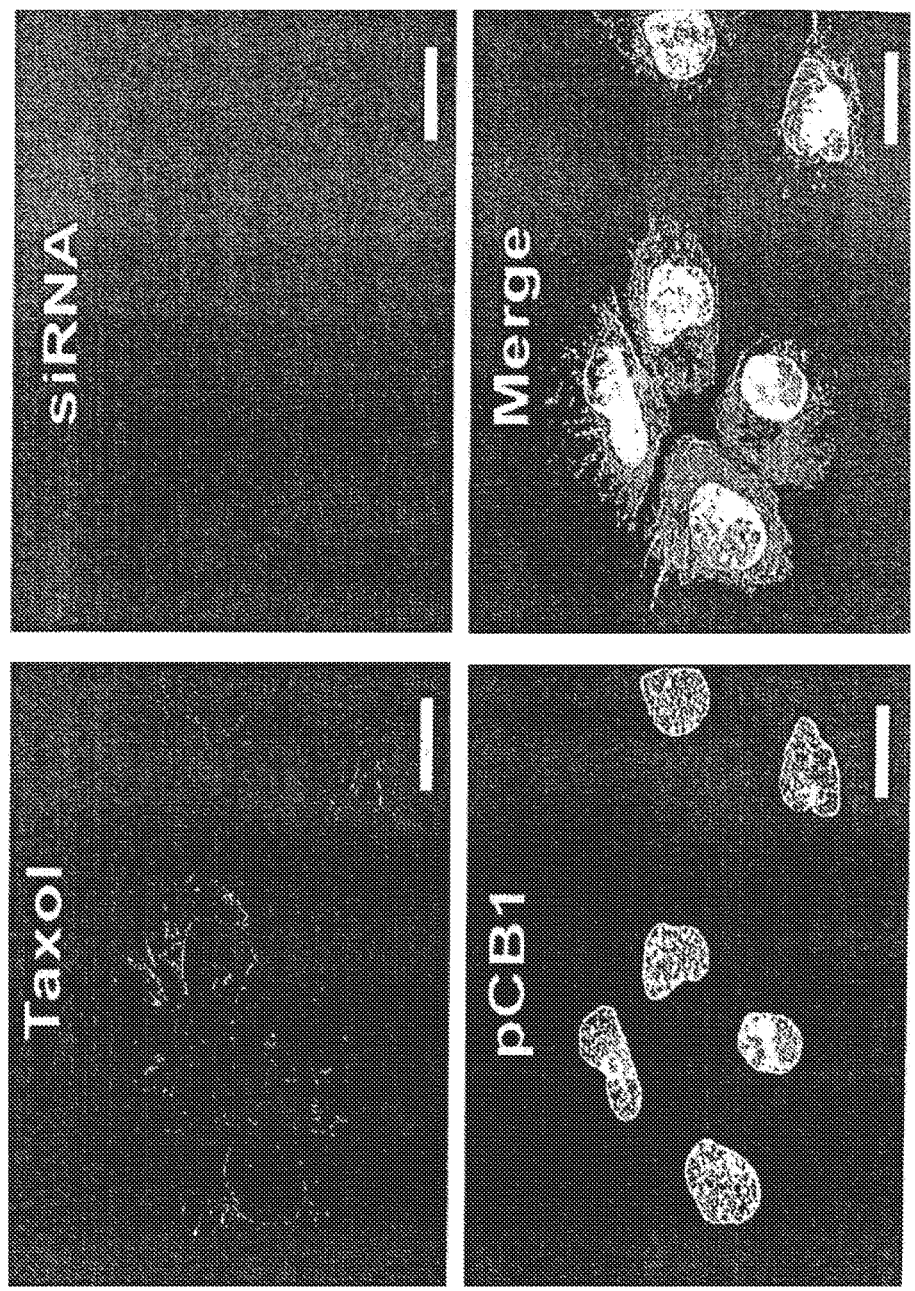
Figure 11C:
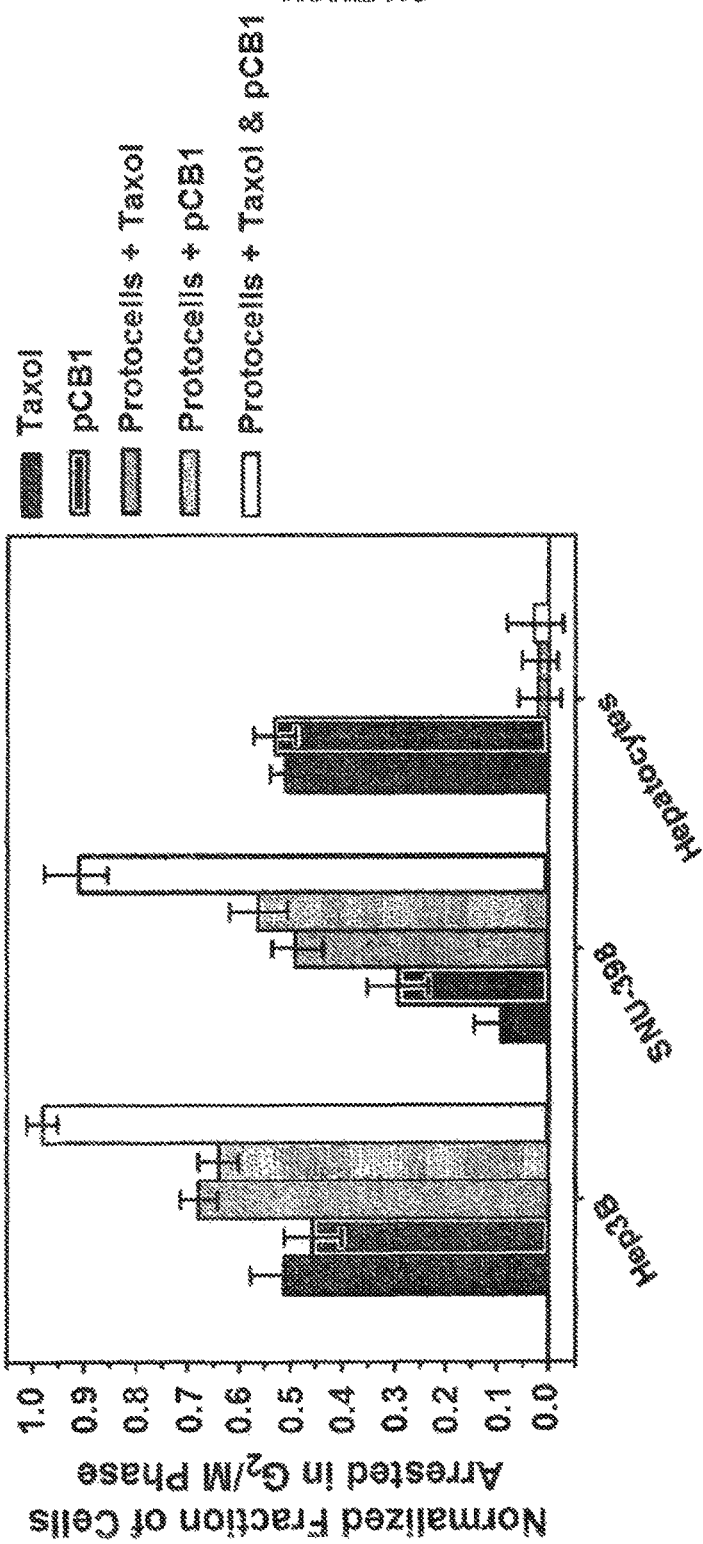

FIG. 11(A) shows the concentrations of taxol, siRNA that silence expression of Bcl-2, and the CB1 plasmid that can be encapsulated within $10^{12}$ protocells, liposomes, or lipoplexes. Red bars in FIG. 11A indicate how taxol and pCB1 concentrations change when both are loaded within protocells. Blue bars indicate how taxol, siRNA, and pCB1 concentrations change when all three are loaded within protocells or when siRNA and pCB1 are loaded within lipoplexes. FIG. 11(B) provides a confocal fluorescence microscopy image showing the intracellular distributions of Oregon Green® 488-labeled taxol (green), Alexa Fluor® 594-labeled siRNA (red), and Cy5-labeled pDNA (white) upon delivery to Hep3B via MC40-targeted protocells. Cells were incubated with a 1000-fold excess of MC40-targeted protocells for 24 hours at 37° C. prior to being fixed and stained with Hoechst 33342 (blue). Scale bars=10 μm. FIG. 11(C) shows the fractions of Hep3B, SNU-398, and hepatocyte cells that become arrested in $G_2$/M phase upon exposure to 10 nM of taxol and/or 5 pM of pCB1 for 48 hours at 37° C. Fractions were normalized against the percentage of logarithmically-growing cells in $G_2$/M. FIG. 11(D) shows the percentage of Hep3B, SNU-398, and hepatocyte cells that become positive for Alexa Fluor® 647-labeled annexin V and propidium iodide (PI) upon exposure to 10 nM of taxol, 250 pM of Bcl-2-specific siRNA, and/or 5 pM of pCB1 for 48 hours at 37° C. In (C) and (D), 'pCB1' refers to pCB1 that was packaged and delivered non-specifically to cells using a mixture of DOTAP and DOPE (1:1 w/w). In all experiments, protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. Liposomes were composed of DSPC with 5 wt % DMPE, 30 wt % cholesterol, and 10 wt % PEG-2000 (16:0) and were modified with 0.015 wt % MC40 and 0.500 wt % H5WYG. Lipoplexes were composed of a DOTAP: DOPE (1:1 w/w) mixture and were modified with 10 wt % PEG-2000, 0.015 wt % MC40, and 0.500 wt % H5WYG. pCB1 was modified with the NLS in all experiments. All error bars represent 95% confidence intervals (1.96σ) for n=3.

Vector Map for the CB1 Plasmid

Figure 12:
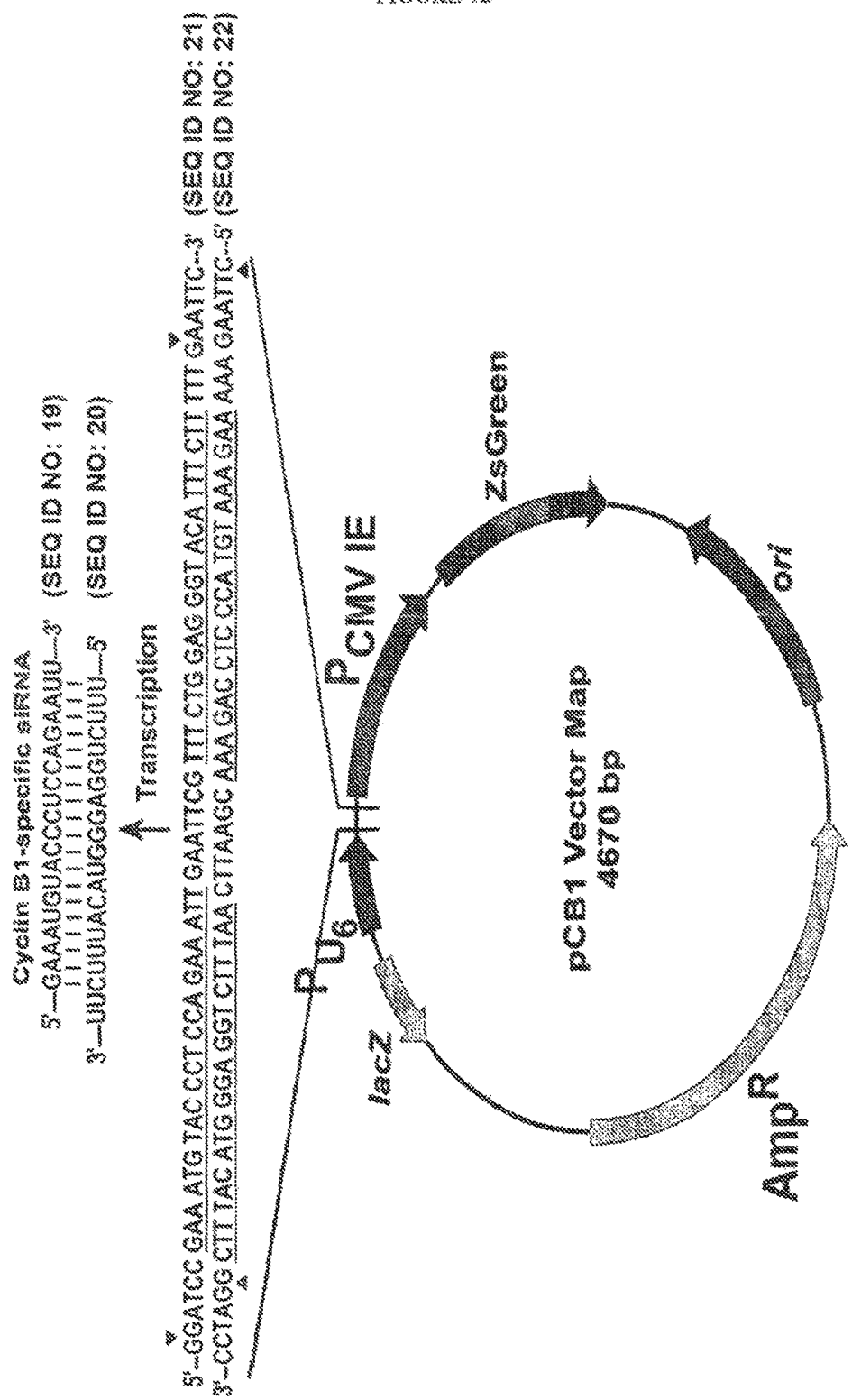
FIG. 12 provides a vector map for the CB1 plasmid. The CB1 plasmid (pCB1) was constructed from the RNAi-Ready pSIREN-RetroQ-ZsGreen vector (Clontech Laboratories, Inc.; Mountain View, Calif.) and the pNEB193 vector (New England BioLabs, Inc.; Ipswich, Mass.). pCB1 encodes a cyclin B1-specific small hairpin RNA (shRNA) and a *Zoanthus* sp. green fluorescent protein (ZsGreen). Constitutive shRNA expression is driven by the RNA Pol III-dependent human U6 promoter ($P_{U6}$), while constitutive ZsGreen expression is driven by the immediate early promoter of cytomegalovirus ($P_{CMV\ IE}$). The ori and $Amp^R$ elements enable propagation of the plasmid in *E. coli*. The DNA sequences that encode the sense and antisense strands of the cyclin B1-specific shRNA are underlined and are flanked by the restriction enzyme sites (BamHI in red and EcoRI in blue) that were employed to introduce the dsDNA oligonucleotide into the pSIREN vector.

As shown in FIG. 12, the CB1 plasmid (pCB1) was constructed from the RNAi-Ready pSIREN-RetroQ-ZsGreen vector (Clontech Laboratories, Inc.; Mountain View, Calif.) and the pNEB193 vector (New England BioLabs, Inc.; Ipswich, Mass.). pCB1 encodes a cyclin B1-specific small hairpin RNA (shRNA) [Yuan, et al., Oncogene (2006) 25, 1753-1762] and a *Zoanthus* sp. green fluorescent protein (ZsGreen). Constitutive shRNA expression is driven by the RNA Pol III-dependent human U6 promoter ($P_{U6}$), while constitutive ZsGreen expression is driven by the immediate early promoter of cytomegalovirus ($P_{CMV\,IE}$). The ori and Amp$^R$ elements enable propagation of the plasmid in *E. coli*. The DNA sequences that encode the sense and antisense strands of the cyclin B1-specific shRNA are underlined and are flanked by the restriction enzyme sites (BamHI in red and EcoRI in blue) that were employed to introduce the dsDNA oligonucleotide into the pSIREN vector.

Characterization of Histone-Packaged pCB1.

Figure 13A:
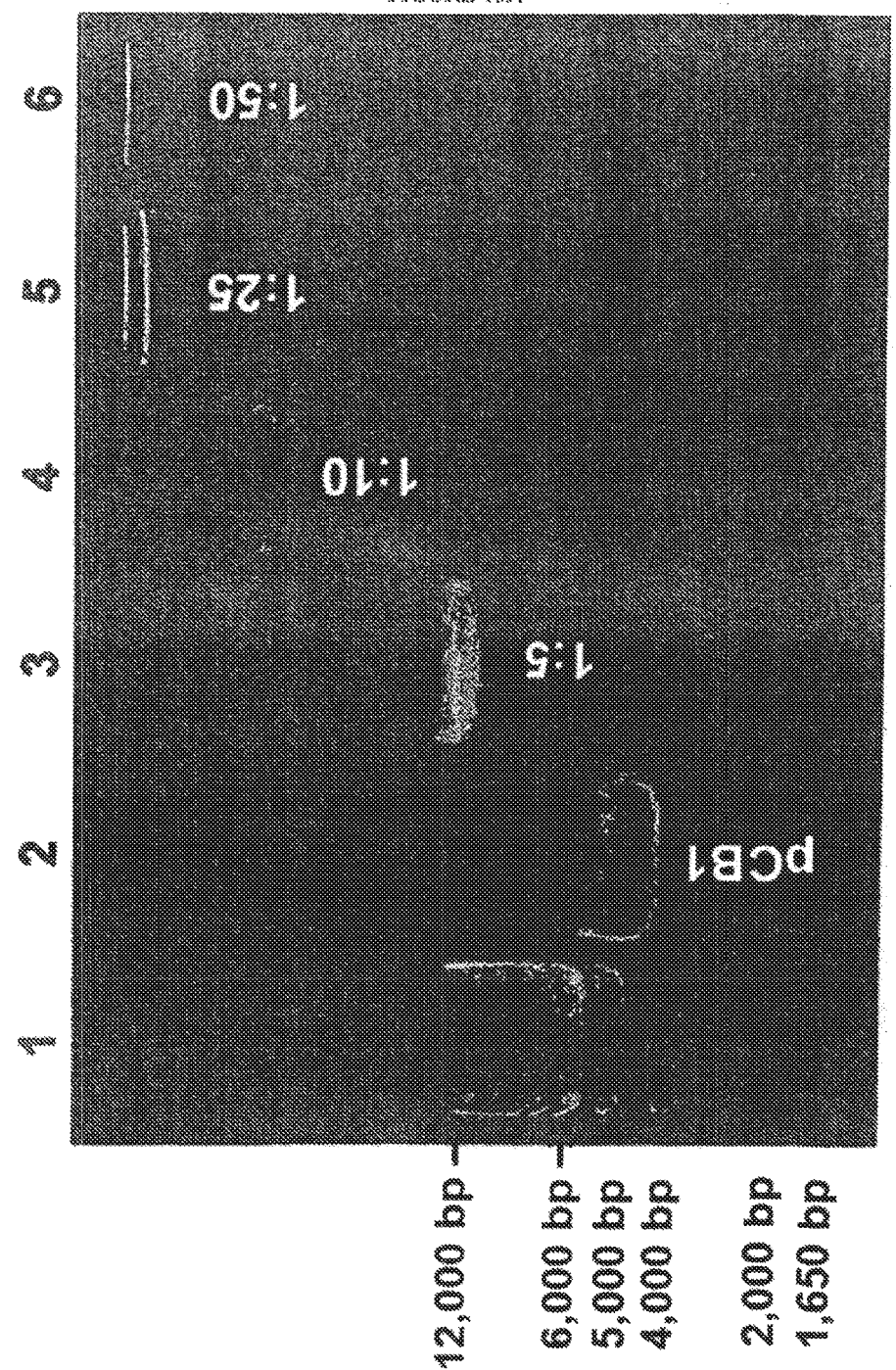
FIG. 13 depicts the characterization of histone-packaged pCB1. (A) Electrophoretic mobility shift assays for pCB1 exposed to increasing concentrations of histones (H1, H2A, H2B, H3, and H4 in a 1:2:2:2:2 molar ratio). The pCB1:histone molar ratio is given for lanes 3-6. Lane 1 contains a DNA ladder, and lane 2 contains pCB1 with no added histones. (B) TEM image of histone-packaged pCB1 (1:50 pCB1:histone molar ratio). Scale bar=50 nm.
Figure 13B:
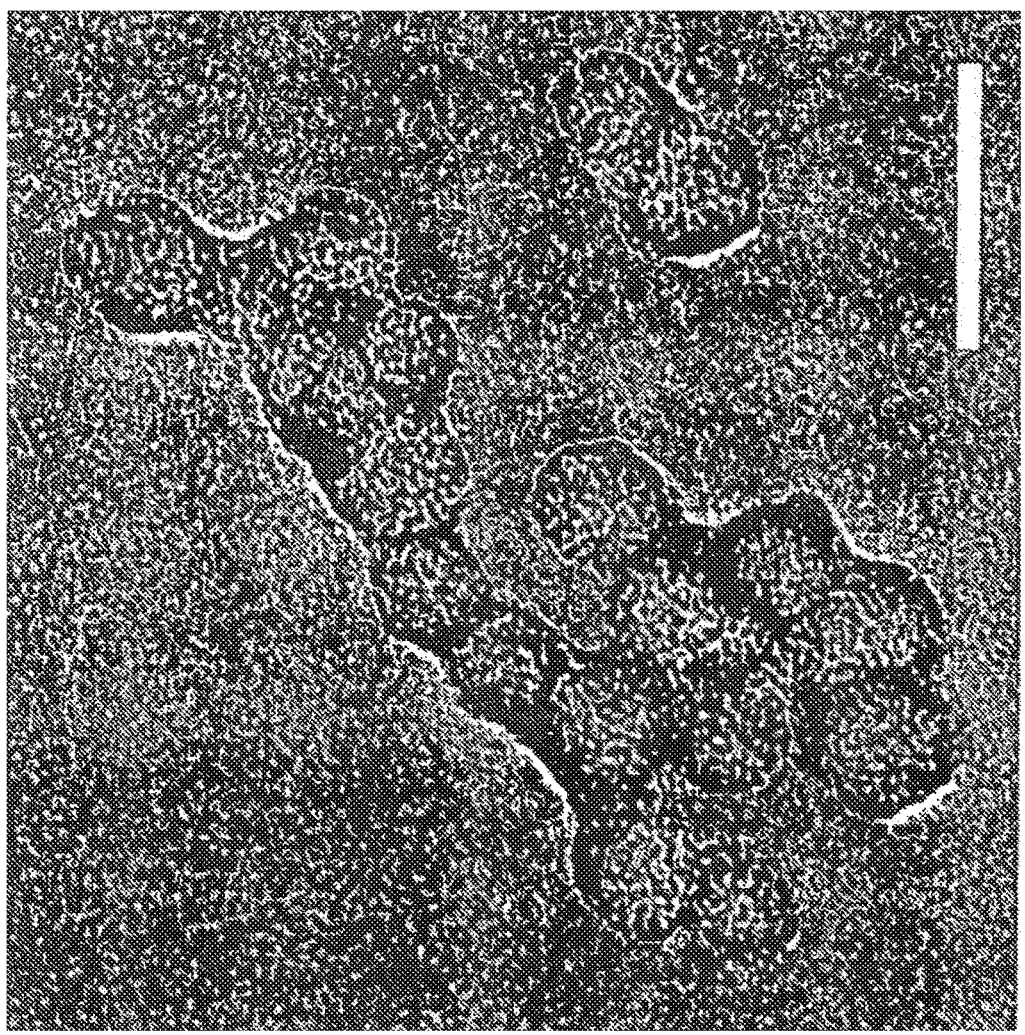

FIG. 13(A) shows the electrophoretic mobility shift assays for pCB1 exposed to increasing concentrations of histones (H1, H2A, H2B, H3, and H4 in a 1:2:2:2:2 molar ratio). The pCB1:histone molar ratio is given for lanes 3-6. Lane 1 contains a DNA ladder, and lane 2 contains pCB1 with no added histones. FIG. 13(B) shows the TEM image of histone-packaged pCB1 (1:50 pCB1:histone molar ratio). Scale bar=50 nm.

Nitrogen Sorption Analysis of Unloaded and pCB1-Loaded Mesoporous Silica Nanoparticles.

FIG. 14(A) Nitrogen sorption isotherms for mesoporous silica nanoparticles before and after loading with histone-packaged pCB1. FIG. 14(B) shows the Brunauer-Emmett-Teller (BET) surface area of mesoporous silica nanoparticles, before and after loading with histone-packaged pCB1. Error bars represent 95% confidence intervals (1.96σ) for n=3.

Small-Angle Neutron Scattering (SANS) Data for DOPC Protocells.

Figure 15:
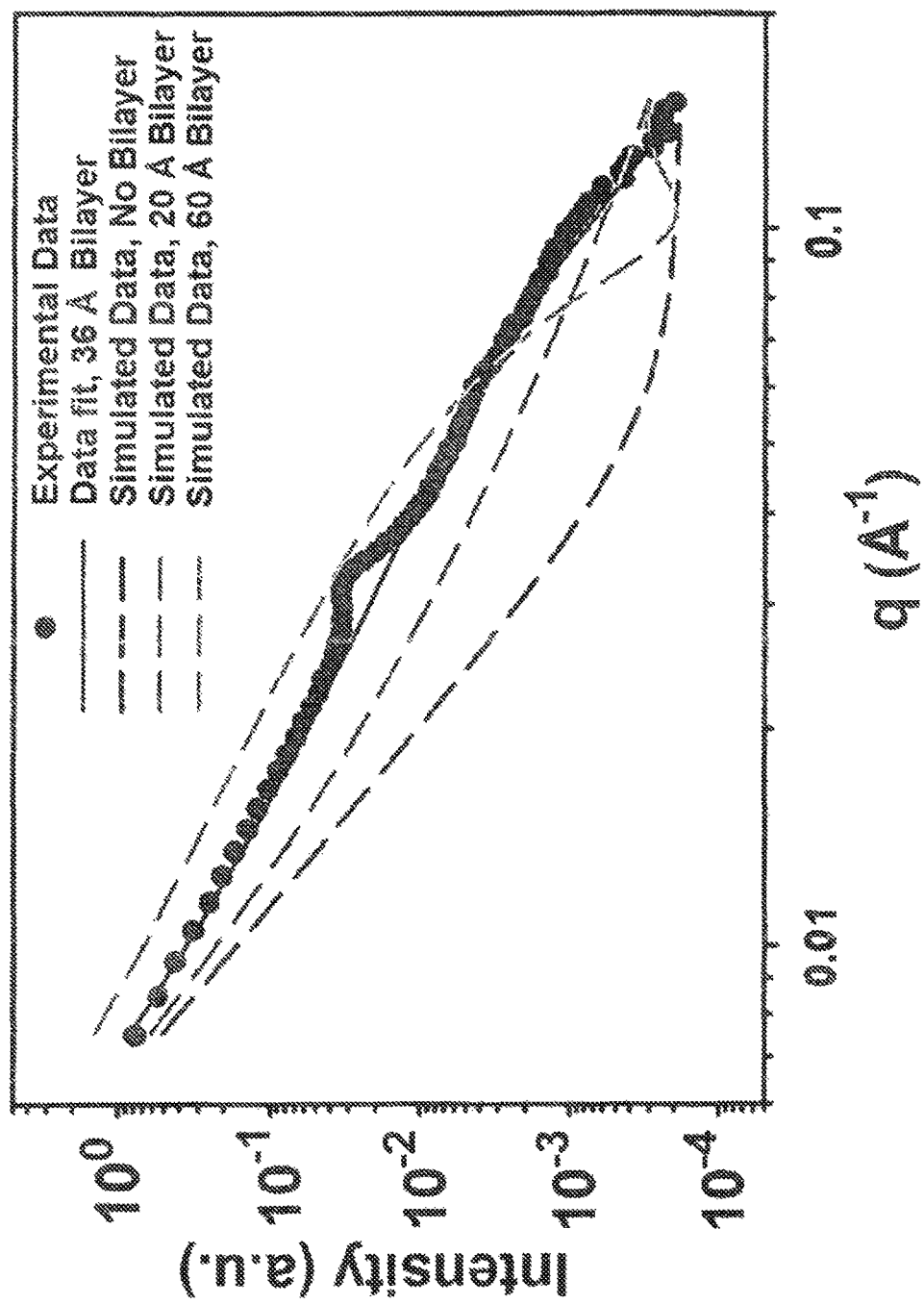
FIG. 15 shows the small-angle neutron scattering (SANS) data for DOPC protocells. The data fit was obtained using a model for polydisperse porous silica spheres with a conformal shell of constant thickness and shows the presence of a 36-Å bilayer at the surface of the silica particles that spans pore openings. Simulated SANS data for bilayer thicknesses of 0, 20, and 60 Å are included for comparison. The measured bilayer thickness of 36 Å is consistent with other neutron studies (33-38 Å) performed on planar supported lipid bilayers and, under these contrast conditions, primarily represents scattering from the hydrogen-rich hydrocarbon core of the lipid bilayer.

FIG. 15 shows SANS data for DOPC protcells. The data fit was obtained using a model for polydisperse porous silica spheres with a conformal shell of constant thickness and shows the presence of a 36-Å bilayer at the surface of the silica particles that spans pore openings. Simulated SANS data for bilayer thicknesses of 0, 20, and 60 Å are included for comparison. The measured bilayer thickness of 36 Å is consistent with other neutron studies (33-38 Å) [see, Ferrari, M. Cancer nanotechnology: Opportunities and challenges. *Nature Reviews Cancer* 5, 161-171 (2005)] performed on planar supported lipid bilayers and, under these contrast conditions, primarily represents scattering from the hydrogen-rich hydrocarbon core of the lipid bilayer. Experimental data also demonstrates the presence of 299.2-Å pores, determined by dividing 0.0315 Å$^{-1}$ (i.e. the q-value for the peak in the experimental data, which is caused by scattering from pores) into 2π. SANS data were obtained on the LQD beam line at LANSCE (Los Alamos National Laboratories) using a 5% (v/v) protocell suspension in 100% $D_2O$ PBS buffer. Data were fit using the NCNR SANS data analysis package (NIST).

Protocells Protect Encapsulated DNA from Nuclease Degradation.

Figure 16:
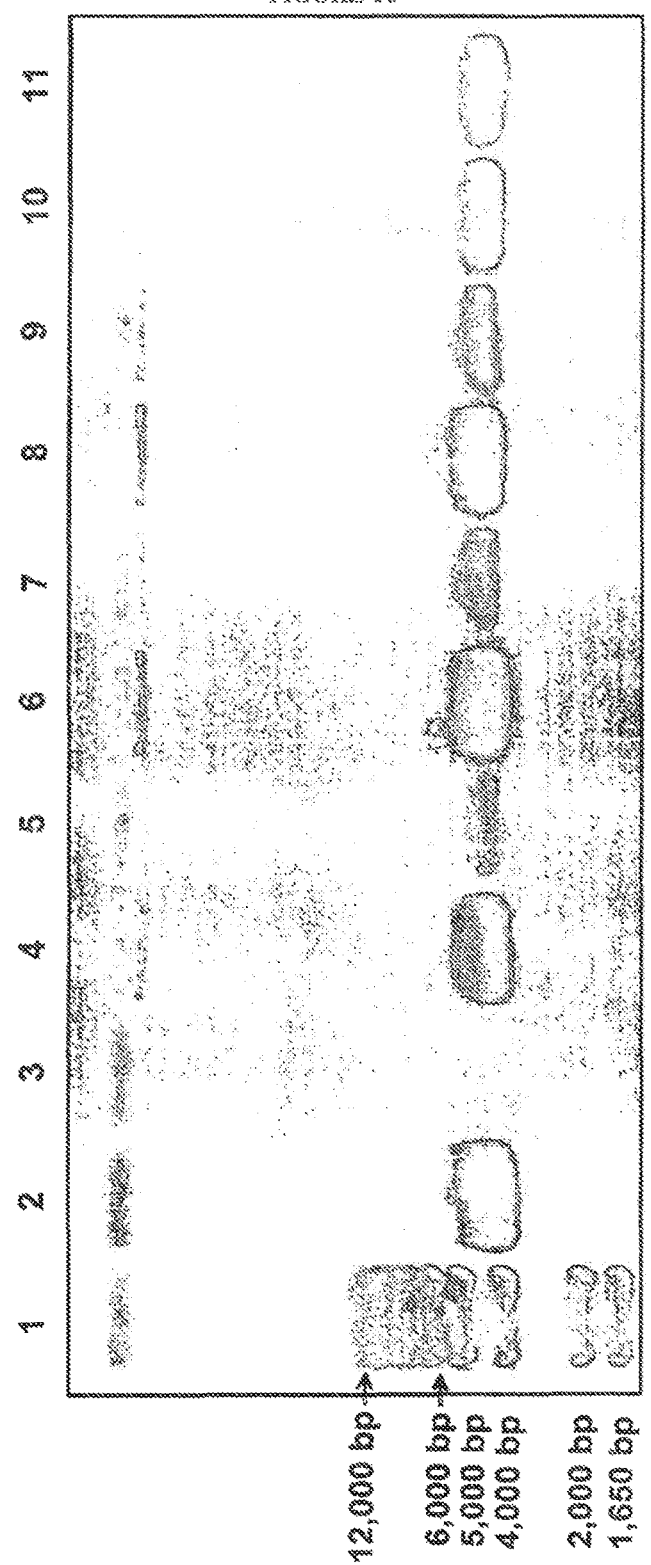
FIG. 16 shows that protocells protect encapsulated DNA from nuclease degradation. Agarose gel electrophoresis of DNase I-treated pCB1 (lane 3), histone-packaged pCB1 (lane 5), pCB1 packaged with a 1:1 (w/w) mixture of DOTAP and DOPE (lane 7), pCB1 loaded in protocells with cationic cores (lane 9), and histone-packaged pCB1 loaded in protocells with anionic cores (lane 11). Naked pCB1 (lane 2), pCB1 released from histones (lane 4), pCB1 released from DOTAP/DOPE lipoplexes (lane 6), pCB1 released from protocells with cationic cores (lane 8), and histone-packaged pCB1 released from protocells with anionic cores (lane 10) are included for comparison. Lane 1 contains a DNA ladder. Samples were incubated with DNase I (1 unit per 50 ng of DNA) for 30 minutes at room temperature, and pCB1 release was stimulated using 1% SDS.

FIG. 16 shows the results of agarose gel electrophoresis of DNase I-treated pCB1 (lane 3), histone-packaged pCB1 (lane 5), pCB1 packaged with a 1:1 (w/w) mixture of DOTAP and DOPE (lane 7), pCB1 loaded in protocells with cationic cores (lane 9), and histone-packaged pCB1 loaded in protocells with anionic cores (lane 11). Naked pCB1 (lane 2), pCB1 released from histones (lane 4), pCB1 released from DOTAP/DOPE lipoplexes (lane 6), pCB1 released from protocells with cationic cores (lane 8), and histone-packaged pCB1 released from protocells with anionic cores (lane 10) are included for comparison. Lane 1 contains a DNA ladder. Samples were incubated with DNase I (1 unit per 50 ng of DNA) for 30 minutes at room temperature, and pCB1 release was stimulated using 1% SDS.

FIG. 17 shows the Zeta potential (ζ) values for mesoporous silica nanoparticles ('unmodified cores'), mesoporous silica nanoparticles that were soaked in 20% (v/v) APTES for 12 hours at room temperature ('APTES-modified cores'), the CB1 plasmid ('pCB1'), histone-packaged pCB1 ('pCB1-histonecomplex'), and pCB1 packaged with a 1:1 (w/w) mixture of DOTAP and DOPE ('DOTAP/DOPE Lipoplexes'). Zeta potential measurements were conducted in 0.5×PBS (pH 7.4). Error bars represent 95% confidence intervals (1.96σ) for n=3.

Representative Forward Scatter-Side Scatter (FSC-SSC) Plots and FL-1 Histograms Used to Determine the Percentage of Cells Positive for ZsGreen Expression in FIG. 6 and S-16 (A)-(D)

Figure 18A:
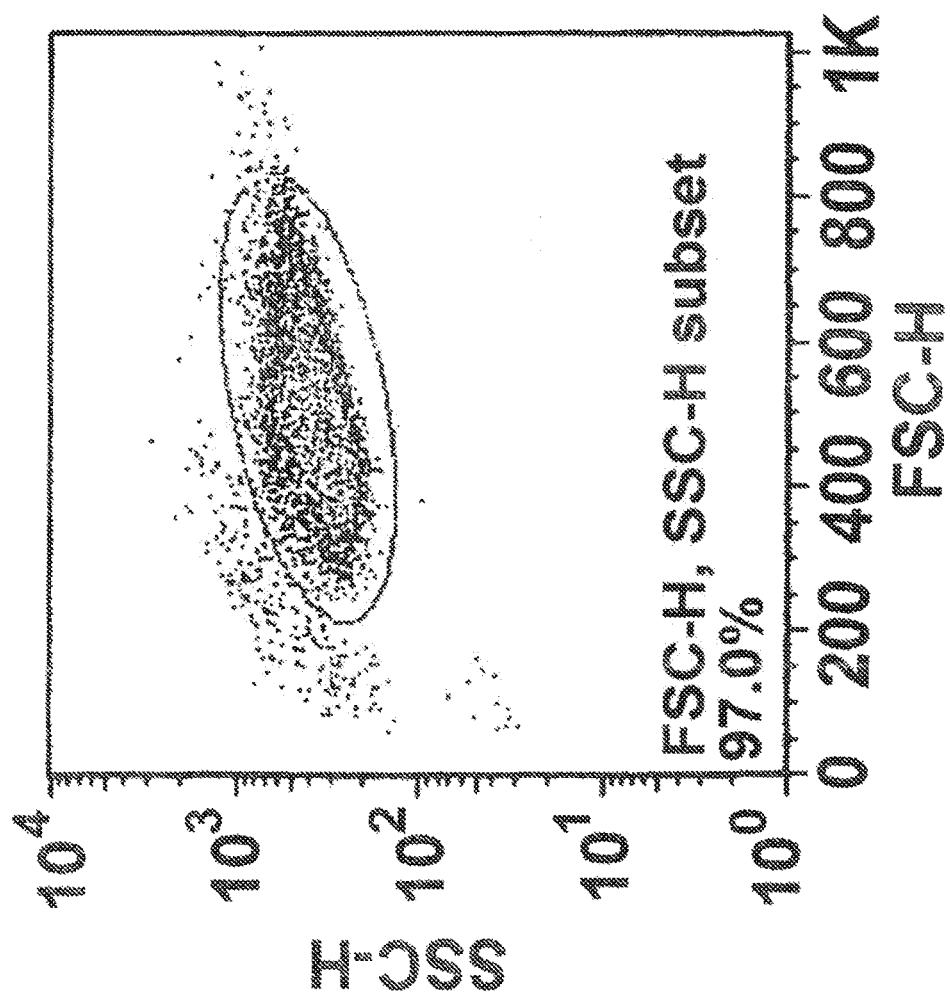
FIG. 18 shows the representative forward scatter-side scatter (FSC-SSC) plots and FL-1 histograms used to determine the percentage of cells positive for ZsGreen expression in FIGS. 6 and 24. (A)-(D) FSC-SSC plots (A and C) and the corresponding FL-1 histograms (B and D, respectively) for ZsGreen-negative cells that were (A) or were not (C) gated to exclude cellular debris. Mean fluorescence intensity (MFI) values for the FL-1 channel are given in (B) and (D). (E)-(H) FSC-SSC plots (E and G) and the corresponding FL-1 histograms (F and H, respectively) for ZsGreen-positive cells that were (E) or were not (G) gated to exclude cellular debris. Gates on (F) and (H) correspond to the percentage of cells with MFI≤282, i.e. 100× the MFI of ZsGreen-negative cells (see panel D).
Figure 18B:
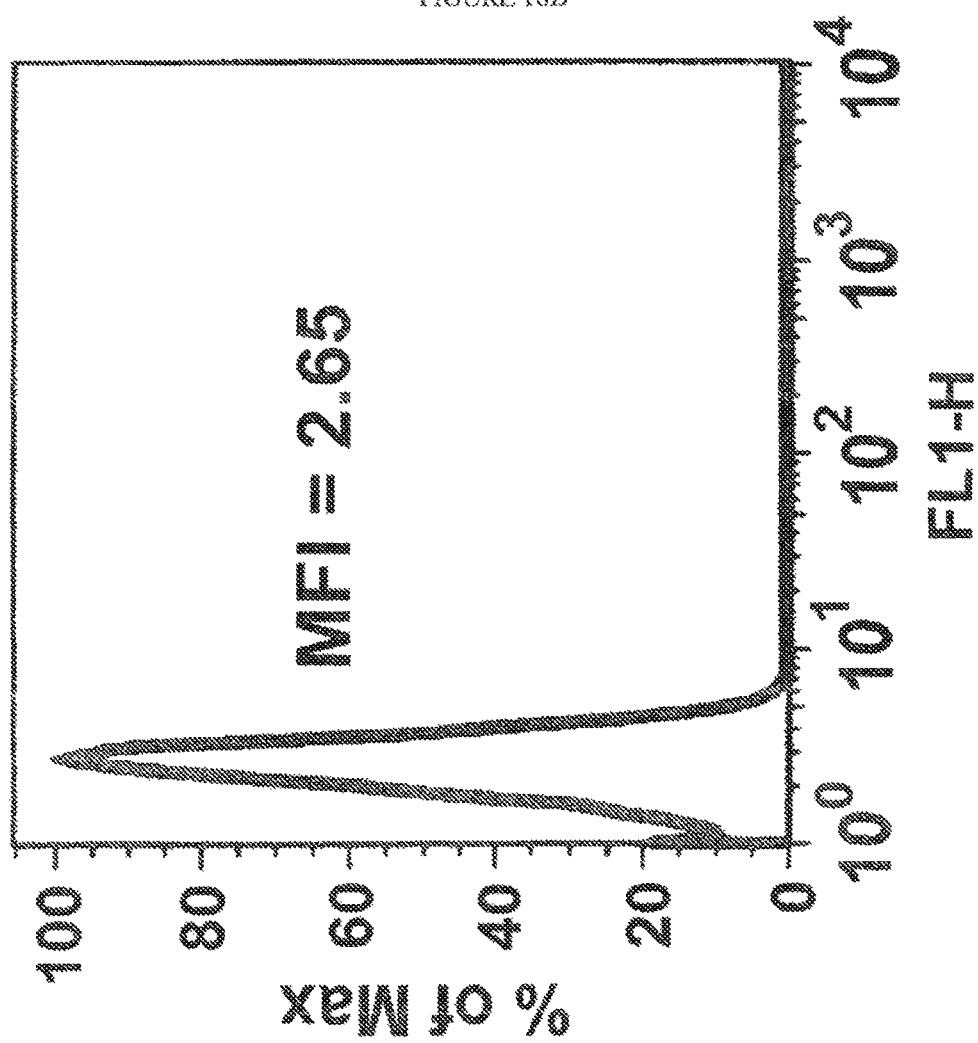
Figure 18G:
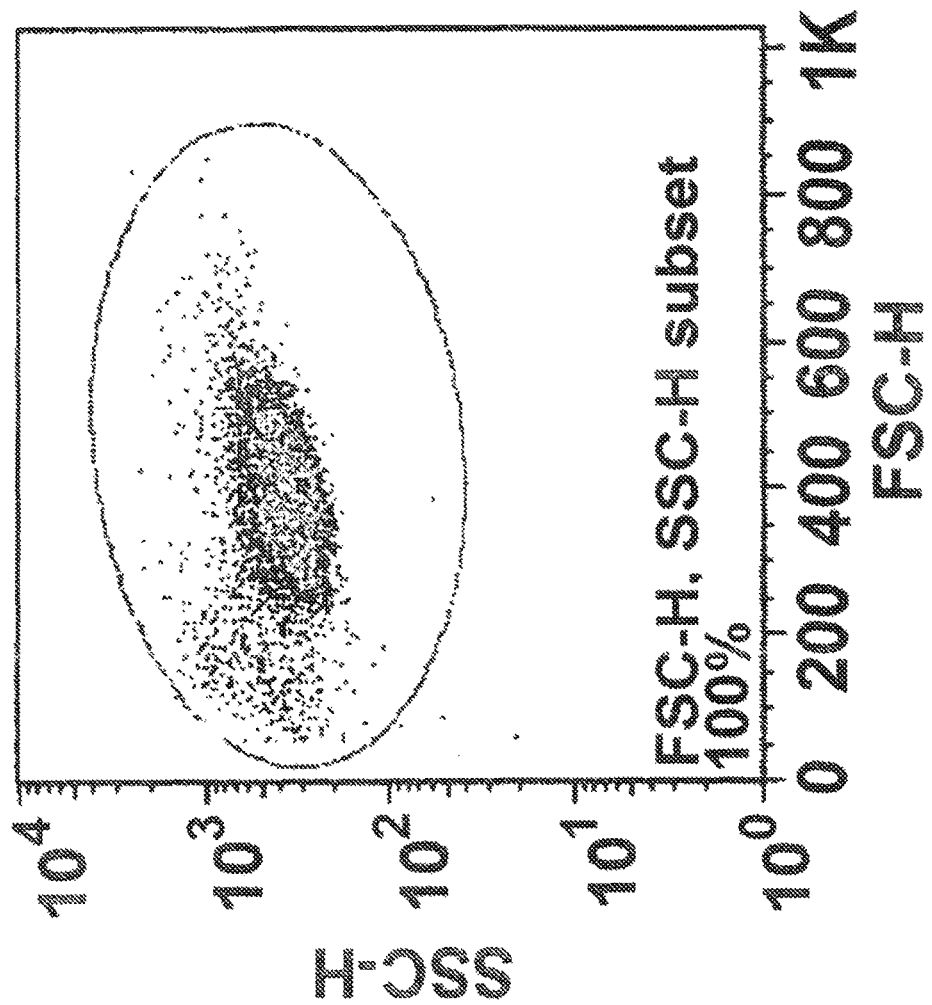

FIG. 18 shows the FSC-SSC plots (A and C) and the corresponding FL-1 histograms (B and D, respectively) for ZsGreen-negative cells that were (A) or were not (C) gated to exclude cellular debris. Mean fluorescence intensity (MFI) values for the FL-1 channel are given in (B) and (D). (E)-(H) FSC-SSC plots (E and G) and the corresponding FL-1 histograms (F and H, respectively) for ZsGreen-positive cells that were (E) or were not (G) gated to exclude cellular debris. Gates on (F) and (H) correspond to the percentage of cells with MFI≤282, i.e. 100× the MFI of ZsGreen-negative cells (see panel D).

Identification of the MC40 Targeting Peptide.

Figure 19:
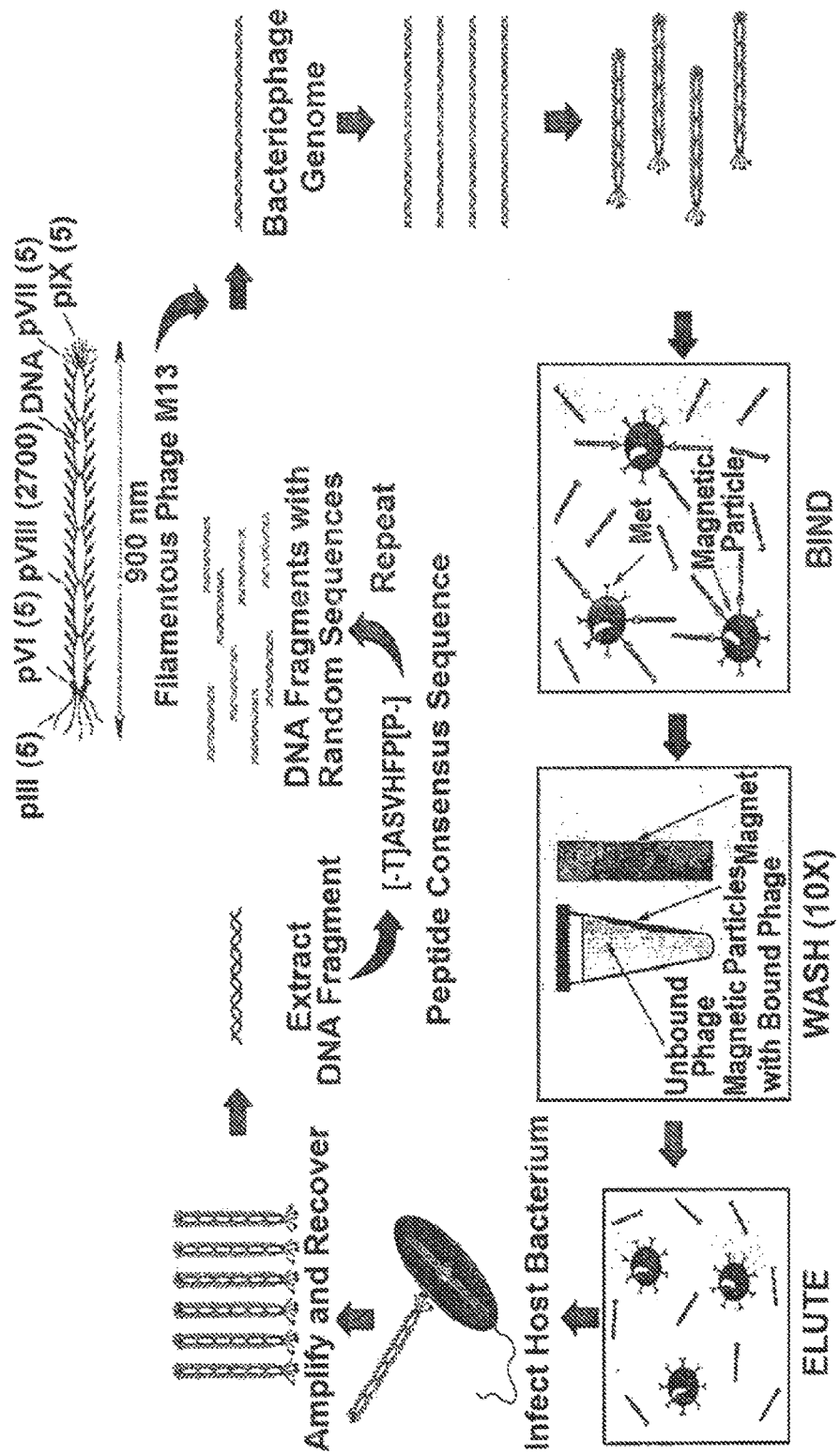
FIG. 19 shows the identification of the MC40 targeting peptide. Schematic set forth in the figure depicts the process used to select the MC40 targeting peptide. Peptides at $1 \times 10^{11}$ pfu/mL were incubated with 100 nM of recombinant human Met (rhMet), fused to the Fc domain of human IgG, for 1 hour at room temperature. Protein A or protein G-coated magnetic particles were used to affinity capture Met-phage complexes and were subsequently washed 10 times with TBS (50 mM Tris-HCl with 150 mM NaCl, pH 7.4) to remove unbound phage. Bound phage clones were eluted with a low-pH buffer (0.2 M glycine with 1 mg/mL BSA, pH 2.2), and elutants were amplified via infection of the host bacterium (*E. coli* ER2738).

FIG. 19 provides a schematic depicting the process used to select the MC40 targeting peptide from a Ph.D.™-7 phage display library (New England BioLabs, Inc.; Ipswich, Mass.). 1×10¹¹ pfu/mL were incubated with 100 nM of recombinant human Met (rhMet), fused to the Fc domain of human IgG, for 1 hour at room temperature. Protein A or protein G-coated magnetic particles were used to affinity capture Met-phage complexes and were subsequently washed 10 times with TBS (50 mM Tris-HCl with 150 mM NaCl, pH 7.4) to remove unbound phage. Bound phage clones were eluted with a low-pH buffer (0.2 M glycine with 1 mg/mL BSA, pH 2.2), and elutants were amplified via infection of the host bacterium (*E. coli* ER2738). Pursuant to the schematic, five rounds of affinity selection were performed using increasingly stringent conditions: the Met concentration was decreased from 100 nM to 50 nM to 10 nM, the incubation time was reduced from 1 hour to 30 minutes to 15 minutes, and the concentration of Tween-20 added to the wash buffer was increased from 0% (v/v) to 0.1% to 0.5%. Peptides specific for protein A and protein G were avoided by alternating rounds of selection between protein A-coated magnetic particles and protein G-coated magnetic particles. After five rounds of selection, DNA was recovered from 40 individual clones and sequenced using the −96 gIII primer provided with the Ph.D.™-7 kit. The sequences which have the greatest binding activity against the MET receptor are presented as follows:

```
                                        SEQ ID NO: 1
    ASVHFPP (Ala-Ser-Val-His-Phe-Pro-Pro)

SEQ ID NO: 2
    TATFWFQ (Thr-Ala-Thr-Phe-Trp-Phe-Gln)

SEQ ID NO: 3
    TSPVALL (Thr-Ser-Pro-Val-Ala-Leu-Leu)

SEQ ID NO: 4
    IPLKVHP (Ile-Pro-Leu-Lys-Val-His-Pro)

SEQ ID NO: 5
    WPRLTNM (Trp-Pro-Arg-Leu-Thr-Asn-Met)
```

Characterization of the MC40 Targeting Peptide.

Figure 20B:
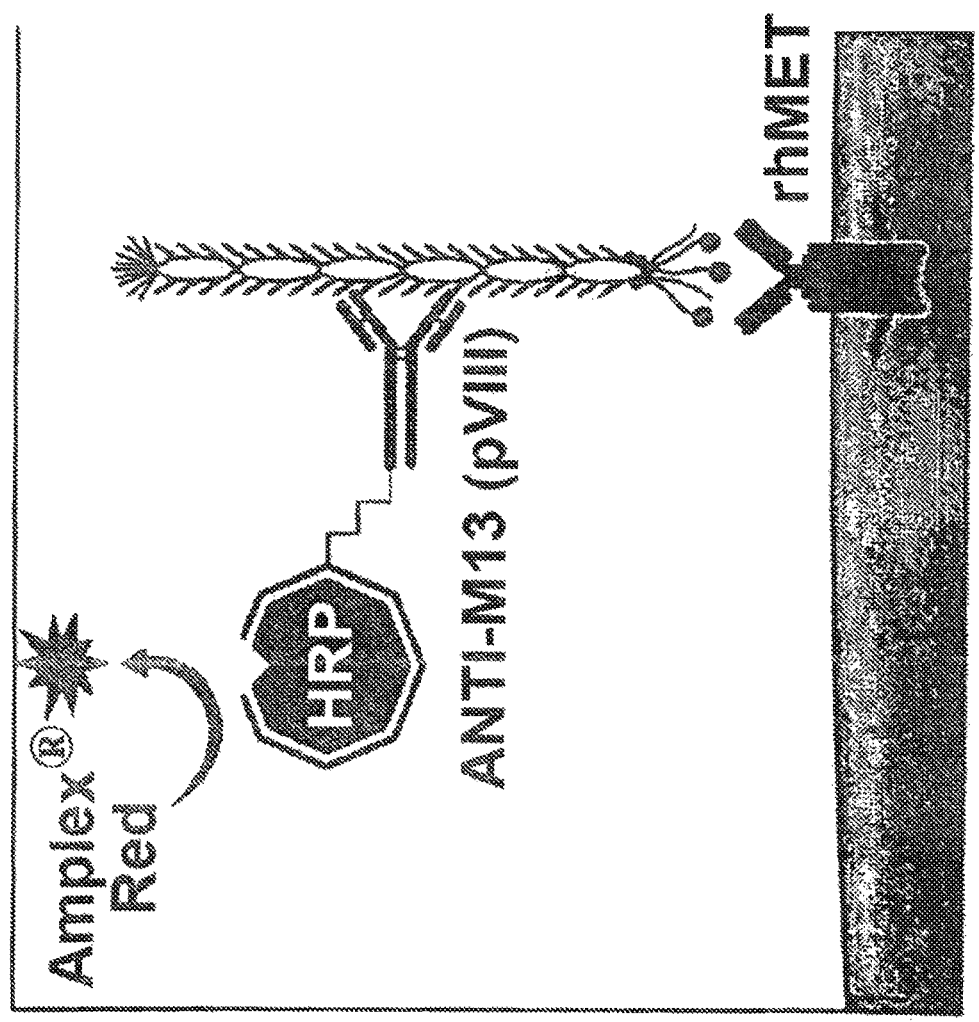
FIG. 20 shows the characterization of the MC40 targeting peptide. (A) Peptide sequence alignment after the $5^{th}$ round of selection; the predominant sequence, ASVHFPP, is similar to the emboldened portion of a previously-identified Met-specific 12-mer, YLFSVHWPPLKA, SEQ ID NO: 15, Zhao, et al. *ClinCancerRes* 2007; 13(20 6049-6055). Phage clones displaying the target-unrelated HAIYPRH peptide (~10%) (SEQ ID NO: 16, Brammer, et al., *Anal. Biochem.* 373(2008)88-98) were omitted from the sequence alignment. (B) and (C) The degree to which affinity-selected phage clones bound to rhMet was determined via enzyme-linked immunosorbent assay (ELISA). The ELISA scheme, depicted in (B), is described in the Materials and Methods section. ELISA results are shown in (C). (D) Sequence alignment after peptides that do not bind to Met were removed. The consensus sequence depicted in Figure S-9 was determined from this alignment. (E) and (F) Flow cytometry scatter plots for Hep3B (E) and hepatocytes (F) exposed to either (1) an Alexa Fluor® 488-labeled monoclonal antibody against Met AND an irrelevant phage clone (TPDWLFP) (SEQ ID NO: 17) and an Alexa Fluor® 546-labeled monoclonal antibody against M13 phage (blue dots) or (2) an Alexa Fluor® 488-labeled monoclonal antibody against Met AND the MC40 clone AND an Alexa Fluor® 546-labeled monoclonal antibody against M13 phage (orange dots). Untreated cells (red dots) were used to set voltage parameters for the FL-1 (Alexa Fluor® 488 fluorescence) and FL-2 (Alexa Fluor® 546 fluorescence) channels.
Figure 20F:
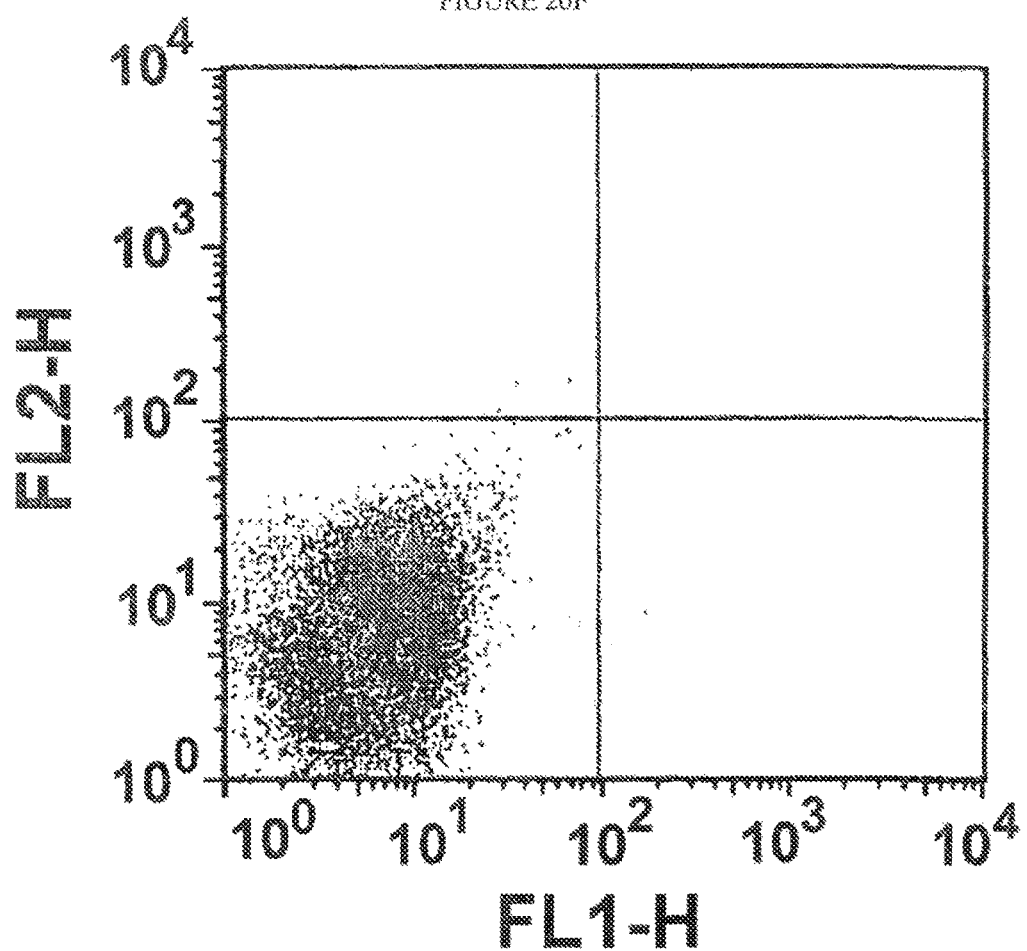

FIG. 20(A) shows the peptide sequence alignment after the 5$^{th}$ round of selection; the predominant sequence, ASVHFPP, is similar to the emboldened portion of a previously-identified Met-specific 12-mer, YLFSVHWPPLKA SEQ ID NO: 15,). Phage clones displaying the target-unrelated HAIYPRH peptide (~10%) (SEQ ID NO: 16) were omitted from the sequence alignment. FIGS. 20(B) and (C) show the degree to which affinity-selected phage clones bound to rhMet was determined via enzyme-linked immunosorbent assay (ELISA). The ELISA scheme, depicted in (B), is described in the Materials and Methods section. ELISA results are shown in (C). FIG. 20(D) shows the sequence alignment after peptides that do not bind to Met were removed. The consensus sequence depicted in FIG. 20 was determined from this alignment. FIGS. 20(E) and (F) show the flow cytometry scatter plots for Hep3B (E) and hepatocytes (F) exposed to either (1) an Alexa Fluor® 488-labeled monoclonal antibody against Met AND an irrelevant phage clone (TPDWLFP) AND an Alexa Fluor® 546-labeled monoclonal antibody against M13 phage (blue dots) or (2) an Alexa Fluor 488-labeled monoclonal antibody against Met AND the MC40 clone AND an Alexa Fluor® 546-labeled monoclonal antibody against M13 phage (orange dots). Untreated cells (red dots) were used to set voltage parameters for the FL-1 (Alexa Fluor® 488 fluorescence) and FL-2 (Alexa Fluor® 546 fluorescence) channels.

Sample Binding Curves for MC40-Targeted Protocells Exposed to Hep3B.

Figure 21:
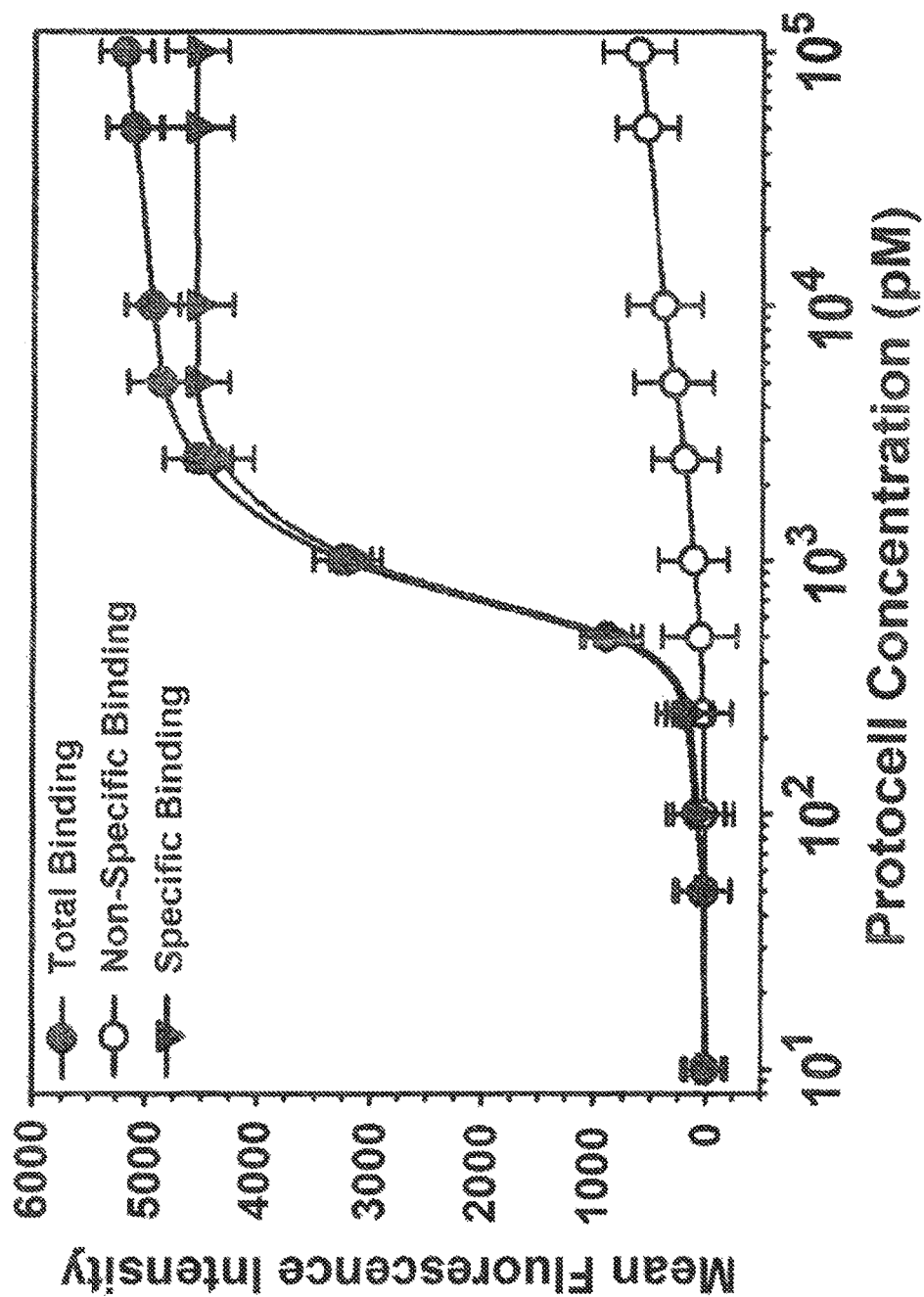
FIG. 21 shows sample binding curves for MC40-targeted protocells exposed to Hep3B.

To determine the dissociation constants in FIG. 8A, 1×10⁶ Hep3B or hepatocytes were pre-treated with cytochalasin D to inhibit endocytosis and incubated with various concentrations of Alexa Fluor® 647-labeled, MC40-targeted protocells for 1 hour at 37° C. Flow cytometry was used to determine mean fluorescence intensities for the resulting cell populations, which were plotted against protocell concentrations to obtain total binding curves. Non-specific binding was determined by incubating cells with Alexa Fluor® 647-labeled, MC40-targeted protocells in the presence of a saturating concentration of unlabeled hepatocyte growth factor. Specific binding curves were obtained by subtracting non-specific binding curves from total binding curves; $K_d$ values were calculated from specific binding curves. In the experiments which are depicted in FIG. 21, protocell SLBs were composed of DOPC with 5 wt % DOPE, 30 wt % cholesterol, and 10 wt % PEG-2000 (18:1) and were modified with 0.015 wt % (~6 peptides/particle) of the MC40 targeting peptide; the corresponding $K_d$ value is 1050±142 pM. All error bars represent 95% confidence intervals (1.96σ) for n=5.

MC40-Targeted Protocells are Internalized Via Receptor-Mediated Endocytosis and, in the Absence of the H5WYG Peptide, are Directed to Lysosomes.

FIG. 22(A) shows the average number of MC40-targeted protocells internalized by each Hep3B or hepatocyte cell within one hour at 37° C. $1\times10^6$ cells were incubated with various concentrations of protocells in the absence (−) or presence (+) of a saturating concentration (100 μg/mL) of human hepatocyte growth factor (HGF), and flow cytometry was used to determine the average number of particles associated with each cell, as described by Ashley, et al. *Nature Materials*, 2011, May; 10(5):389-97. Protocells were labeled with NBD and pHrodo™ to distinguish surface-bound particles from those internalized into acidic intracellular compartments (respectively). Error bars represent 95% confidence intervals (1.96σ) for n=3. (B) Pearson's correlation coefficients (r-values) between protocells and: (1) Rab5, (2) Rab7, (3) Lysosomal-Associated Membrane Protein 1 (LAMP-1), or (4) Rab11a. Hep3B cells were incubated with a 1000-fold excess of Alexa Fluor® 594-labeled protocells for 1 hour at 37° C. before being fixed, permeabilized, and incubated with Alexa Fluor® 488-labeled antibodies against Rab5, Rab7, LAMP-1, or Rab11a. SlideBook software was used to determine r-values, which are expressed as the mean value±the standard deviation for n=3×50 cells. Differential Interference Contrast (DIC) images were employed to define the boundaries of Hep3B cells so that pixels outside of the cell boundaries could be disregarded when calculating r-values. Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG.

Histone-Packaged pCB1, when Modified with a NLS and Delivered Via MC40-Targeted Protocells, Becomes Concentrated in the Nuclei of HCC Cells in a Time-Dependent Manner.

Figure 23A:
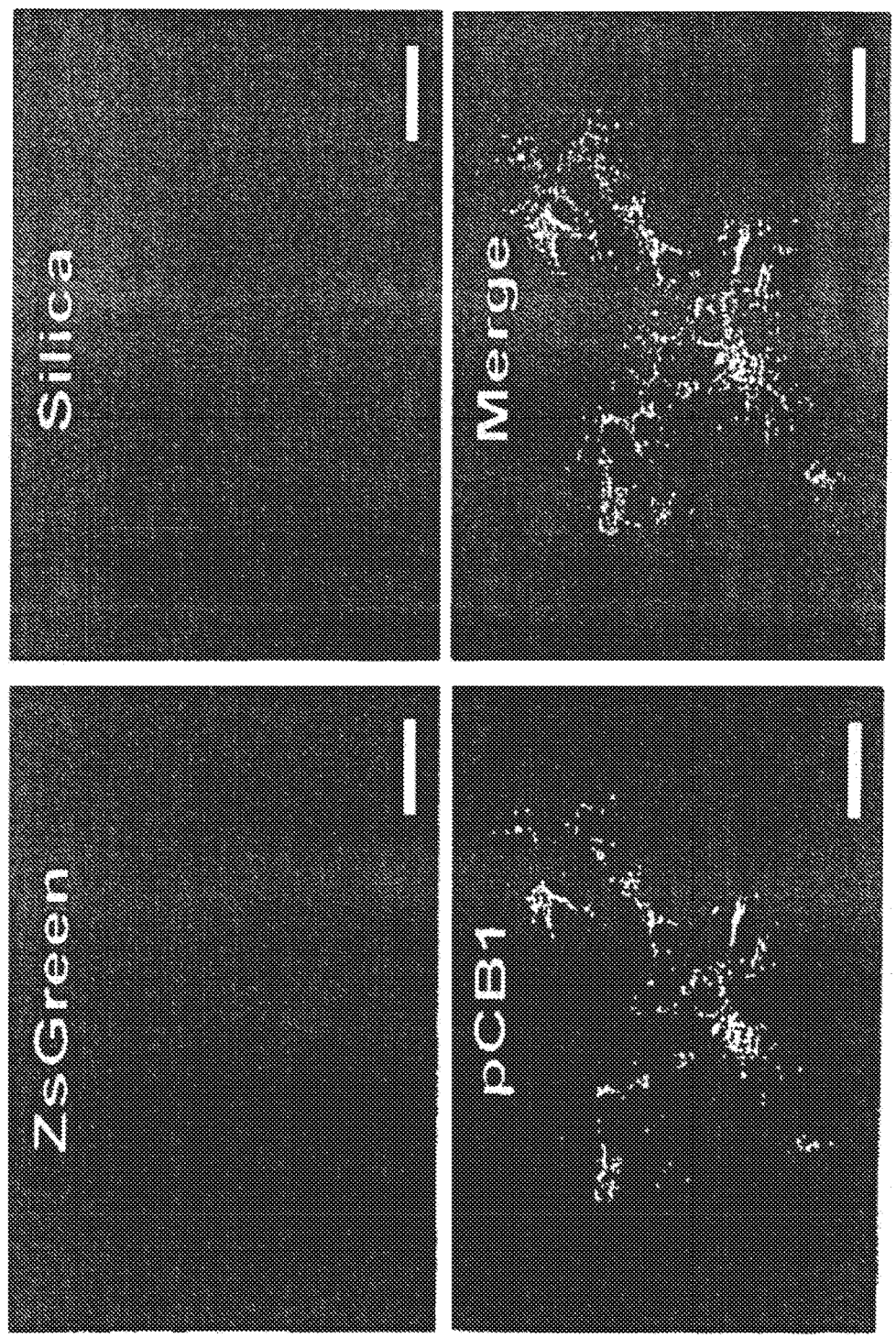
Figure 23B:
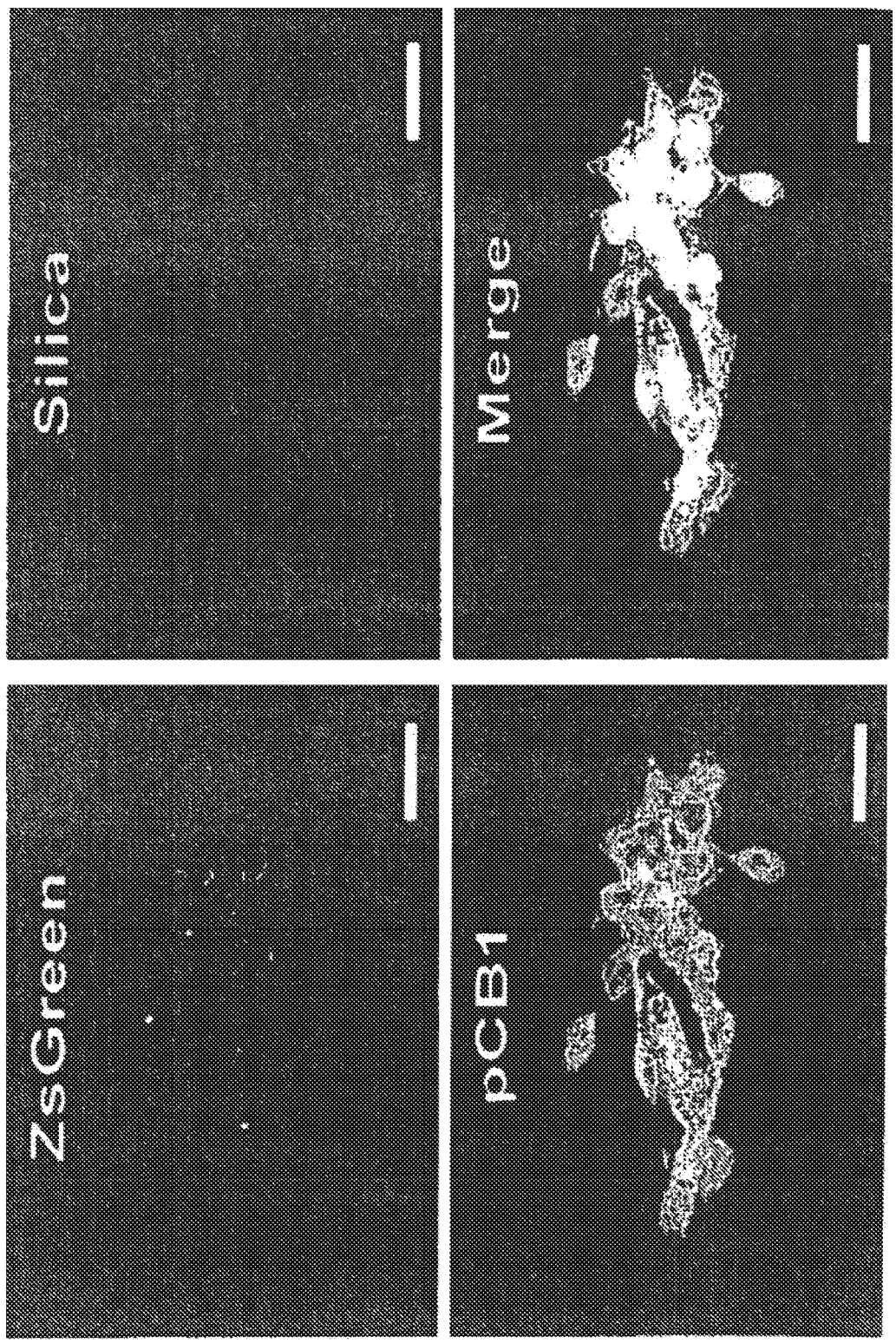
Figure 23C:
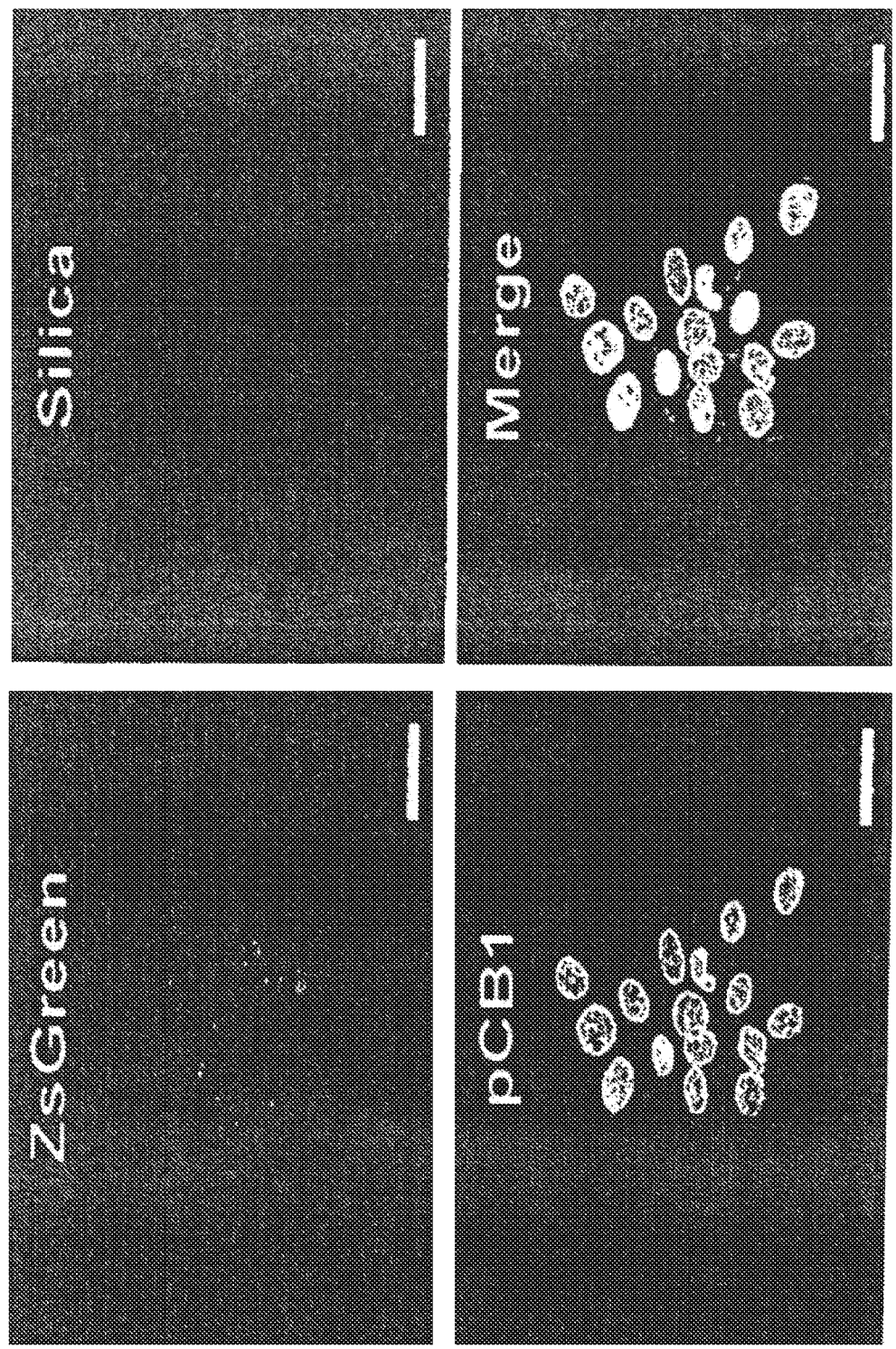
Figure 23D:
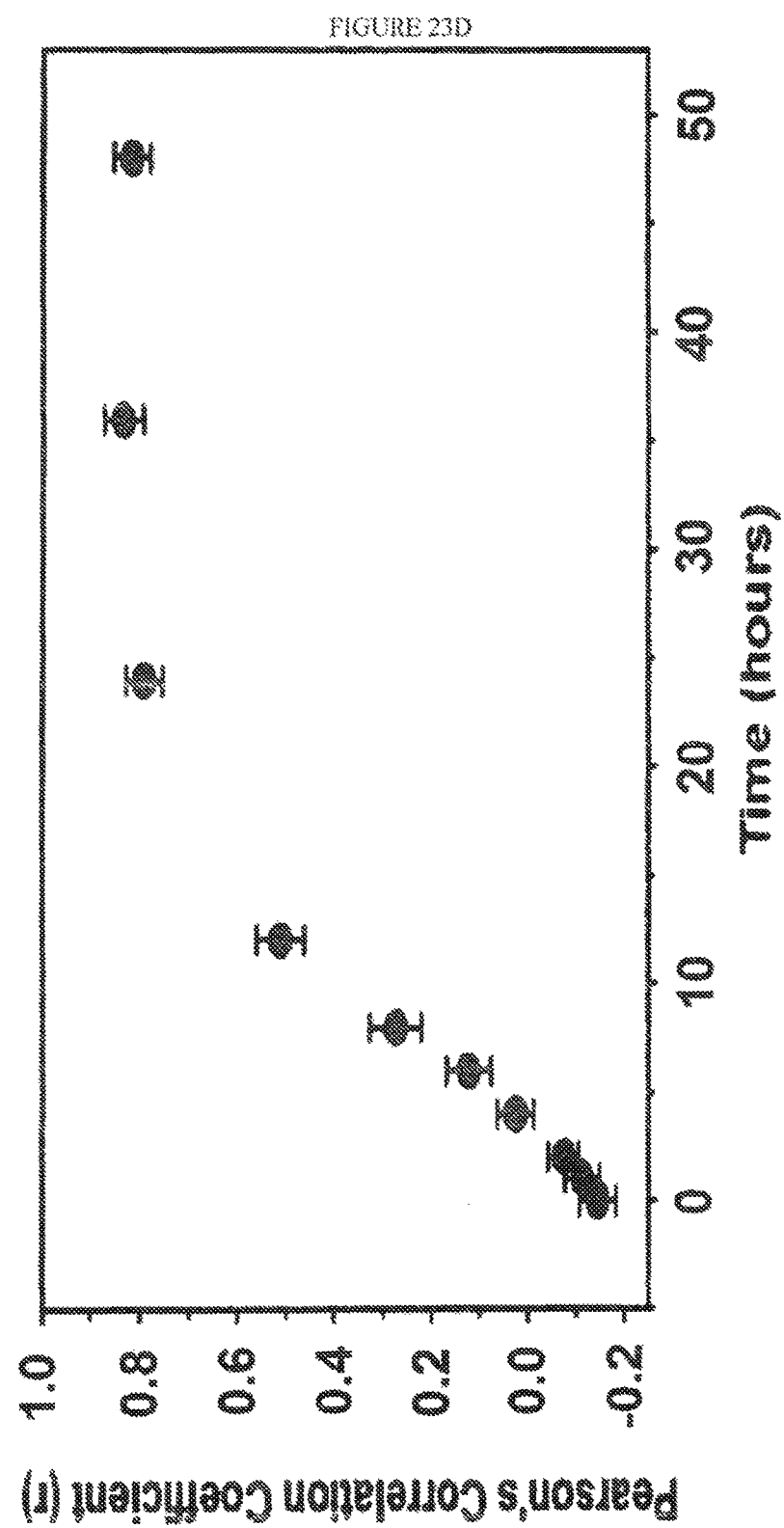
Figure 24B:
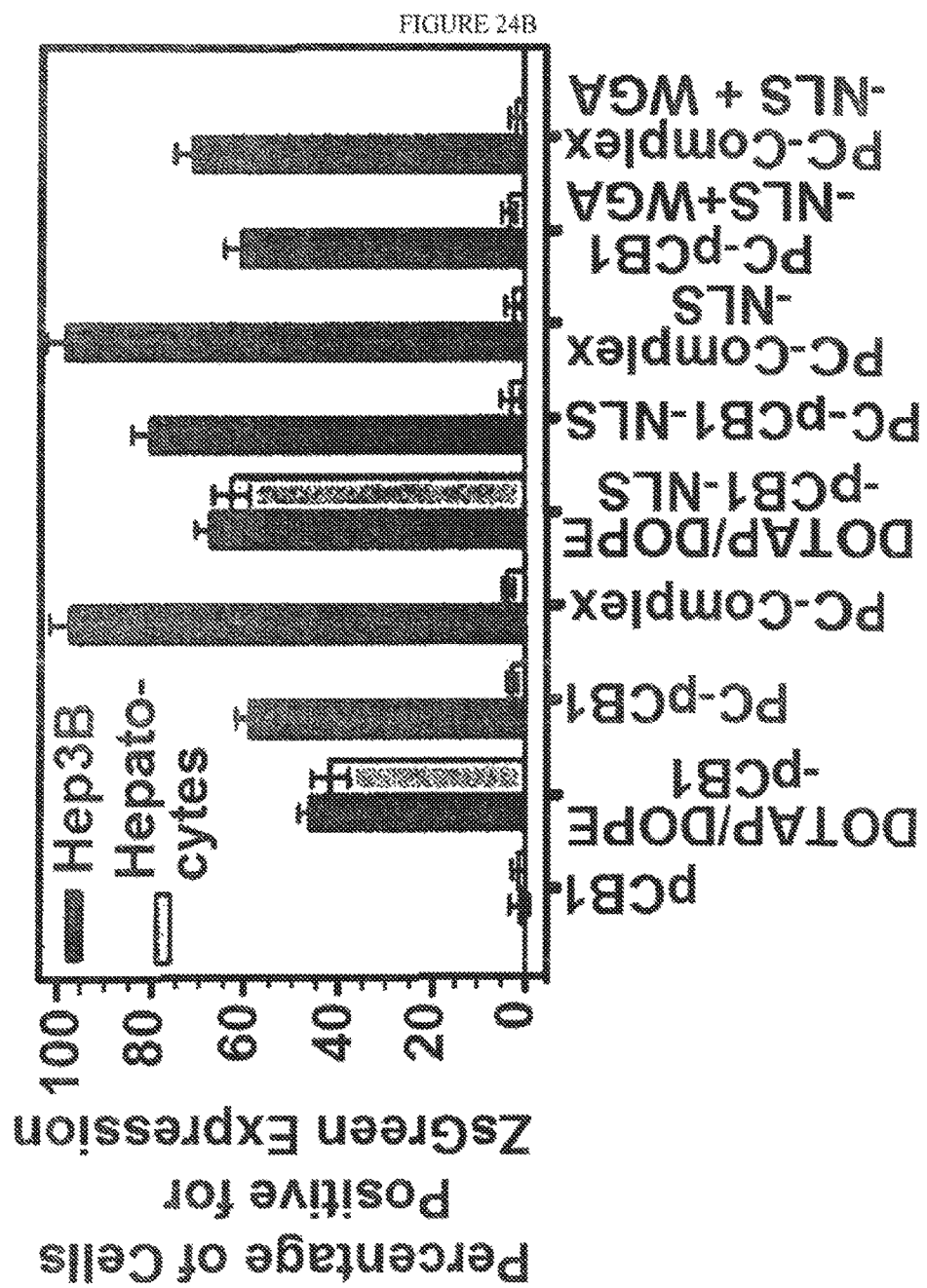
Figure 24F:
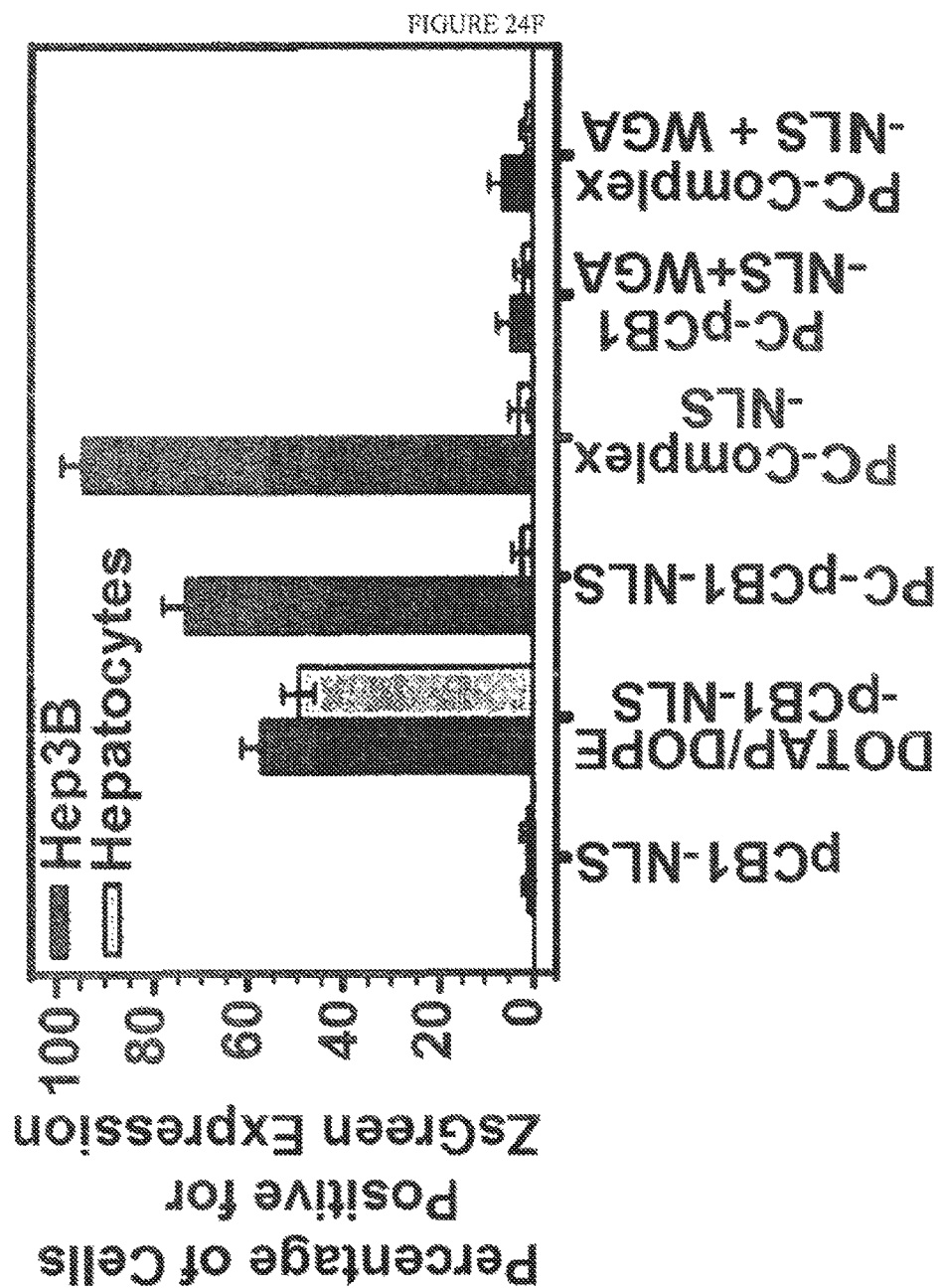
Figure 24G:
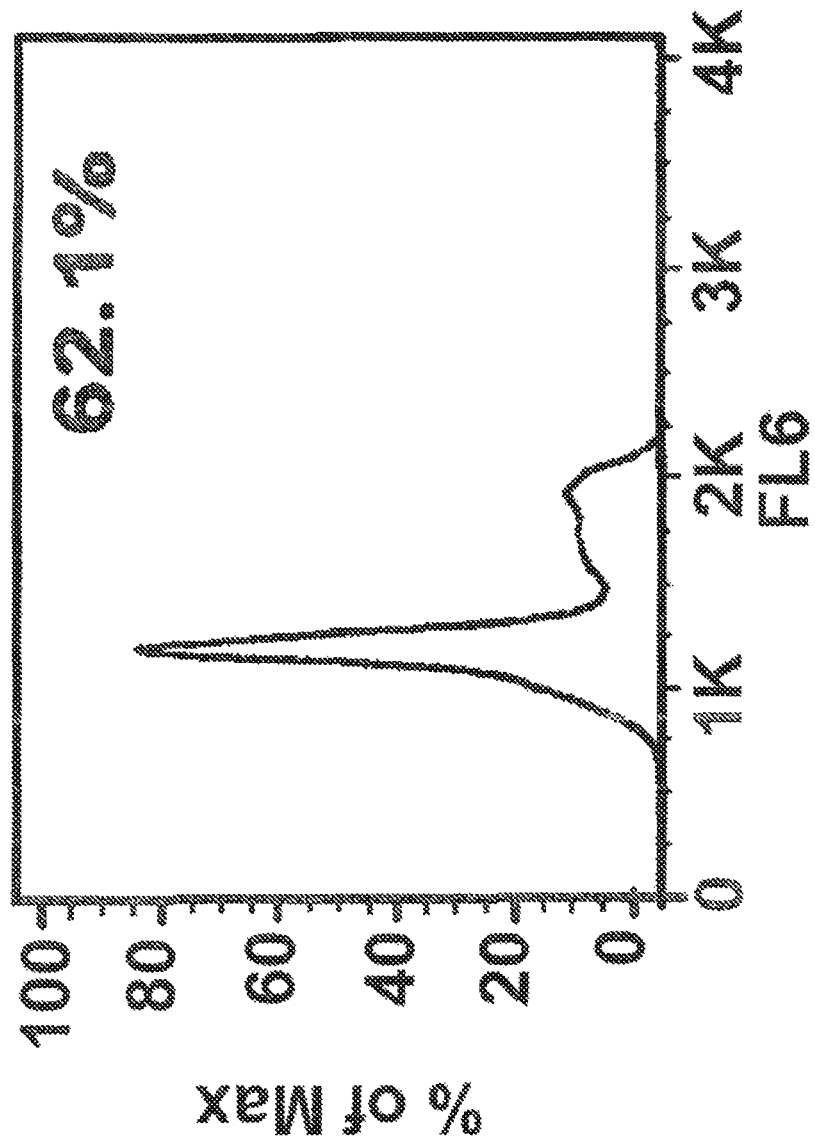
Figure 24H:
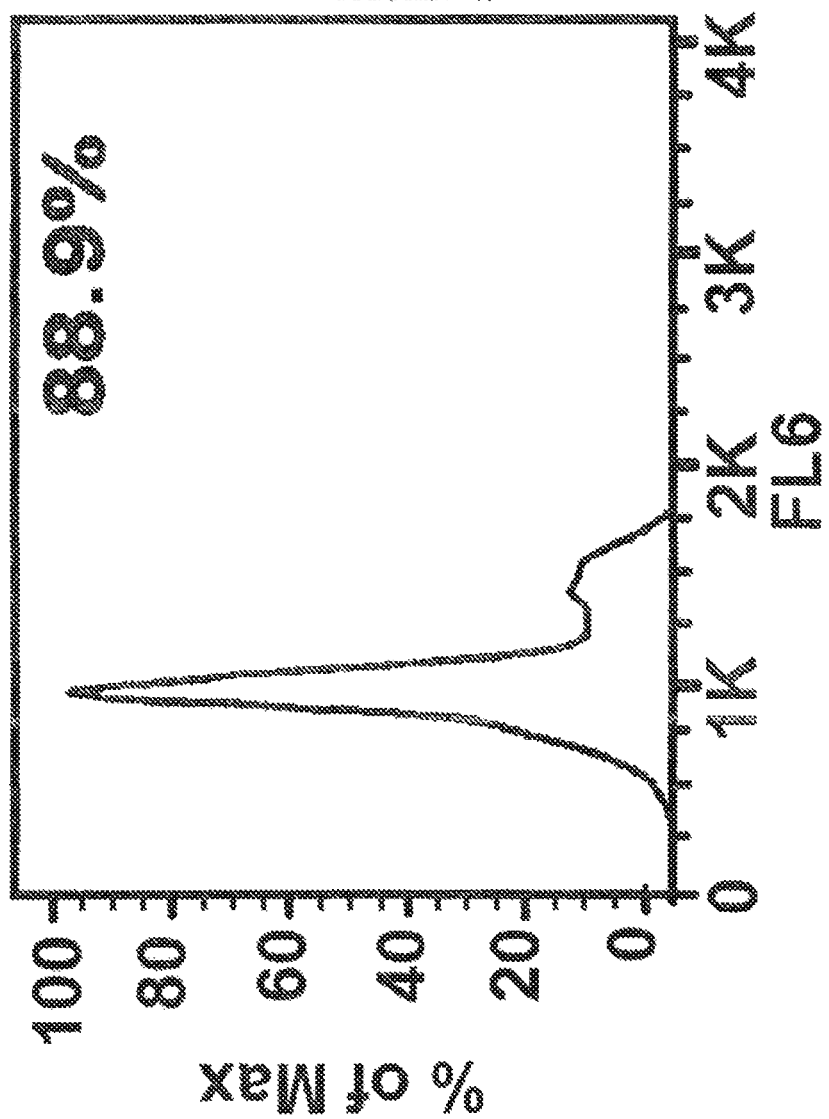
Figure 24I:
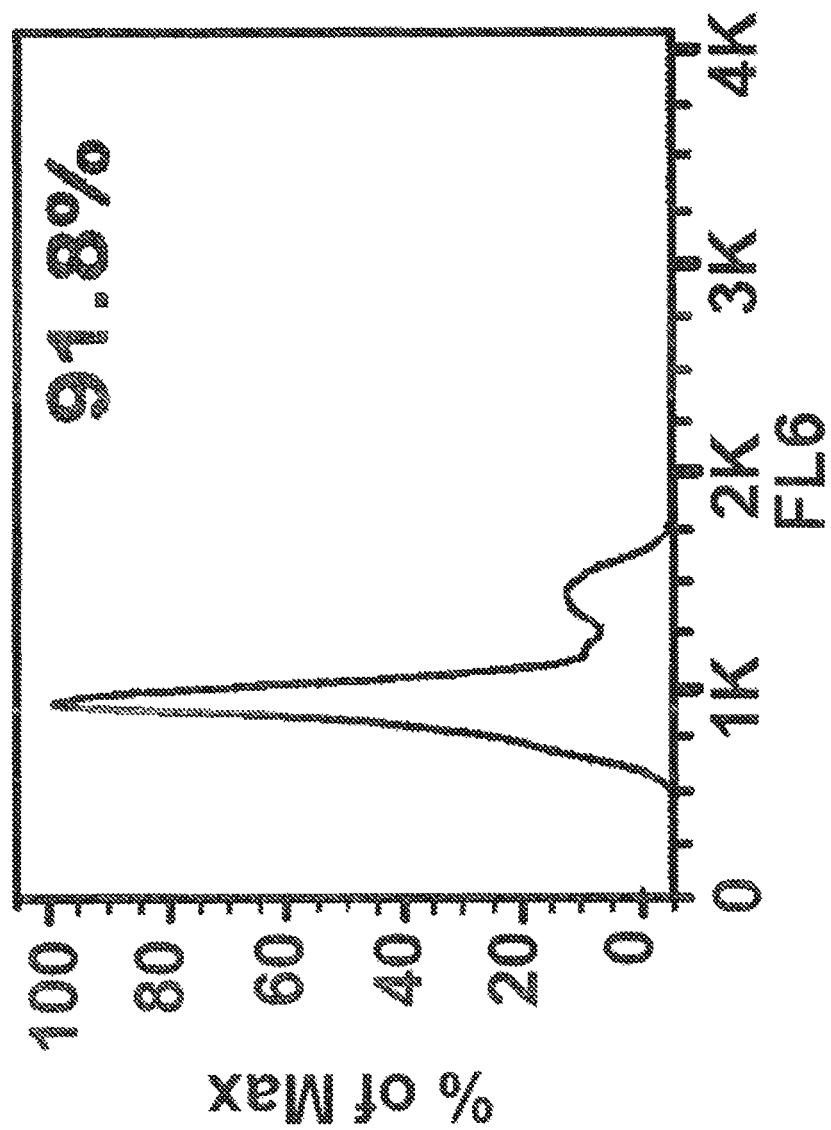

FIGS. 23(A)-(C) depict confocal fluorescence microscopy images of Hep3B cells exposed to a 1000-fold excess of MC40-targeted, pCB1-loaded protocells for 15 minutes (A), 12 hours (B), or 24 hours (C) at 37° C. For (B), endosomal escape of protocells and cytosolic dispersion of pCB1 was evident after ~2 hours; ZsGreen expression was not detectable until 12-16 hours, however. At 24 hours, Cy5-labeled pCB1 remained distributed throughout the cells; cytosolic staining is not visible in (C), however, since the gain of the Cy5 channel was reduced to avoid saturation of pixels localized within the nuclei. Silica cores were labeled with Alexa Fluor® 594 (red), pCB1 was labeled with Cy5 (white), and cell nuclei were counterstained with Hoechst 33342 (blue). Scale bars=20 μm. FIG. 23(D) shows Pearson's correlation coefficients (r-values) versus time for Cy5-labeled pCB1 and Hoechst 33342-labeled Hep3B nuclei. SlideBook software was used to determine r-values, which are expressed as the mean value±standard deviation for n=3×50 cells. Differential Interference Contrast (DIC) images were employed to define the boundaries of Hep3B cells so that pixels outside of the cell boundaries could be disregarded when calculating r-values. Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG.

Histone-Packaged pCB1, when Modified with a NLS and Delivered Via MC40-Targeted Protocells, Selectively Transfects Both Dividing and Non-Dividing HCC Cells with Nearly 100% Efficacy.

FIGS. 24 (A), (C), and (E) show confocal fluorescence microscopy images of Hep3B cells exposed to a 1000-fold excess of MC40-targeted, pCB1-loaded protocells for 24 hours at 37° C. Hep3B cells were dividing in (A) and ~95% confluent in (C) and (E); pCB1 was pre-packaged with histones in all images, and the pCB1-histone complex was further modified with a NLS in (E). Silica cores were labeled with Alexa Fluor® 594 (red), pCB1 was labeled with Cy5 (white), and cell nuclei were counterstained with Hoechst 33342 (blue). Scale bars=20 μm. FIGS. 24(B), (D), and (F) show the percentage of $1\times10^6$ Hep3B and hepatocytes that become positive for ZsGreen expression upon continual exposure to $1\times10^9$ MC40-targeted, pCB1-loaded protocells ('PC') for 24 hours at 37° C. Cells were dividing in (B) and ~95% confluent in (D) and (F); the x-axes indicate whether CB1 plasmids ('pCB1') and pCB1-histone complexes ('complex') were modified with the NLS. pCB1 alone, as well as pCB1 packaged with a 1:1 (w/w) mixture of DOTAP and DOPE were employed as controls. Cells were exposed to 20 mg/mL of wheat germ agglutinin (WGA) to block translocation of NLS-modified pCB1 through the nuclear pore complex. Error bars represent 95% confidence intervals (1.96σ) for n=3. FIGS. 24(G)-(I) Cell cycle histograms for cells employed in Figures (A), (C), and (E), respectively. The percentage of cells in $G_o/G_1$ phase is given for each histogram. In all experiments, protocell SLBs were composed of DOPC with 5 wt % DOPE, 30 wt % cholesterol, and 10 wt % PEG-2000 (18:1) and were modified with 0.015 wt % MC40 and 0.500 wt % H5WYG.

FIG. 25 shows the confocal fluorescence microscopy images of Hep3B (A) and hepatocytes (B) that were exposed to MC40-targeted, pCB1-loaded protocells for either 1 hour or 72 hours at 37° C.; the pCB1 concentration was maintained at 5 pM in all experiments. The arrows in (B) indicate mitotic cells. Cyclin B1 was labeled with an Alexa Fluor® 594-labeled monoclonal antibody (red), and cell nuclei were stained with Hoechst 33342 (blue). Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. All scale bars=20 μm.

FIG. 26 shows the confocal fluorescence microscopy images of Hep3B (A) and hepatocytes (B) that were exposed to MC40-targeted, pCB1-loaded protocells for either 1 hour or 72 hours at 37° C.; the pCB1 concentration was maintained at 5 pM in all experiments. Cells were stained with Alexa Fluor® 647-labeled annexin V (white) and propidium iodide (red) to assay for early and late apoptosis, respectively, and cell nuclei were counterstained with Hoechst 33342 (blue). Protocell SLBs were composed of DOPC with 5 wt % DOPE, 30 wt % cholesterol, and 10 wt % PEG-2000 (18:1) and were modified with 0.015 wt % MC40 and 0.500 wt % H5WYG. All scale bars=20 μm.

Protocells with a SLB Composed of Zwitterionic Lipids Induce Minimal Non-Specific Cytotoxicity.

As depicted in attached FIG. 27, the percentage of $1\times10^6$ Hep3B that become apoptotic upon continual exposure to $1\times10^9$ APTES-modified mesoporous silica nanoparticles, DOPC protocells with APTES-modified cores, DOPC protocells loaded with a plasmid that encodes a scrambled shRNA sequence ('scrambled pCB1'), or DOTAP/DOPE (1:1 w/w) lipoplexes loaded with scrambled pCB1 for 48 hours at 37° C. Protocells and lipoplexes were modified with 10 wt % PEG-2000, 0.015 wt % MC40, and 0.500 wt % H5WYG. Positively-and negatively-charged polystyrene nanoparticles ('amine-PS' and 'Carboxyl-PS', respectively) were employed as positive controls, while Hep3B exposed to 10 mM of the antioxidant, N-acetylcysteine (NAC), or to 1 pmol of free pCB1 were used as negative controls. All error bars represent 95% confidence intervals (1.96 σ) for n=3.

All references which are disclosed herein are incorporated by reference where relevant.

REFERENCES

1 Carroll, N. J., Pylypenko, S., Atanassov, P. B. & Petsev, D. N. Microparticles with Bimodal Nanoporosity Derived by Microemulsion Templating. *Langmuir*, doi:10.1021/1a900988j (2009).

2 Lu, Y. F. et al. Aerosol-assisted self-assembly of mesostructured spherical nanoparticles. *Nature* 398, 223-226 (1999).

3 Iler, R. K. *The Chemistry of Silica: Solubility, Polymerization, Colloid and Surface Properties, and Biochemistry*. (John Wiley and Sons, 1979).

4 Doshi, D. A. et al. Neutron Reflectivity Study of Lipid Membranes Assembled on Ordered Nanocomposite and Nanoporous Silica Thin Films. *Langmuir* 21, 2865-2870, doi:10.1021/1a0471240 (2005).

5 Bernhard, M. I. et al. Guinea Pig Line 10 Hepatocarcinoma Model: Characterization of Monoclonal Antibody and in Vivo Effect of Unconjugated Antibody and Antibody Conjugated to Diphtheria Toxin A Chain. *Cancer Research* 43, 4420-4428 (1983).

6 Lo, A., Lin, C. T. & Wu, H. C. Hepatocellular carcinoma cell-specific peptide ligand for targeted drug delivery. *Molecular Cancer Therapeutics* 7, 579-589, doi:10.1158/1535-7163.mct-07-2359 (2008).

7 Sciot, R. et al. Transferrin receptor expression in human hepatocellular carcinoma: an immunohistochemical study of 34 cases. *Histopathology* 12, 53-63 (1988).

8 Kannangai, R., Sahin, F. & Torbenson, M. S. EGFR is phosphorylated at Ty845 in hepatocellular carcinoma. *Mod Pathol* 19, 1456-1461 (2006).

9 Behr, J. P. The Proton Sponge: a Trick to Enter Cells the Viruses Did Not Exploit. *CHIMIA International Journal for Chemistry* 51, 34-36 (1997).

10 Jiang, W., KimBetty, Y. S., Rutka, J. T. & ChanWarren, C. W. Nanoparticle-mediated cellular response is size-dependent. *Nat Nano* 3, 145-150 (2008).

11 Zimmermann, R. et al. Charging and structure of zwitterionic supported bilayer lipid membranes studied by streaming current measurements, fluorescence microscopy, and attenuated total reflection Fourier transform infrared spectroscopy. *Biointerphases* 4, 1-6 (2009).

12 Ashihara, E., Kawata, E. & Maekawa, T. Future Prospect of RNA Interference for Cancer Therapies. *Current Drug Targets* 11, 345-360 (2010).

13 Pawitan, J. A. The possible use of RNA interference in diagnosis and treatment of various diseases. *International Journal of Clinical Practice* 63, 1378-1385 (2009).

14 Elbashir, S. M. et al. Duplexes of 21-nucleotide RNAs mediate RNA interference in cultured mammalian cells. *Nature* 411, 494-498 (2001).

15 Davis, M. E. et al. Evidence of RNAi in humans from systemically administered siRNA via targeted nanoparticles. *Nature* advance online publication (2010).

16 Oh, Y.-K. & Park, T. G. siRNA delivery systems for cancer treatment. *Advanced Drug Delivery Reviews* 61, 850-862 (2009).

17 Sou, K., Endo, T., Takeoka, S. & Tsuchida, E. Poly (ethylene glycol)-Modification of the Phospholipid Vesicles by Using the Spontaneous Incorporation of Poly (ethylene glycol)-Lipid into the Vesicles. *Bioconjugate Chemistry* 11, 372-379, doi:10.1021/bc990135y (2000).

18 Klein, E. et al. "HFP" Fluorinated Cationic Lipids for Enhanced Lipoplex Stability and Gene Delivery. *Bioconjugate Chemistry* 21, 360-371, doi:10.1021/bc900469z (2010).

19 Minguez, B., Tovar, V., Chiang, D., Villanueva, A. & Llovet, J. M. Pathogenesis of hepatocellular carcinoma and molecular therapies. *Current Opinion in Gastroenterology* 25, 186-194 110.1097/MOG.1090b1013e32832962a32832961 (2009).

20 Li, S.-D., Chen, Y.-C., Hackett, M. J. & Huang, L. Tumor-targeted Delivery of siRNA by Self-assembled Nanoparticles. *Mol Ther* 16, 163-169, doi:http://www.nature.com/mt/journal/v16/n1/suppinfo/6300323 s1.html (2007).

21 Landen, C. N. et al. Therapeutic EphA2 Gene Targeting In vivo Using Neutral Liposomal Small Interfering RNA Delivery. *Cancer Research* 65, 6910-6918 (2005).

22 Honjo, T., Nishizuka, Y., Hayaishi, 0. & Kato, I. Diphtheria Toxin-dependent Adenosine Diphosphate Ribosylation of Aminoacyl Transferase II and Inhibition of Protein Synthesis. *Journal of Biological Chemistry* 243, 3553-3555 (1968).

23 Uchida, T., Kim, J. H., Yamaizumi, M., Miyake, Y. & Okada, Y. Reconstitution of lipid vesicles associated with HVJ (Sendai virus) spikes. Purification and some properties of vesicles containing non-toxic fragment A of diphtheria toxin. *Journal of Cell Biology* 80, 10-20 (1979).

24 Mizuguchi, H. et al. Application of fusogenic liposomes containing fragment A of diphtheria toxin to cancer therapy. *British Journal of Cancer* 73, 472-476 (1997).

25 Liu, J. W., Jiang, X. M., Ashley, C. & Brinker, C. J. Electrostatically Mediated Liposome Fusion and Lipid Exchange with a Nanoparticle-Supported Bilayer for Control of Surface Charge, Drug Containment, and Delivery. *Journal of the American Chemical Society* 131, 7567-+, doi:10.1021/ja902039y (2009).

26 Liu, J. W., Stace-Naughton, A. & Brinker, C. J. Silica nanoparticle supported lipid bilayers for gene delivery. *Chemical Communications*, 5100-5102, doi:10.1039/b911472f (2009).

27 Liu, J. W., Stace-Naughton, A., Jiang, X. M. & Brinker, C. J. Porous Nanoparticle Supported Lipid Bilayers (Protocells) as Delivery Vehicles. *Journal of the American Chemical Society* 131, 1354-+, doi:10.1021/ja808018y (2009).

28 Schagger, H. Tricine-SDS-PAGE. *Nat. Protocols* 1, 16-22 (2006).

29 Fritze, A., Hens, F., Kimpfler, A., Schubert, R. & Peschka-Süss, R. Remote loading of doxorubicin into liposomes driven by a transmembrane phosphate gradient. *Biochimica et Biophysica Acta (BBA)—Biomembranes* 1758, 1633-1640 (2006).

30 Elorza, B., Elorza, M. A., Frutos, G. & Chantres, J. R. Characterization of 5-fluorouracil loaded liposomes prepared by reverse-phase evaporation or freezing-thawing extrusion methods: study of drug release. *Biochimica et Biophysica Acta* 1153, 135-142 (1993).

31 Peleg-Shulman, T., Gibson, D., Cohen, R., Abra, R. & Barenholz, Y. Characterization of sterically stabilized cisplatin liposomes by nuclear magnetic resonance. *Biochimica et Biophysica Acta* 1510, 278-291 (2001).

32 Bogush, T., Smirnova, G., Shubina, L., Syrkin, A. & Robert, J. Direct evaluation of intracellular accumulation of free and polymer-bound anthracyclines. *Cancer Chemotherapy and Pharmacology* 35, 501-505, doi:10.1007/BF00686835 (1995).

33 Tong, A. W. et al. Chemosensitization of human hepatocellular carcinoma cells with cyclosporin A in post-liver transplant patient plasma. *Clin. Cancer Res.* 2, 531-539 (1996).

34 Minko, T., Kopecková, P. & Kopecek, J. Chronic exposure to HPMA copolymer-bound adriamycin does not induce multidrug resistance in a human ovarian carcinoma cell line. *Journal of Controlled Release* 59, 133-148 (1999).

The invention claimed is:

1. A cell-targeting porous protocell composition comprising a plurality of protocells, the protocells comprising:
   a nanoporous silica or metal oxide core with a supported lipid bilayer;
   a Met binding peptide selected from the group consisting of SEQ ID NO: 1, SEQ ID NO: 2, SEQ ID NO: 3, SEQ ID NO: 4, and SEQ ID NO: 5, wherein the Met binding peptide is attached to the supported lipid bilayer;
   a fusogenic peptide that promotes endosomal escape, wherein the fusogenic peptide is attached to the supported lipid bilayer; and
   a cargo loaded into the protocell, wherein the cargo is selected from the group consisting of:
      double stranded linear DNA;
      plasmid DNA;
      a drug;
      an imaging agent;
      small interfering RNA;
      small hairpin RNA; and
      microRNA;
   wherein the cargo is optionally conjugated to a nuclear localization sequence.

2. The protocell composition according to claim 1 wherein said silica cores of the protocells are spherical and range in diameter from about 10 nm to about 250 nm.

3. The protocell composition according to claim 2 wherein said silica cores of the protocells have a mean diameter of about 150 nm.

4. The protocell composition according to any one of claims 1-3 wherein said protocells are monodisperse.

5. The protocell composition according to any one of claims 1-3 wherein said protocells are polydisperse.

6. The protocell composition according to claim 1 wherein said lipid bilayer is comprised of lipids selected from the group consisting of 1,2-dioleoyl-sn-glycero-3-phosphocholine (DOPC), 1,2-dipalmitoyi-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy (polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino] lauroyl]-sn-Glycero-3-Phosphocholine (18:1-12:0 NBD PC), 1-palmitoyl-2-{12-[(7-nitro-2-1,3-benzoxadiazol-4-yl) amino]lauroyl}-sn-glycero-3-phosphocholine (16:0-12:0 NBD PC), cholesterol and mixtures thereof.

7. The protocell composition according to claim 6 wherein said lipid bilayer comprises DOPC in combination with DOPE.

8. The protocell composition according to claim 6 wherein said lipid bilayer comprises DOTAP, DOPG, DOPC or mixtures thereof.

9. The protocell composition according to claim 6 wherein said lipid bilayer comprises DOPG and DOPC.

10. The protocell composition according to claim 6 wherein said lipid bilayer comprises cholesterol.

11. The protocell composition according to claim 1 wherein said lipid bilayer comprises DOPC in combination with about 5 wt % DOPE, about 30 wt % cholesterol, and about 10 wt % PEG-2000 PE (18:1).

12. The protocell composition according to claim 1 wherein lipid bilayer comprises about 5% by weight DOPE, about 30% by weight cholesterol, and about 60% by weight DOPC and/or DPPC.

13. The protocell composition according to claim 1 wherein the lipid bilayer comprises PEG-conjugated to DOPE.

14. The protocell composition according to claim 1 wherein said protocells further comprise an additional targeting peptide.

15. The protocell composition according to claim 14 wherein said targeting peptide is a SP94 peptide.

16. The protocell composition according to claim 14 wherein said targeting peptide is SEQ ID NO: 6, SEQ ID NO: 7 or SEQ ID NO: 8.

17. The protocell composition according to claim 1 wherein said fusogenic peptide is H5WYG peptide (SEQ ID NO: 13) or an eight mer of polyarginine (SEQ ID NO: 14).

18. The protocell composition according to claim 17 wherein said fusogenic peptide is SEQ ID NO: 13.

19. The protocell composition according to claim 1 wherein the cargo comprises plasmid DNA.

20. The protocell composition according to claim 19 wherein said plasmid DNA is supercoiled or packaged plasmid DNA.

21. The protocell composition according to claim 20 wherein said DNA is both supercoiled and packaged plasmid DNA.

22. The protocell according to claim 19 wherein said plasmid DNA is conjugated to a nuclear localization sequence.

23. The protocell composition according to claim 19 wherein said plasmid DNA is histone-packaged supercoiled plasmid DNA and comprises a mixture of human histone proteins.

24. The protocell composition according to any of claim 1 wherein said plasmid DNA encodes a polypeptide toxin, a small hairpin RNA (shRNA) or a small interfering RNA (siRNA).

25. The protocell composition according to claim 24 wherein said polypeptide toxin is selected from the group consisting of ricin toxin chain-A and diphtheria toxin chain-A.

26. The protocell composition according to claim 24 wherein said shRNA or said siRNA induces apoptosis of a cell.

27. The protocell composition according to claim 1 wherein said DNA encodes a reporter protein.

28. The protocell composition according to claim 27 wherein said reporter protein is green fluorescent protein or red fluorescent protein.

29. The protocell composition according to claim 27 wherein said MET binding peptide is a peptide according to SEQ ID NO: 1.

30. The protocell composition according to claim 1 wherein said nuclear localization sequence is a peptide according to SEQ ID NO: 9, SEQ ID NO: 10, SEQ ID NO: 11 or SEQ ID NO: 12.

31. The protocell composition according to claim 1 wherein said cargo comprises said drug, and said drug is an anticancer agent.

32. The protocell composition according to claim 31 wherein said anticancer agent is everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfbnylpiperadinemethyl)-indolyij-quinolone, vatalanib, AG-013736, AVE-0005, the acetate salt of [D-Ser(Bu t) 6, Azgly 10](pyro-Glu-His-Trp-Ser-Tyr-D-Ser(Bu t)-Leu-Arg-Pro-Azgly-NH$_2$ acetate [$C_{59}H_{84}N_{18}Oi_4$ —($C_2H_4$ $O_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafamib, BMS-214662, tipifarnib; amifostine, NVP-LAQ824, suberoyl analide hydroxamic acid, valproic acid, trichostatin A, FX-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxyrnesterone, flutamide, gemcitabine, gleevac, hydroxyurea, idarubicin, ifosfamide, imatmib, leuprolide, levamisole, lomustine, mechlorethamine, melphalan, 6-mercaptopurine, mesna, methotrexate, mitomycin, mitotane, mitoxantrone, nilutamide, octreotide, oxalipiatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycofbrmycin, calcitriol, valrubicin, mithrarnycin, vinblastine, vinoretbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasolbxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositunioniab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methyiprednisolone, prochlorperazine, granisetron, ondansetron, dolasetron, tropisetron, pegfilgrastim, erythropoietin, epoetin alfa, darbepoetin alfa or a mixture thereof.

33. A pharmaceutical composition comprising the protocell composition according to claim 1 in an amount effective for effecting a therapeutic effect in combination with a pharmaceutically acceptable carrier, additive or excipient.

34. The pharmaceutical composition according to claim 33 further comprising a drug which is not disposed as cargo within the protocell.

35. The pharmaceutical composition according to claim 34 wherein said drug is an anti-cancer agent or an anti-viral agent.

36. The pharmaceutical composition according to claim 33 in parenteral dosage form.

37. The pharmaceutical composition according to claim 36 wherein said dosage form is intradermal, intramuscular, intraosseous, intraperitoneal, intravenous, subcutaneous or intrathecal.

38. The pharmaceutical composition according to claim 33 in topical or transdermal dosage form.

39. A protocell comprising a nanoporous silica core with a supported lipid bilayer and a MET binding peptide according to SEQ ID NO: 1, SEQ ID NO: 2, SEQ ID NO:3, SEQ ID NO: 4 or SEQ ID NO: 5, attached to the supported lipid bilayer.

40. The photocell according to claim 39 wherein said protocell further comprises at least one component selected from a fusogenic peptide that promotes endosomal escape of protocells and encapsulated DNA; a plasmid DNA; double stranded linear DNA; a drug; an imaging agent; small interfering RNA; small hairpin RNA; or micro RNA, wherein said plasmid or double stranded linear DNA, said drug, said imaging agent and/or said small interfering, small hairpin or micro RNA are further conjugated with a nuclear localization sequence.

41. The protocell according to claim 40 wherein said drug comprises at least one one anticancer agent.

42. The protocell according to claim 41 wherein said anticancer agent is selected from everollimus, trabectedin, abraxane, TLK 286,AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, ohlimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl) ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolyij-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amilbstine, NVP-LAQ824, suberoyl analide hydroxamic acid, valproic acid, trichostatin A, FK-228, SU11248, sorafenib, KRN951, aminogiutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acoibifene, lasofoxitene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alerntuzumab, all-transretinoic acid, ketoconazole, interleukin-2, megestrol, immune globulin, nitrogen mustard, methylprednisolone, ibritgunioniab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim erythropoietin, epoetin alfa, darbepoetin alfa or mixtures thereof.

43. The protocell according to claim 40 wherein said plasmid or double stranded linear DNA encodes at least one reporter molecule.

44. The protocell according to claim 40 comprising the plasmid DNA, wherein said plasmid DNA optionally encodes a nuclear localization sequence.

45. A method of treating cancer in a patient comprising administering to the cancer in the patient in need thereof an effective amount of a composition comprising a population of protocells according to claim 1 wherein the cargo is an anticancer agent.

* * * * *

SEQUENCE LISTING

```
<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Ala Ser Val His Phe Pro Pro
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide

<400> SEQUENCE: 2

Thr Ala Thr Phe Trp Phe Gln
1               5

<210> SEQ ID NO 3
<211> LENGTH: 7
<212> TYPE: PRT
<213> ORGANISM: Artificial Sequence
<220> FEATURE:
<223> OTHER INFORMATION: synthetic peptide

<400> SEQUENCE: 3

Thr Ser Pro Val Ala Leu Leu
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Ile Pro Leu Lys Val His Pro
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Trp Pro Arg Leu Thr Asn Met
1               5
```

```
<210> SEQ ID NO 6
<211> LENGTH: 12
<212> TYPE: PRT
<213> ORGANISM: Artificial Sequence
<220> FEATURE:
<223> OTHER INFORMATION: synthetic peptide

<400> SEQUENCE: 6

Ser Phe Ser Ile Ile Leu Thr Pro Ile Leu Pro Leu
1               5                   10

<210> SEQ ID NO 7
<211> LENGTH: 15
<212> TYPE: PRT
<213> ORGANISM: Artificial Sequence
<220> FEATURE:
<223> OTHER INFORMATION: synthetic peptide

<400> SEQUENCE: 7

Ser Phe Ser Ile Ile Leu Thr Pro Ile Leu Pro Leu Gly Gly Cys
1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: synthetic peptide

<400> SEQUENCE: 8

Ser Phe Ser Ile Ile Leu Thr Pro Ile Leu Pro Leu Glu Glu Glu Gly
1               5                   10                  15

Gly Cys

<210> SEQ ID NO 9
<211> LENGTH: 42
<212> TYPE: PRT
<213> ORGANISM: Artificial Sequence
<220> FEATURE:
<223> OTHER INFORMATION: synthetic peptide

<400> SEQUENCE: 9

Gly Asn Gln Ser Ser Asn Phe Gly Pro Met Lys Gly Gly Asn Phe Gly
1               5                   10                  15

Gly Arg Ser Ser Gly Pro Tyr Gly Gly Gly Gln Tyr Phe Ala Lys
            20                  25                  30

Pro Arg Asn Gln Gly Gly Tyr Gly Gly Cys
        35                  40

<210> SEQ ID NO 10
<211> LENGTH: 7
<212> TYPE: PRT
<213> ORGANISM: Artificial Sequence
<220> FEATURE:
<223> OTHER INFORMATION: synthetic peptide

<400> SEQUENCE: 10

Arg Arg Met Lys Trp Lys Lys
1               5

<210> SEQ ID NO 11
<211> LENGTH: 7
<212> TYPE: PRT
<213> ORGANISM: Artificial Sequence
<220> FEATURE:
```

<223> OTHER INFORMATION: synthetic peptide

<400> SEQUENCE: 11

Pro Lys Lys Lys Arg Lys Val
1               5

<210> SEQ ID NO 12
<211> LENGTH: 16
<212> TYPE: PRT
<213> ORGANISM: Artificial Sequence
<220> FEATURE:
<223> OTHER INFORMATION: synthetic peptide

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 25
<212> TYPE: PRT
<213> ORGANISM: Artificial Sequence
<220> FEATURE:
<223> OTHER INFORMATION: synthetic peptide

<400> SEQUENCE: 13

Gly Leu Phe His Ala Ile Ala His Phe Ile His Gly Gly Trp His Gly
1               5                   10                  15

Leu Ile His Gly Trp Tyr Gly Gly Cys
            20                  25

<210> SEQ ID NO 14
<211> LENGTH: 8
<212> TYPE: PRT
<213> ORGANISM: Artificial Sequence
<220> FEATURE:
<223> OTHER INFORMATION: synthetic peptide

<400> SEQUENCE: 14

Arg Arg Arg Arg Arg Arg Arg Arg
1               5

<210> SEQ ID NO 15
<211> LENGTH: 12
<212> TYPE: PRT
<213> ORGANISM: Artificial Sequence
<220> FEATURE:
<223> OTHER INFORMATION: synthetic peptide

<400> SEQUENCE: 15

Tyr Leu Phe Ser Val His Trp Pro Pro Leu Lys Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: synthetic peptide

<400> SEQUENCE: 16

His Ala Ile Tyr Pro Arg His
1               5

<210> SEQ ID NO 17
<211> LENGTH: 7
<212> TYPE: PRT

```
<213> ORGANISM: Artificial Sequence
<220> FEATURE:
<223> OTHER INFORMATION: synthetic peptide

<400> SEQUENCE: 17

Thr Pro Asp Trp Leu Phe Pro
1               5
```